United States Patent
Ahmed et al.

(10) Patent No.: US 11,124,568 B1
(45) Date of Patent: *Sep. 21, 2021

(54) CD3/CD25 ANTIBODIES FOR NEURO-IMMUNE DISEASES

(71) Applicant: Vitruviae LLC, Nutley, NJ (US)

(72) Inventors: Mahiuddin Ahmed, Verona, NJ (US); Sonia Sequeira, Verona, NJ (US)

(73) Assignee: Vitruviae LLC, Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/997,570

(22) Filed: Aug. 19, 2020

(51) Int. Cl.
*C07K 16/28* (2006.01)

(52) U.S. Cl.
CPC ...... *C07K 16/2809* (2013.01); *C07K 16/2866* (2013.01); *C07K 2317/24* (2013.01); *C07K 2317/31* (2013.01); *C07K 2317/52* (2013.01); *C07K 2317/56* (2013.01); *C07K 2317/565* (2013.01); *C07K 2317/622* (2013.01)

(58) Field of Classification Search
CPC ............ C07K 16/2809; C07K 16/2866; C07K 2317/56; C07K 2317/24; C07K 2317/52; C07K 2317/31; C07K 2317/622; C07K 2317/565

See application file for complete search history.

(56) References Cited

U.S. PATENT DOCUMENTS

| | | | |
|---|---|---|---|
| 2014/0294823 A1* | 10/2014 | Moore | C07K 16/22 424/134.1 |
| 2018/0371089 A1* | 12/2018 | Wu | C07K 16/2809 |

FOREIGN PATENT DOCUMENTS

| | | | | |
|---|---|---|---|---|
| WO | WO-2008086006 A2 * | 7/2008 | | A61P 9/00 |
| WO | WO-2010102251 A2 * | 9/2010 | | A61P 25/00 |
| WO | WO-2016071004 A1 * | 5/2016 | | C07K 16/468 |
| WO | WO-2017008169 A1 * | 1/2017 | | C40B 40/02 |
| WO | WO-2017181139 A2 * | 10/2017 | | A61P 35/00 |
| WO | WO-2017218707 A2 * | 12/2017 | | C07K 16/2803 |

OTHER PUBLICATIONS

Wong et al. (Journal of Immunology 1993; 150:1619-1628) Anti-CD3:Anti-IL-2 Receptor Bispecific Monoclonal Antibody. (Year: 1993).*
Ahmed et al (PLOS ONE | www.plosone.org May 1, 2013 | vol. 8 | Issue 5 | e63359.In silico Driven Redesign of a Clinically Relevant Antibody for the Treatment of GD2 Positive Tumors (Year: 2013).*
Cheng et al,(Int. J. Cancer: 136, 476-486 (2015.)Structural design of disialoganglioside GD2 and CD3-bispecific antibodies to redirect T cells for tumor therapy (Year: 2015).*

* cited by examiner

*Primary Examiner* — Amy E Juedes
*Assistant Examiner* — Brian Hartnett
(74) *Attorney, Agent, or Firm* — Holzer Patel Drennan

(57) ABSTRACT

The present invention relates to the use of anti-CD3 and anti-CD25 antibodies for the management and treatment of inflammatory diseases and psycho-immune disorders, such as depression, autism (ASD) and attention deficit/hyperactivity disorder (ADHD).

16 Claims, 2 Drawing Sheets

Figure 1:
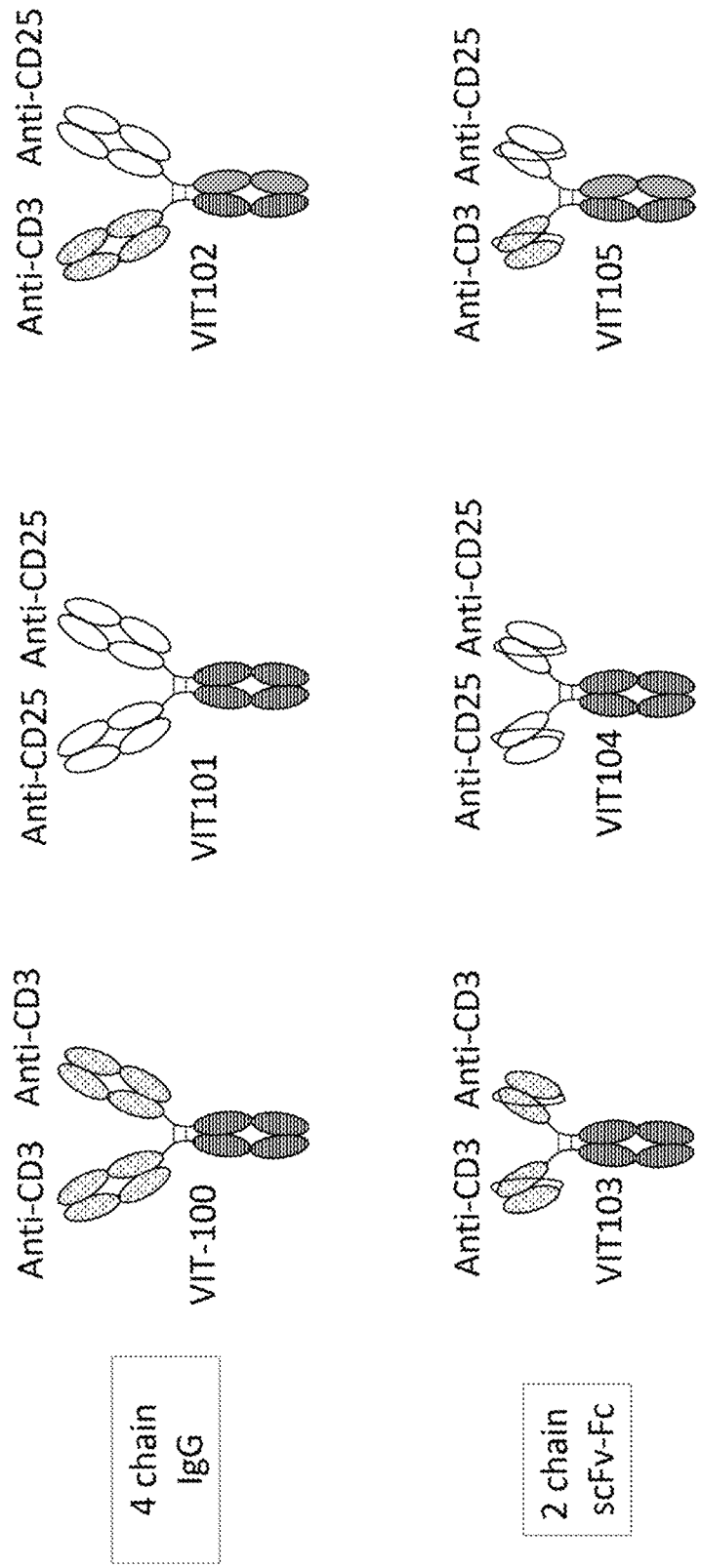

Specification includes a Sequence Listing.

SEQUENCE LISTING

```
<160> NUMBER OF SEQ ID NOS: 93

<210> SEQ ID NO 1
<211> LENGTH: 106
<212> TYPE: PRT
<213> ORGANISM: Mus musculus

<400> SEQUENCE: 1

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80
```

```
Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 2
<211> LENGTH: 106
<212> TYPE: PRT
<213> ORGANISM: Artificial Sequence
<220> FEATURE:
<223> OTHER INFORMATION: Teplizumab VL

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Thr Pro Gly Lys Ala Pro Lys Arg Trp Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr
            100                 105

<210> SEQ ID NO 3
<211> LENGTH: 106
<212> TYPE: PRT
<213> ORGANISM: Artificial Sequence
<220> FEATURE:
<223> OTHER INFORMATION: VCD3-L1

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Gln Ala Ser Ser Val Ser Tyr Met
            20                  25                  30

Asn Trp Tyr Gln Gln Lys Pro Gly Lys Ala Pro Lys Arg Trp Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Glu Ile Lys
            100                 105

<210> SEQ ID NO 4
<211> LENGTH: 106
<212> TYPE: PRT
<213> ORGANISM: Artificial Sequence
<220> FEATURE:
<223> OTHER INFORMATION: VCD3-L2

<400> SEQUENCE: 4
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

Asn Trp Tyr Gln Gln Lys Pro Gly Gln Ala Pro Arg Arg Leu Ile Tyr
            35                  40                  45

Asp Thr Ser Lys Arg Ala Thr Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Ala Ala Val Tyr Tyr Cys Gln Gln Trp Ser Ser Asn Pro Phe Thr
                85                  90                  95

Phe Gly Gln Gly Thr Lys Leu Glu Ile Lys
            100                 105

<210> SEQ ID NO 5
<211> LENGTH: 106
<212> TYPE: PRT
<213> ORGANISM: Artificial Sequence
<220> FEATURE:
<223> OTHER INFORMATION: VCD3-L3

<400> SEQUENCE: 5

Glu Ile Gln Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

Asn Trp Tyr Gln Gln Lys Pro Gly Gln Ala Pro Arg Arg Trp Ile Tyr
            35                  40                  45

Asp Thr Ser Lys Leu Ala Thr Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Ala Ala Val Tyr Tyr Cys Gln Gln Trp Ser Ser Asn Pro Phe Thr
                85                  90                  95

Phe Gly Gln Gly Thr Lys Leu Glu Ile Lys
            100                 105

<210> SEQ ID NO 6
<211> LENGTH: 119
<212> TYPE: PRT
<213> ORGANISM: Mus musculus

<400> SEQUENCE: 6

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly

```
                     100                 105                 110
Thr Thr Leu Thr Val Ser Ser
            115

<210> SEQ ID NO 7
<211> LENGTH: 119
<212> TYPE: PRT
<213> ORGANISM: Artificial Sequence
<220> FEATURE:
<223> OTHER INFORMATION: Teplizumab VH

<400> SEQUENCE: 7

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
            115

<210> SEQ ID NO 8
<211> LENGTH: 119
<212> TYPE: PRT
<213> ORGANISM: Artificial Sequence
<220> FEATURE:
<223> OTHER INFORMATION: VCD3-H1

<400> SEQUENCE: 8

Gln Val Gln Leu Val Gln Ser Gly Gly Gly Val Val Gln Pro Gly Arg
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Val
        35                  40                  45

Gly Tyr Ile Asn Pro Ser Arg Gly Tyr Thr Asn Tyr Thr Asp Ser Val
    50                  55                  60

Lys Gly Arg Phe Thr Ile Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser
            115

<210> SEQ ID NO 9
<211> LENGTH: 119
<212> TYPE: PRT
<213> ORGANISM: Artificial Sequence
<220> FEATURE:
```

```
<223> OTHER INFORMATION: VCD3-H2

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: VCD3-H3

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ser Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser
        115

<210> SEQ ID NO 11
<211> LENGTH: 255
<212> TYPE: PRT
<213> ORGANISM: Artificial Sequence
<220> FEATURE:
<223> OTHER INFORMATION: VCD3-H1L1

<400> SEQUENCE: 11

Gln Val Gln Leu Val Gln Ser Gly Gly Gly Val Val Gln Pro Gly Arg
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Val
```

```
                35                  40                  45
Gly Tyr Ile Asn Pro Ser Arg Gly Tyr Thr Asn Tyr Asn Asp Ser Val
 50                  55                  60

Lys Gly Arg Phe Thr Ile Ser Thr Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Asp Asp His Tyr Ser Leu Asp Tyr Trp Gly Gln Gly
                100                 105                 110

Thr Thr Val Thr Val Ser Ser Gly Gly Gly Ser Gly Gly Gly Gly
            115                 120                 125

Ser Gly Gly Gly Gly Ser Gly Gly Gly Ser Gly Gly Gly Ser
        130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Gln Ala Ser Ser
                165                 170                 175

Ser Val Ser Tyr Met Asn Trp Tyr Gln Gln Lys Pro Gly Lys Ala Pro
            180                 185                 190

Lys Arg Trp Ile Tyr Asp Thr Ser Lys Leu Ala Ser Gly Val Pro Ser
                195                 200                 205

Arg Phe Ser Gly Ser Gly Ser Gly Thr Asp Tyr Thr Phe Thr Ile Ser
210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Gln Gly Thr Lys Leu Glu Ile Lys
                245                 250                 255

<210> SEQ ID NO 12
<211> LENGTH: 255
<212> TYPE: PRT
<213> ORGANISM: Artificial Sequence
<220> FEATURE:
<223> OTHER INFORMATION: VCD3-H1L1-DS

<400> SEQUENCE: 12

Gln Val Gln Leu Val Gln Ser Gly Gly Gly Val Val Gln Pro Gly Arg
1               5                  10                  15

Ser Leu Arg Leu Ser Cys Ala Ala Ser Gly Tyr Thr Phe Thr Arg Tyr
                 20                  25                  30

Thr Met His Trp Val Arg Gln Ala Pro Gly Lys Cys Leu Glu Trp Val
            35                  40                  45

Gly Tyr Ile Asn Pro Ser Arg Gly Tyr Thr Asn Tyr Asn Asp Ser Val
 50                  55                  60

Lys Gly Arg Phe Thr Ile Ser Thr Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Asp Asp His Tyr Ser Leu Asp Tyr Trp Gly Gln Gly
                100                 105                 110

Thr Thr Val Thr Val Ser Ser Gly Gly Gly Gly Ser Gly Gly Gly Gly
            115                 120                 125

Ser Gly Gly Gly Gly Ser Gly Gly Gly Gly Ser Gly Gly Gly Gly Ser
        130                 135                 140

Gly Gly Gly Gly Ser Asp Ile Gln Met Thr Gln Ser Pro Ser Ser Leu
```

```
                145                 150                 155                 160
Ser Ala Ser Val Gly Asp Arg Val Thr Ile Thr Cys Gln Ala Ser Ser
                165                 170                 175

Ser Val Ser Tyr Met Asn Trp Tyr Gln Gln Lys Pro Gly Lys Ala Pro
            180                 185                 190

Lys Arg Trp Ile Tyr Asp Thr Ser Lys Leu Ala Ser Gly Val Pro Ser
        195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Cys Gly Thr Lys Leu Glu Ile Lys
                245                 250                 255

<210> SEQ ID NO 13
<211> LENGTH: 255
<212> TYPE: PRT
<213> ORGANISM: Artificial Sequence
<220> FEATURE:
<223> OTHER INFORMATION: VCD3-H1L2

<400> SEQUENCE: 13

Gln Val Gln Leu Val Gln Ser Gly Gly Gly Val Val Gln Pro Gly Arg
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Val
        35                  40                  45

Gly Tyr Ile Asn Pro Ser Arg Gly Tyr Thr Asn Tyr Asn Asp Ser Val
    50                  55                  60

Lys Gly Arg Phe Thr Ile Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Leu Ile Tyr Asp Thr Ser Lys Arg Ala Thr Gly Ile Pro Ala
        195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
                245                 250                 255
```

```
<210> SEQ ID NO 14
<211> LENGTH: 255
<212> TYPE: PRT
<213> ORGANISM: Artificial Sequence
<220> FEATURE:
<223> OTHER INFORMATION: VCD3-H1L2-DS

<400> SEQUENCE: 14

Gln Val Gln Leu Val Gln Ser Gly Gly Gly Val Val Gln Pro Gly Arg
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Cys Leu Glu Trp Val
        35                  40                  45

Gly Tyr Ile Asn Pro Ser Arg Gly Tyr Thr Asn Tyr Asn Asp Ser Val
    50                  55                  60

Lys Gly Arg Phe Thr Ile Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gly Gly Gly Ser Gly Gly Gly Ser
    130                 135                 140

Gly Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Leu Ile Tyr Asp Thr Ser Lys Arg Ala Thr Gly Ile Pro Ala
        195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Cys Gly Thr Lys Leu Glu Ile Lys
                245                 250                 255

<210> SEQ ID NO 15
<211> LENGTH: 255
<212> TYPE: PRT
<213> ORGANISM: Artificial Sequence
<220> FEATURE:
<223> OTHER INFORMATION: VCD3-H1L3

<400> SEQUENCE: 15

Gln Val Gln Leu Val Gln Ser Gly Gly Gly Val Val Gln Pro Gly Arg
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Val
        35                  40                  45

Gly Tyr Ile Asn Pro Ser Arg Gly Tyr Thr Asn Tyr Asn Asp Ser Val
    50                  55                  60
```

```
Lys Gly Arg Phe Thr Ile Ser Thr Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gly Gly Gly Gly Ser Gly Gly Gly Ser
    130                 135                 140

Gly Gly Gly Gly Ser Glu Ile Gln Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Trp Ile Tyr Asp Thr Ser Lys Leu Ala Thr Gly Ile Pro Ala
        195                 200                 205

Arg Phe Ser Gly Ser Gly Ser Gly Thr Asp Tyr Thr Leu Thr Ile Ser
210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
                245                 250                 255

<210> SEQ ID NO 16
<211> LENGTH: 255
<212> TYPE: PRT
<213> ORGANISM: Artificial Sequence
<220> FEATURE:
<223> OTHER INFORMATION: VCD3-H1L3-DS

<400> SEQUENCE: 16

Gln Val Gln Leu Val Gln Ser Gly Gly Gly Val Val Gln Pro Gly Arg
  1               5                  10                  15

Ser Leu Arg Leu Ser Cys Ala Ala Ser Gly Tyr Thr Phe Thr Arg Tyr
             20                  25                  30

Thr Met His Trp Val Arg Gln Ala Pro Gly Lys Cys Leu Glu Trp Val
         35                  40                  45

Gly Tyr Ile Asn Pro Ser Arg Gly Tyr Thr Asn Tyr Asn Asp Ser Val
     50                  55                  60

Lys Gly Arg Phe Thr Ile Ser Thr Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gly Gly Gly Gly Ser Gly Gly Gly Ser
    130                 135                 140

Gly Gly Gly Gly Ser Glu Ile Gln Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175
```

```
Ser Val Ser Tyr Met Asn Trp Tyr Gln Gln Lys Pro Gly Gln Ala Pro
            180                 185                 190

Arg Arg Trp Ile Tyr Asp Thr Ser Lys Leu Ala Thr Gly Ile Pro Ala
        195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Cys Gly Thr Lys Leu Glu Ile Lys
                245                 250                 255

<210> SEQ ID NO 17
<211> LENGTH: 255
<212> TYPE: PRT
<213> ORGANISM: Artificial Sequence
<220> FEATURE:
<223> OTHER INFORMATION: VCD3-H2L1

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Gln Ala Ser Ser
                165                 170                 175

Ser Val Ser Tyr Met Asn Trp Tyr Gln Gln Lys Pro Gly Lys Ala Pro
            180                 185                 190

Lys Arg Trp Ile Tyr Asp Thr Ser Lys Leu Ala Ser Gly Val Pro Ser
        195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Gln Gly Thr Lys Leu Glu Ile Lys
                245                 250                 255

<210> SEQ ID NO 18
<211> LENGTH: 255
<212> TYPE: PRT
<213> ORGANISM: Artificial Sequence
<220> FEATURE:
```

<223> OTHER INFORMATION: VCD3-H2L1-DS

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Ser Gly Gly Gly Ser Gly Gly Gly Ser
    130                 135                 140

Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Gln Ala Ser
            165                 170                 175

Ser Val Ser Tyr Met Asn Trp Tyr Gln Gln Lys Pro Lys Ala Pro
            180                 185                 190

Lys Arg Trp Ile Tyr Asp Thr Ser Lys Leu Ala Ser Gly Val Pro Ser
            195                 200                 205

Arg Phe Ser Gly Ser Gly Ser Gly Thr Asp Tyr Thr Phe Thr Ile Ser
        210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Cys Gly Thr Lys Leu Glu Ile Lys
                245                 250                 255

<210> SEQ ID NO 19
<211> LENGTH: 255
<212> TYPE: PRT
<213> ORGANISM: Artificial Sequence
<220> FEATURE:
<223> OTHER INFORMATION: VCD3-H2L2

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Tyr Tyr Asp Asp His Tyr Ser Leu Asp Tyr Trp Gly Gln Gly
                100                 105                 110

Thr Thr Val Thr Val Ser Ser Gly Gly Gly Ser Gly Gly Gly Gly
        115                 120                 125

Ser Gly Gly Gly Ser Gly Gly Gly Ser Gly Gly Gly Ser
130                 135                 140

Gly Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
                180                 185                 190

Arg Arg Leu Ile Tyr Asp Thr Ser Lys Arg Ala Thr Gly Ile Pro Ala
                195                 200                 205

Arg Phe Ser Gly Ser Gly Ser Gly Thr Asp Tyr Thr Leu Thr Ile Ser
                210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
                245                 250                 255

<210> SEQ ID NO 20
<211> LENGTH: 255
<212> TYPE: PRT
<213> ORGANISM: Artificial Sequence
<220> FEATURE:
<223> OTHER INFORMATION: VCD3-H2L2-DS

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Cys Leu Glu Trp Met
            35                  40                  45

Gly Tyr Ile Asn Pro Ser Arg Gly Tyr Thr Asn Tyr Asn Gln Lys Phe
50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
                100                 105                 110

Thr Thr Val Thr Val Ser Ser Gly Gly Gly Ser Gly Gly Gly Gly
        115                 120                 125

Ser Gly Gly Gly Ser Gly Gly Gly Ser Gly Gly Gly Ser
130                 135                 140

Gly Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
                180                 185                 190

Arg Arg Leu Ile Tyr Asp Thr Ser Lys Arg Ala Thr Gly Ile Pro Ala
                195                 200                 205
```

```
Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Cys Gly Thr Lys Leu Glu Ile Lys
                245                 250                 255

<210> SEQ ID NO 21
<211> LENGTH: 255
<212> TYPE: PRT
<213> ORGANISM: Artificial Sequence
<220> FEATURE:
<223> OTHER INFORMATION: VCD3-H2L3

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Met
            35                  40                  45

Gly Tyr Ile Asn Pro Ser Arg Gly Tyr Thr Asn Tyr Asn Gln Lys Phe
        50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
                100                 105                 110

Thr Thr Val Thr Val Ser Ser Gly Gly Gly Gly Ser Gly Gly Gly Gly
            115                 120                 125

Ser Gly Gly Gly Gly Ser Gly Gly Gly Gly Ser Gly Gly Gly Gly Ser
        130                 135                 140

Gly Gly Gly Gly Ser Glu Ile Gln Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
                180                 185                 190

Arg Arg Trp Ile Tyr Asp Thr Ser Lys Leu Ala Thr Gly Ile Pro Ala
            195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
                245                 250                 255

<210> SEQ ID NO 22
<211> LENGTH: 255
<212> TYPE: PRT
<213> ORGANISM: Artificial Sequence
<220> FEATURE:
<223> OTHER INFORMATION: VCD3-H2L3-DS

<400> SEQUENCE: 22

Gln Val Gln Leu Val Gln Ser Gly Ala Glu Val Lys Lys Pro Gly Ala
```

-continued

```
              1               5                  10                 15
            Ser Val Lys Val Ser Cys Lys Ala Ser Gly Tyr Thr Phe Thr Arg Tyr
                        20                  25                  30

Thr Met His Trp Val Arg Gln Ala Pro Gly Gln Cys Leu Glu Trp Met
                        35                  40                  45

Gly Tyr Ile Asn Pro Ser Arg Gly Tyr Thr Asn Tyr Asn Gln Lys Phe
                        50                  55                  60

Gln Gly Arg Val Thr Met Thr Thr Asp Lys Ser Thr Ser Thr Ala Tyr
            65                      70                  75                  80

Met Glu Leu Ser Ser Leu Arg Ser Glu Asp Thr Ala Val Tyr Tyr Cys
                                85                  90                  95

Ala Arg Tyr Tyr Asp Asp His Tyr Ser Leu Asp Tyr Trp Gly Gln Gly
                                100                 105                 110

Thr Thr Val Thr Val Ser Ser Gly Gly Gly Gly Ser Gly Gly Gly Gly
                        115                 120                 125

Ser Gly Gly Gly Gly Ser Gly Gly Gly Gly Ser Gly Gly Gly Gly Ser
                        130                 135                 140

Gly Gly Gly Ser Glu Ile Gln Leu Thr Gln Ser Pro Ala Thr Leu
            145                     150                 155                 160

Ser Leu Ser Pro Gly Glu Arg Ala Thr Leu Ser Cys Arg Ala Ser Ser
                                165                 170                 175

Ser Val Ser Tyr Met Asn Trp Tyr Gln Gln Lys Pro Gly Gln Ala Pro
                        180                 185                 190

Arg Arg Trp Ile Tyr Asp Thr Ser Lys Leu Ala Thr Gly Ile Pro Ala
                        195                 200                 205

Arg Phe Ser Gly Ser Gly Ser Gly Thr Asp Tyr Thr Leu Thr Ile Ser
                        210                 215                 220

Ser Leu Glu Pro Glu Asp Ala Ala Val Tyr Tyr Cys Gln Gln Trp Ser
            225                     230                 235                 240

Ser Asn Pro Phe Thr Phe Gly Cys Gly Thr Lys Leu Glu Ile Lys
                                245                 250                 255

<210> SEQ ID NO 23
<211> LENGTH: 255
<212> TYPE: PRT
<213> ORGANISM: Artificial Sequence
<220> FEATURE:
<223> OTHER INFORMATION: VCD3-H3L1

<400> SEQUENCE: 23

Gln Val Gln Leu Val Gln Ser Gly Ala Glu Val Lys Lys Pro Gly Ala
            1               5                   10                  15

Ser Val Lys Val Ser Cys Lys Ala Ser Gly Tyr Thr Phe Thr Arg Tyr
                        20                  25                  30

Thr Met His Trp Val Arg Gln Ser Pro Gly Gln Gly Leu Glu Trp Met
                        35                  40                  45

Gly Tyr Ile Asn Pro Ser Arg Gly Tyr Thr Asn Tyr Asn Gln Lys Phe
                        50                  55                  60

Gln Gly Arg Val Thr Met Thr Thr Asp Lys Ser Thr Ser Thr Ala Tyr
            65                      70                  75                  80

Met Glu Leu Ser Ser Leu Arg Ser Glu Asp Thr Ala Val Tyr Tyr Cys
                                85                  90                  95

Ala Arg Tyr Tyr Asp Asp His Tyr Ser Leu Asp Tyr Trp Gly Gln Gly
                                100                 105                 110

Thr Thr Val Thr Val Ser Ser Gly Gly Gly Gly Ser Gly Gly Gly Gly
```

|     |     |     |     |     |     |     |     |     |     |     |
| --- | --- | --- | --- | --- | --- | --- | --- | --- | --- | --- |
|     |     | 115 |     |     |     | 120 |     |     |     | 125 |

Ser Gly Gly Gly Ser Gly Gly Gly Ser Gly Gly Gly Ser
            130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Gln Ala Ser Ser
                165                 170                 175

Ser Val Ser Tyr Met Asn Trp Tyr Gln Gln Lys Pro Gly Lys Ala Pro
            180                 185                 190

Lys Arg Trp Ile Tyr Asp Thr Ser Lys Leu Ala Ser Gly Val Pro Ser
            195                 200                 205

Arg Phe Ser Gly Ser Gly Ser Gly Thr Asp Tyr Thr Phe Thr Ile Ser
            210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Gln Gly Thr Lys Leu Glu Ile Lys
                245                 250                 255

<210> SEQ ID NO 24
<211> LENGTH: 255
<212> TYPE: PRT
<213> ORGANISM: Artificial Sequence
<220> FEATURE:
<223> OTHER INFORMATION: VCD3-H3L1-DS

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ser Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Gly Ser Gly Gly Gly Gly
            115                 120                 125

Ser Gly Gly Gly Gly Ser Gly Gly Gly Gly Ser Gly Gly Gly Gly Ser
            130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Gln Ala Ser Ser
                165                 170                 175

Ser Val Ser Tyr Met Asn Trp Tyr Gln Gln Lys Pro Gly Lys Ala Pro
            180                 185                 190

Lys Arg Trp Ile Tyr Asp Thr Ser Lys Leu Ala Ser Gly Val Pro Ser
            195                 200                 205

Arg Phe Ser Gly Ser Gly Ser Gly Thr Asp Tyr Thr Phe Thr Ile Ser
            210                 215                 220

Ser Leu Gln Pro Glu Asp Ile Ala Thr Tyr Tyr Cys Gln Gln Trp Ser

```
                225                 230                 235                 240
Ser Asn Pro Phe Thr Phe Gly Cys Gly Thr Lys Leu Glu Ile Lys
                245                 250                 255
```

<210> SEQ ID NO 25
<211> LENGTH: 255
<212> TYPE: PRT
<213> ORGANISM: Artificial Sequence
<220> FEATURE:
<223> OTHER INFORMATION: VCD3-H3L2

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ser Pro Gly Gln Gly Leu Glu Trp Met
            35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
                100                 105                 110

Thr Thr Val Thr Val Ser Ser Gly Gly Gly Gly Ser Gly Gly Gly Gly
            115                 120                 125

Ser Gly Gly Gly Gly Ser Gly Gly Gly Gly Ser Gly Gly Gly Gly Ser
        130                 135                 140

Gly Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
                180                 185                 190

Arg Arg Leu Ile Tyr Asp Thr Ser Lys Arg Ala Thr Gly Ile Pro Ala
            195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
                245                 250                 255
```

<210> SEQ ID NO 26
<211> LENGTH: 255
<212> TYPE: PRT
<213> ORGANISM: Artificial Sequence
<220> FEATURE:
<223> OTHER INFORMATION: VCD3-H3L2-DS

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30
```

Thr Met His Trp Val Arg Gln Ser Pro Gly Gln Cys Leu Glu Trp Met
        35                  40                  45

Gly Tyr Ile Asn Pro Ser Arg Gly Tyr Thr Asn Tyr Asn Gln Lys Phe
 50                  55                  60

Gln Gly Arg Val Thr Met Thr Thr Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Tyr Asp Asp His Tyr Ser Leu Asp Tyr Trp Gly Gln Gly
                100                 105                 110

Thr Thr Val Thr Val Ser Ser Gly Gly Gly Ser Gly Gly Gly Gly
                115                 120                 125

Ser Gly Gly Gly Gly Ser Gly Gly Gly Ser Gly Gly Gly Ser
        130                 135                 140

Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
                180                 185                 190

Arg Arg Leu Ile Tyr Asp Thr Ser Lys Arg Ala Thr Gly Ile Pro Ala
                195                 200                 205

Arg Phe Ser Gly Ser Gly Ser Gly Thr Asp Tyr Thr Leu Thr Ile Ser
        210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Cys Gly Thr Lys Leu Glu Ile Lys
                245                 250                 255

<210> SEQ ID NO 27
<211> LENGTH: 255
<212> TYPE: PRT
<213> ORGANISM: Artificial Sequence
<220> FEATURE:
<223> OTHER INFORMATION: VCD3-H3L3

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ser Pro Gly Gln Gly Leu Glu Trp Met
        35                  40                  45

Gly Tyr Ile Asn Pro Ser Arg Gly Tyr Thr Asn Tyr Asn Gln Lys Phe
 50                  55                  60

Gln Gly Arg Val Thr Met Thr Thr Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Tyr Asp Asp His Tyr Ser Leu Asp Tyr Trp Gly Gln Gly
                100                 105                 110

Thr Thr Val Thr Val Ser Ser Gly Gly Gly Gly Ser Gly Gly Gly Gly
                115                 120                 125

Ser Gly Gly Gly Gly Ser Gly Gly Gly Gly Ser Gly Gly Gly Gly Ser
        130                 135                 140

Gly Gly Gly Gly Ser Glu Ile Gln Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Trp Ile Tyr Asp Thr Ser Lys Leu Ala Thr Gly Ile Pro Ala
        195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
                245                 250                 255

<210> SEQ ID NO 28
<211> LENGTH: 255
<212> TYPE: PRT
<213> ORGANISM: Artificial Sequence
<220> FEATURE:
<223> OTHER INFORMATION: VCD3-H3L3-DS

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ser Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Glu Ile Gln Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Trp Ile Tyr Asp Thr Ser Lys Leu Ala Thr Gly Ile Pro Ala
        195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Cys Gly Thr Lys Leu Glu Ile Lys
                245                 250                 255

<210> SEQ ID NO 29
<211> LENGTH: 117
<212> TYPE: PRT
<213> ORGANISM: Artificial Sequence
<220> FEATURE:
<223> OTHER INFORMATION: mBasil VH

<400> SEQUENCE: 29

```
Gln Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Arg Tyr
            20                  25                  30

Trp Met His Trp Ile Lys Gln Arg Pro Gly Gln Gly Leu Glu Trp Ile
        35                  40                  45

Gly Ala Ile Tyr Pro Gly Asn Ser Asp Thr Ser Tyr Asn Gln Lys Phe
    50                  55                  60

Glu Gly Lys Ala Lys Leu Thr Ala Val Thr Ser Ala Ser Thr Ala Tyr
65                  70                  75                  80

Met Glu Leu Ser Ser Leu Thr His Glu Asp Ser Ala Val Tyr Tyr Cys
                85                  90                  95

Ser Arg Asp Tyr Gly Tyr Tyr Phe Asp Phe Trp Gly Gln Gly Thr Thr
            100                 105                 110

Leu Thr Val Ser Ser
        115
```

<210> SEQ ID NO 30
<211> LENGTH: 117
<212> TYPE: PRT
<213> ORGANISM: Artificial Sequence
<220> FEATURE:
<223> OTHER INFORMATION: VCD25-H1

<400> SEQUENCE: 30

```
Gln Val Gln Leu Val Gln Ser Gly Ala Gly Val Ala Lys Pro Gly Ala
1               5                   10                  15

Ser Val Lys Val Ser Cys Lys Ala Ser Gly Tyr Ser Phe Thr Arg Tyr
            20                  25                  30

Trp Met His Trp Val Arg Gln Pro Pro Gly Gln Gly Leu Glu Trp Met
        35                  40                  45

Gly Ala Ile Tyr Pro Gly Asn Ser Asp Thr Ser Tyr Ser Gln Lys Phe
    50                  55                  60

Glu Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Asp Tyr Gly Tyr Tyr Phe Asp Phe Trp Gly Gln Gly Thr Thr
            100                 105                 110

Val Thr Val Ser Ser
        115
```

<210> SEQ ID NO 31
<211> LENGTH: 117
<212> TYPE: PRT
<213> ORGANISM: Artificial Sequence
<220> FEATURE:
<223> OTHER INFORMATION: VCD25-H2

<400> SEQUENCE: 31

```
Gln Val Gln Leu Val Gln Ser Gly Ala Glu Val Lys Lys Pro Gly Ala
```

-continued

```
                1               5                  10                  15
            Ser Val Lys Val Ser Cys Lys Ala Ser Gly Tyr Ser Phe Thr Arg Tyr
                            20                  25                  30

Trp Met His Trp Val Arg Gln Pro Gly Gln Arg Leu Glu Trp Met
                        35                  40                  45

Gly Ala Ile Tyr Pro Gly Asn Ser Asp Thr Ser Tyr Ser Gln Lys Phe
                    50                  55                  60

Glu Gly Arg Val Thr Ile Thr Ala Asp Thr Ser Ala Ser Thr Ala Tyr
             65                 70                  75                  80

Met Glu Leu Ser Ser Leu Arg Ser Glu Asp Thr Ala Val Tyr Tyr Cys
                            85                  90                  95

Ser Arg Asp Tyr Gly Tyr Tyr Phe Asp Phe Trp Gly Gln Gly Thr Thr
                            100                 105                 110

Val Thr Val Ser Ser
                    115

<210> SEQ ID NO 32
<211> LENGTH: 104
<212> TYPE: PRT
<213> ORGANISM: Artificial Sequence
<220> FEATURE:
<223> OTHER INFORMATION: mBasil VL

<400> SEQUENCE: 32

Gln Ile Val Ser Thr Gln Ser Pro Ala Ile Met Ser Ala Ser Pro Gly
             1               5                  10                  15

Glu Lys Val Thr Met Thr Cys Ser Ala Ser Ser Ser Arg Ser Tyr Met
                            20                  25                  30

Gln Trp Tyr Gln Gln Lys Pro Gly Thr Ser Pro Lys Arg Trp Ile Tyr
                        35                  40                  45

Asp Thr Ser Lys Leu Ala Ser Gly Val Pro Ala Arg Phe Ser Gly Ser
                    50                  55                  60

Gly Ser Gly Thr Ser Tyr Ser Leu Thr Ile Ser Ser Met Glu Ala Glu
             65                 70                  75                  80

Asp Ala Ala Thr Tyr Tyr Cys His Gln Arg Ser Ser Tyr Thr Phe Gly
                            85                  90                  95

Gly Gly Thr Lys Leu Glu Ile Lys
                            100

<210> SEQ ID NO 33
<211> LENGTH: 104
<212> TYPE: PRT
<213> ORGANISM: Artificial Sequence
<220> FEATURE:
<223> OTHER INFORMATION: VCD25-L1

<400> SEQUENCE: 33

Gln Ile Val Ser Thr Gln Ser Pro Asp Thr Gln Ser Val Thr Pro Lys
             1               5                  10                  15

Glu Lys Val Thr Ile Thr Cys Arg Ala Ser Ser Ser Arg Ser Tyr Met
                            20                  25                  30

Gln Trp Tyr Gln Gln Lys Pro Asp Gln Ser Pro Lys Arg Trp Ile Tyr
                        35                  40                  45

Asp Thr Ser Lys Ser Ala Ser Gly Val Pro Ala Arg Phe Ser Gly Ser
                    50                  55                  60

Gly Ser Gly Thr Asp Tyr Thr Leu Thr Ile Asn Ser Leu Glu Ala Glu
             65                 70                  75                  80
```

```
Asp Ala Ala Thr Tyr Tyr Cys His Gln Arg Ser Ser Tyr Thr Phe Gly
                85                  90                  95

Gln Gly Thr Lys Leu Glu Ile Lys
            100
```

<210> SEQ ID NO 34
<211> LENGTH: 104
<212> TYPE: PRT
<213> ORGANISM: Artificial Sequence
<220> FEATURE:
<223> OTHER INFORMATION: VCD25-L2

<400> SEQUENCE: 34

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Arg Ser Tyr Met
            20                  25                  30

Gln Trp Tyr Gln Gln Lys Pro Asp Gln Ser Pro Lys Arg Leu Ile Tyr
            35                  40                  45

Asp Thr Ser Lys Ser Ala Ser Gly Val Pro Ser Arg Phe Ser Gly Ser
        50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys His Gln Arg Ser Ser Tyr Thr Phe Gly
                85                  90                  95

Gln Gly Thr Lys Leu Glu Ile Lys
            100
```

<210> SEQ ID NO 35
<211> LENGTH: 251
<212> TYPE: PRT
<213> ORGANISM: Artificial Sequence
<220> FEATURE:
<223> OTHER INFORMATION: VCD25-H1L1

<400> SEQUENCE: 35

```
Gln Val Gln Leu Val Gln Ser Gly Ala Gly Val Ala Lys Pro Gly Ala
1               5                   10                  15

Ser Val Lys Val Ser Cys Lys Ala Ser Gly Tyr Ser Phe Thr Arg Tyr
            20                  25                  30

Trp Met His Trp Val Arg Gln Pro Pro Gly Gln Gly Leu Glu Trp Met
            35                  40                  45

Gly Ala Ile Tyr Pro Gly Asn Ser Asp Thr Ser Tyr Ser Gln Lys Phe
        50                  55                  60

Glu Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Asp Tyr Gly Tyr Tyr Phe Asp Phe Trp Gly Gln Gly Thr Thr
                100                 105                 110

Val Thr Val Ser Ser Gly Gly Gly Gly Ser Gly Gly Gly Gly Ser Gly
            115                 120                 125

Gly Gly Gly Ser Gly Gly Gly Gly Ser Gly Gly Gly Ser Gly Gly
            130                 135                 140

Gly Gly Ser Gln Ile Val Ser Thr Gln Ser Pro Asp Thr Gln Ser Val
145                 150                 155                 160

Thr Pro Lys Glu Lys Val Thr Ile Thr Cys Arg Ala Ser Ser Ser Arg
                165                 170                 175
```

```
Ser Tyr Met Gln Trp Tyr Gln Lys Pro Asp Gln Ser Pro Lys Arg
            180                 185                 190

Trp Ile Tyr Asp Thr Ser Lys Ser Ala Ser Gly Val Pro Ser Arg Phe
            195                 200                 205

Ser Gly Ser Gly Ser Gly Thr Asp Tyr Thr Leu Thr Ile Asn Ser Leu
210                 215                 220

Glu Ala Glu Asp Ala Ala Thr Tyr Tyr Cys His Gln Arg Ser Ser Tyr
225                 230                 235                 240

Thr Phe Gly Gln Gly Thr Lys Leu Glu Ile Lys
            245                 250

<210> SEQ ID NO 36
<211> LENGTH: 251
<212> TYPE: PRT
<213> ORGANISM: Artificial Sequence
<220> FEATURE:
<223> OTHER INFORMATION: VCD25-H1L1-DS

<400> SEQUENCE: 36

Gln Val Gln Leu Val Gln Ser Gly Ala Gly Val Ala Lys Pro Gly Ala
1               5                   10                  15

Ser Val Lys Val Ser Cys Lys Ala Ser Gly Tyr Ser Phe Thr Arg Tyr
            20                  25                  30

Trp Met His Trp Val Arg Gln Pro Gly Gln Gly Leu Glu Trp Met
        35                  40                  45

Gly Ala Ile Tyr Pro Gly Asn Ser Asp Thr Ser Tyr Ser Gln Lys Phe
    50                  55                  60

Glu Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Asp Tyr Gly Tyr Tyr Phe Asp Phe Trp Gly Gln Cys Thr Thr
            100                 105                 110

Val Thr Val Ser Ser Gly Gly Gly Gly Ser Gly Gly Gly Gly Ser Gly
        115                 120                 125

Gly Gly Gly Ser Gly Gly Gly Ser Gly Gly Gly Ser Gly Gly
    130                 135                 140

Gly Gly Ser Gln Ile Val Ser Thr Gln Ser Pro Asp Thr Gln Ser Val
145                 150                 155                 160

Thr Pro Lys Glu Lys Val Thr Ile Thr Cys Arg Ala Ser Ser Ser Arg
            165                 170                 175

Ser Tyr Met Gln Trp Tyr Gln Lys Pro Asp Gln Ser Pro Lys Arg
            180                 185                 190

Trp Ile Tyr Asp Thr Ser Lys Ser Ala Ser Gly Val Pro Ser Arg Phe
            195                 200                 205

Ser Gly Ser Gly Ser Gly Thr Asp Tyr Thr Leu Thr Ile Asn Ser Leu
210                 215                 220

Glu Ala Glu Asp Ala Ala Thr Tyr Tyr Cys His Gln Arg Ser Ser Tyr
225                 230                 235                 240

Thr Phe Gly Cys Gly Thr Lys Leu Glu Ile Lys
            245                 250

<210> SEQ ID NO 37
<211> LENGTH: 251
<212> TYPE: PRT
<213> ORGANISM: Artificial Sequence
```

<220> FEATURE:
<223> OTHER INFORMATION: VCD25-H1L2

<400> SEQUENCE: 37

Gln Val Gln Leu Val Gln Ser Gly Ala Gly Val Ala Lys Pro Gly Ala
1               5                   10                  15

Ser Val Lys Val Ser Cys Lys Ala Ser Gly Tyr Ser Phe Thr Arg Tyr
                20                  25                  30

Trp Met His Trp Val Arg Gln Pro Pro Gly Gln Gly Leu Glu Trp Met
            35                  40                  45

Gly Ala Ile Tyr Pro Gly Asn Ser Asp Thr Ser Tyr Ser Gln Lys Phe
50                  55                  60

Glu Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Asp Tyr Gly Tyr Tyr Phe Asp Phe Trp Gly Gln Gly Thr Thr
                100                 105                 110

Val Thr Val Ser Ser Gly Gly Gly Gly Ser Gly Gly Gly Gly Ser Gly
            115                 120                 125

Gly Gly Ser Gly Gly Gly Ser Gly Gly Gly Gly Ser Gly Gly
        130                 135                 140

Gly Gly Ser Glu Ile Val Leu Thr Gln Ser Pro Asp Phe Gln Ser Val
145                 150                 155                 160

Thr Pro Lys Glu Lys Val Thr Ile Thr Cys Arg Ala Ser Ser Ser Arg
                165                 170                 175

Ser Tyr Met Gln Trp Tyr Gln Gln Lys Pro Asp Gln Ser Pro Lys Arg
                180                 185                 190

Leu Ile Tyr Asp Thr Ser Lys Ser Ala Ser Gly Val Pro Ser Arg Phe
            195                 200                 205

Ser Gly Ser Gly Ser Gly Thr Asp Tyr Thr Leu Thr Ile Asn Ser Leu
210                 215                 220

Glu Ala Glu Asp Ala Ala Thr Tyr Tyr Cys His Gln Arg Ser Ser Tyr
225                 230                 235                 240

Thr Phe Gly Gln Gly Thr Lys Leu Glu Ile Lys
                245                 250

<210> SEQ ID NO 38
<211> LENGTH: 251
<212> TYPE: PRT
<213> ORGANISM: Artificial Sequence
<220> FEATURE:
<223> OTHER INFORMATION: VCD25-H1L2-DS

<400> SEQUENCE: 38

Gln Val Gln Leu Val Gln Ser Gly Ala Gly Val Ala Lys Pro Gly Ala
1               5                   10                  15

Ser Val Lys Val Ser Cys Lys Ala Ser Gly Tyr Ser Phe Thr Arg Tyr
                20                  25                  30

Trp Met His Trp Val Arg Gln Pro Pro Gly Gln Cys Leu Glu Trp Met
            35                  40                  45

Gly Ala Ile Tyr Pro Gly Asn Ser Asp Thr Ser Tyr Ser Gln Lys Phe
50                  55                  60

Glu Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys

-continued

```
                85                  90                  95
Ser Arg Asp Tyr Gly Tyr Tyr Phe Asp Phe Trp Gly Gln Gly Thr Thr
                100                 105                 110

Val Thr Val Ser Ser Gly Gly Gly Gly Ser Gly Gly Gly Gly Ser Gly
            115                 120                 125

Gly Gly Ser Gly Gly Gly Gly Ser Gly Gly Gly Gly Ser Gly Gly
        130                 135                 140

Gly Gly Ser Glu Ile Val Leu Thr Gln Ser Pro Asp Phe Gln Ser Val
145                 150                 155                 160

Thr Pro Lys Glu Lys Val Thr Ile Thr Cys Arg Ala Ser Ser Ser Arg
                165                 170                 175

Ser Tyr Met Gln Trp Tyr Gln Gln Lys Pro Asp Gln Ser Pro Lys Arg
            180                 185                 190

Leu Ile Tyr Asp Thr Ser Lys Ser Ala Ser Gly Val Pro Ser Arg Phe
        195                 200                 205

Ser Gly Ser Gly Ser Gly Thr Asp Tyr Thr Leu Thr Ile Asn Ser Leu
    210                 215                 220

Glu Ala Glu Asp Ala Ala Thr Tyr Tyr Cys His Gln Arg Ser Ser Tyr
225                 230                 235                 240

Thr Phe Gly Cys Gly Thr Lys Leu Glu Ile Lys
                245                 250
```

<210> SEQ ID NO 39
<211> LENGTH: 251
<212> TYPE: PRT
<213> ORGANISM: Artificial Sequence
<220> FEATURE:
<223> OTHER INFORMATION: VCD25-H2L1

<400> SEQUENCE: 39

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Arg Tyr
            20                  25                  30

Trp Met His Trp Val Arg Gln Pro Gly Gln Arg Leu Glu Trp Met
        35                  40                  45

Gly Ala Ile Tyr Pro Gly Asn Ser Asp Thr Ser Tyr Ser Gln Lys Phe
    50                  55                  60

Glu Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Asp Tyr Gly Tyr Tyr Phe Asp Phe Trp Gly Gln Gly Thr Thr
                100                 105                 110

Val Thr Val Ser Ser Gly Gly Gly Gly Ser Gly Gly Gly Gly Ser Gly
            115                 120                 125

Gly Gly Gly Ser Gly Gly Gly Gly Ser Gly Gly Gly Gly Ser Gly Gly
        130                 135                 140

Gly Gly Ser Gln Ile Val Ser Thr Gln Ser Pro Asp Thr Gln Ser Val
145                 150                 155                 160

Thr Pro Lys Glu Lys Val Thr Ile Thr Cys Arg Ala Ser Ser Ser Arg
                165                 170                 175

Ser Tyr Met Gln Trp Tyr Gln Gln Lys Pro Asp Gln Ser Pro Lys Arg
            180                 185                 190

Trp Ile Tyr Asp Thr Ser Lys Ser Ala Ser Gly Val Pro Ser Arg Phe
```

```
              195                 200                 205
Ser Gly Ser Gly Ser Gly Thr Asp Tyr Thr Leu Thr Ile Asn Ser Leu
            210                 215                 220

Glu Ala Glu Asp Ala Ala Thr Tyr Tyr Cys His Gln Arg Ser Ser Tyr
225                 230                 235                 240

Thr Phe Gly Gln Gly Thr Lys Leu Glu Ile Lys
                245                 250

<210> SEQ ID NO 40
<211> LENGTH: 251
<212> TYPE: PRT
<213> ORGANISM: Artificial Sequence
<220> FEATURE:
<223> OTHER INFORMATION: VCD25-H2L1-DS

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Arg Tyr
            20                  25                  30

Trp Met His Trp Val Arg Gln Pro Gly Gln Cys Leu Glu Trp Met
        35                  40                  45

Gly Ala Ile Tyr Pro Gly Asn Ser Asp Thr Ser Tyr Ser Gln Lys Phe
    50                  55                  60

Glu Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Asp Tyr Gly Tyr Tyr Phe Asp Phe Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Gln Ile Val Ser Thr Gln Ser Pro Asp Thr Gln Ser Val
145                 150                 155                 160

Thr Pro Lys Glu Lys Val Thr Ile Thr Cys Arg Ala Ser Ser Ser Arg
                165                 170                 175

Ser Tyr Met Gln Trp Tyr Gln Leu Lys Pro Asp Gln Ser Pro Lys Arg
            180                 185                 190

Trp Ile Tyr Asp Thr Ser Lys Ser Ala Ser Gly Val Pro Ser Arg Phe
        195                 200                 205

Ser Gly Ser Gly Ser Gly Thr Asp Tyr Thr Leu Thr Ile Asn Ser Leu
    210                 215                 220

Glu Ala Glu Asp Ala Ala Thr Tyr Tyr Cys His Gln Arg Ser Ser Tyr
225                 230                 235                 240

Thr Phe Gly Cys Gly Thr Lys Leu Glu Ile Lys
                245                 250

<210> SEQ ID NO 41
<211> LENGTH: 251
<212> TYPE: PRT
<213> ORGANISM: Artificial Sequence
<220> FEATURE:
<223> OTHER INFORMATION: VCD25-H2L2

<400> SEQUENCE: 41
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Arg Tyr
            20                  25                  30

Trp Met His Trp Val Arg Gln Pro Pro Gly Gln Arg Leu Glu Trp Met
        35                  40                  45

Gly Ala Ile Tyr Pro Gly Asn Ser Asp Thr Ser Tyr Ser Gln Lys Phe
    50                  55                  60

Glu Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Asp Tyr Gly Tyr Tyr Phe Asp Phe Trp Gly Gln Gly Thr Thr
            100                 105                 110

Val Thr Val Ser Ser Gly Gly Gly Ser Gly Gly Gly Gly Ser Gly
        115                 120                 125

Gly Gly Gly Ser Gly Gly Gly Gly Ser Gly Gly Gly Ser Gly Gly
        130                 135                 140

Gly Gly Ser Glu Ile Val Leu Thr Gln Ser Pro Asp Phe Gln Ser Val
145                 150                 155                 160

Thr Pro Lys Glu Lys Val Thr Ile Thr Cys Arg Ala Ser Ser Ser Arg
            165                 170                 175

Ser Tyr Met Gln Trp Tyr Gln Gln Lys Pro Asp Gln Ser Pro Lys Arg
            180                 185                 190

Leu Ile Tyr Asp Thr Ser Lys Ser Ala Ser Gly Val Pro Ser Arg Phe
        195                 200                 205

Ser Gly Ser Gly Ser Gly Thr Asp Tyr Thr Leu Thr Ile Asn Ser Leu
        210                 215                 220

Glu Ala Glu Asp Ala Ala Thr Tyr Tyr Cys His Gln Arg Ser Ser Tyr
225                 230                 235                 240

Thr Phe Gly Gln Gly Thr Lys Leu Glu Ile Lys
            245                 250

<210> SEQ ID NO 42
<211> LENGTH: 251
<212> TYPE: PRT
<213> ORGANISM: Artificial Sequence
<220> FEATURE:
<223> OTHER INFORMATION: VCD25-H2L2-DS

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Arg Tyr
            20                  25                  30

Trp Met His Trp Val Arg Gln Pro Pro Gly Gln Cys Leu Glu Trp Met
        35                  40                  45

Gly Ala Ile Tyr Pro Gly Asn Ser Asp Thr Ser Tyr Ser Gln Lys Phe
    50                  55                  60

Glu Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Asp Tyr Gly Tyr Tyr Phe Asp Phe Trp Gly Gln Gly Thr Thr
            100                 105                 110

```
Val Thr Val Ser Ser Gly Gly Gly Ser Gly Gly Gly Ser Gly
        115                 120                 125

Gly Gly Gly Ser Gly Gly Gly Ser Gly Gly Gly Ser Gly Gly
    130                 135                 140

Gly Gly Ser Glu Ile Val Leu Thr Gln Ser Pro Asp Phe Gln Ser Val
145                 150                 155                 160

Thr Pro Lys Glu Lys Val Thr Ile Thr Cys Arg Ala Ser Ser Ser Arg
                165                 170                 175

Ser Tyr Met Gln Trp Tyr Gln Gln Lys Pro Asp Gln Ser Pro Lys Arg
            180                 185                 190

Leu Ile Tyr Asp Thr Ser Lys Ser Ala Ser Gly Val Pro Ser Arg Phe
        195                 200                 205

Ser Gly Ser Gly Ser Gly Thr Asp Tyr Thr Leu Thr Ile Asn Ser Leu
    210                 215                 220

Glu Ala Glu Asp Ala Ala Thr Tyr Tyr Cys His Gln Arg Ser Ser Tyr
225                 230                 235                 240

Thr Phe Gly Cys Gly Thr Lys Leu Glu Ile Lys
                245                 250

<210> SEQ ID NO 43
<211> LENGTH: 251
<212> TYPE: PRT
<213> ORGANISM: Artificial Sequence
<220> FEATURE:
<223> OTHER INFORMATION: VCD25-L1H1

<400> SEQUENCE: 43

Gln Ile Val Ser Thr Gln Ser Pro Asp Thr Gln Ser Val Thr Pro Lys
1               5                   10                  15

Glu Lys Val Thr Ile Thr Cys Arg Ala Ser Ser Ser Arg Ser Tyr Met
                20                  25                  30

Gln Trp Tyr Gln Gln Lys Pro Asp Gln Ser Pro Lys Arg Trp Ile Tyr
            35                  40                  45

Asp Thr Ser Lys Ser Ala Ser Gly Val Pro Ser Arg Phe Ser Gly Ser
        50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys His Gln Arg Ser Ser Tyr Thr Phe Gly
                85                  90                  95

Gln Gly Thr Lys Leu Glu Ile Lys Gly Gly Gly Ser Gly Gly Gly
            100                 105                 110

Gly Ser Gly Gly Gly Ser Gly Gly Gly Ser Gly Gly Gly Gly
        115                 120                 125

Ser Gly Gly Gly Ser Gln Val Gln Leu Val Gln Ser Gly Ala Gly
    130                 135                 140

Val Ala Lys Pro Gly Ala Ser Val Lys Val Ser Cys Lys Ala Ser Gly
145                 150                 155                 160

Tyr Ser Phe Thr Arg Tyr Trp Met His Trp Val Arg Gln Pro Pro Gly
                165                 170                 175

Gln Gly Leu Glu Trp Met Gly Ala Ile Tyr Pro Gly Asn Ser Asp Thr
            180                 185                 190

Ser Tyr Ser Gln Lys Phe Glu Gly Arg Val Thr Ile Thr Ala Asp Thr
        195                 200                 205

Ser Ala Ser Thr Ala Tyr Met Glu Leu Ser Ser Leu Arg Ser Glu Asp
    210                 215                 220
```

Thr Ala Val Tyr Tyr Cys Ser Arg Asp Tyr Gly Tyr Tyr Phe Asp Phe
225                 230                 235                 240

Trp Gly Gln Gly Thr Thr Val Thr Val Ser Ser
                245                 250

<210> SEQ ID NO 44
<211> LENGTH: 251
<212> TYPE: PRT
<213> ORGANISM: Artificial Sequence
<220> FEATURE:
<223> OTHER INFORMATION: VCD25-L1H1-DS

<400> SEQUENCE: 44

Gln Ile Val Ser Thr Gln Ser Pro Asp Thr Gln Ser Val Thr Pro Lys
1               5                   10                  15

Glu Lys Val Thr Ile Thr Cys Arg Ala Ser Ser Arg Ser Tyr Met
            20                  25                  30

Gln Trp Tyr Gln Gln Lys Pro Asp Gln Ser Pro Lys Arg Trp Ile Tyr
            35                  40                  45

Asp Thr Ser Lys Ser Ala Ser Gly Val Pro Ser Arg Phe Ser Gly Ser
        50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys His Gln Arg Ser Ser Tyr Thr Phe Gly
                85                  90                  95

Cys Gly Thr Lys Leu Glu Ile Lys Gly Gly Gly Ser Gly Gly Gly
            100                 105                 110

Gly Ser Gly Gly Gly Ser Gly Gly Gly Ser Gly Gly Gly
            115                 120                 125

Ser Gly Gly Gly Ser Gln Val Gln Leu Val Gln Ser Gly Ala Gly
        130                 135                 140

Val Ala Lys Pro Gly Ala Ser Val Lys Val Ser Cys Lys Ala Ser Gly
145                 150                 155                 160

Tyr Ser Phe Thr Arg Tyr Trp Met His Trp Val Arg Gln Pro Pro Gly
                165                 170                 175

Gln Cys Leu Glu Trp Met Gly Ala Ile Tyr Pro Gly Asn Ser Asp Thr
            180                 185                 190

Ser Tyr Ser Gln Lys Phe Glu Gly Arg Val Thr Ile Thr Ala Asp Thr
        195                 200                 205

Ser Ala Ser Thr Ala Tyr Met Glu Leu Ser Ser Leu Arg Ser Glu Asp
    210                 215                 220

Thr Ala Val Tyr Tyr Cys Ser Arg Asp Tyr Gly Tyr Tyr Phe Asp Phe
225                 230                 235                 240

Trp Gly Gln Gly Thr Thr Val Thr Val Ser Ser
                245                 250

<210> SEQ ID NO 45
<211> LENGTH: 251
<212> TYPE: PRT
<213> ORGANISM: Artificial Sequence
<220> FEATURE:
<223> OTHER INFORMATION: VCD25-L1H2

<400> SEQUENCE: 45

Gln Ile Val Ser Thr Gln Ser Pro Asp Thr Gln Ser Val Thr Pro Lys
1               5                   10                  15

Glu Lys Val Thr Ile Thr Cys Arg Ala Ser Ser Arg Ser Tyr Met
            20                  25                  30

```
Gln Trp Tyr Gln Gln Lys Pro Asp Gln Ser Pro Lys Arg Trp Ile Tyr
             35                  40                  45

Asp Thr Ser Lys Ser Ala Ser Gly Val Pro Ser Arg Phe Ser Gly Ser
 50                  55                  60

Gly Ser Gly Thr Asp Tyr Thr Leu Thr Ile Asn Ser Leu Glu Ala Glu
 65                  70                  75                  80

Asp Ala Ala Thr Tyr Tyr Cys His Gln Arg Ser Ser Tyr Thr Phe Gly
                 85                  90                  95

Gln Gly Thr Lys Leu Glu Ile Lys Gly Gly Gly Ser Gly Gly Gly
             100                 105                 110

Gly Ser Gly Gly Gly Ser Gly Gly Gly Ser Gly Gly Gly
         115                 120                 125

Ser Gly Gly Gly Ser Gln Val Gln Leu Val Gln Ser Gly Ala Glu
 130                 135                 140

Val Lys Lys Pro Gly Ala Ser Val Lys Val Ser Cys Lys Ala Ser Gly
 145                 150                 155                 160

Tyr Ser Phe Thr Arg Tyr Trp Met His Trp Val Arg Gln Pro Pro Gly
                 165                 170                 175

Gln Arg Leu Glu Trp Met Gly Ala Ile Tyr Pro Gly Asn Ser Asp Thr
             180                 185                 190

Ser Tyr Ser Gln Lys Phe Glu Gly Arg Val Thr Ile Thr Ala Asp Thr
             195                 200                 205

Ser Ala Ser Thr Ala Tyr Met Glu Leu Ser Ser Leu Arg Ser Glu Asp
 210                 215                 220

Thr Ala Val Tyr Tyr Cys Ser Arg Asp Tyr Gly Tyr Tyr Phe Asp Phe
225                  230                 235                 240

Trp Gly Gln Gly Thr Thr Val Thr Val Ser Ser
             245                 250

<210> SEQ ID NO 46
<211> LENGTH: 251
<212> TYPE: PRT
<213> ORGANISM: Artificial Sequence
<220> FEATURE:
<223> OTHER INFORMATION: VCD25-L1H2-DS

<400> SEQUENCE: 46

Gln Ile Val Ser Thr Gln Ser Pro Asp Thr Gln Ser Val Thr Pro Lys
 1               5                  10                  15

Glu Lys Val Thr Ile Thr Cys Arg Ala Ser Ser Ser Arg Ser Tyr Met
                 20                  25                  30

Gln Trp Tyr Gln Gln Lys Pro Asp Gln Ser Pro Lys Arg Trp Ile Tyr
             35                  40                  45

Asp Thr Ser Lys Ser Ala Ser Gly Val Pro Ser Arg Phe Ser Gly Ser
 50                  55                  60

Gly Ser Gly Thr Asp Tyr Thr Leu Thr Ile Asn Ser Leu Glu Ala Glu
 65                  70                  75                  80

Asp Ala Ala Thr Tyr Tyr Cys His Gln Arg Ser Ser Tyr Thr Phe Gly
                 85                  90                  95

Cys Gly Thr Lys Leu Glu Ile Lys Gly Gly Gly Ser Gly Gly Gly
             100                 105                 110

Gly Ser Gly Gly Gly Ser Gly Gly Gly Ser Gly Gly Gly
         115                 120                 125

Ser Gly Gly Gly Ser Gln Val Gln Leu Val Gln Ser Gly Ala Glu
 130                 135                 140
```

```
Val Lys Lys Pro Gly Ala Ser Val Lys Val Ser Cys Lys Ala Ser Gly
145                 150                 155                 160

Tyr Ser Phe Thr Arg Tyr Trp Met His Trp Val Arg Gln Pro Pro Gly
                165                 170                 175

Gln Arg Leu Glu Trp Met Gly Ala Ile Tyr Pro Gly Asn Ser Asp Thr
            180                 185                 190

Ser Tyr Ser Gln Lys Phe Glu Gly Arg Val Thr Ile Thr Ala Asp Thr
        195                 200                 205

Ser Ala Ser Thr Ala Tyr Met Glu Leu Ser Ser Leu Arg Ser Glu Asp
    210                 215                 220

Thr Ala Val Tyr Tyr Cys Ser Arg Asp Tyr Gly Tyr Tyr Phe Asp Phe
225                 230                 235                 240

Trp Gly Gln Cys Thr Thr Val Thr Val Ser Ser
                245                 250
```

<210> SEQ ID NO 47
<211> LENGTH: 251
<212> TYPE: PRT
<213> ORGANISM: Artificial Sequence
<220> FEATURE:
<223> OTHER INFORMATION: VCD25-L2H1

<400> SEQUENCE: 47

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Ser Arg Ser Tyr Met
            20                  25                  30

Gln Trp Tyr Gln Gln Lys Pro Asp Gln Ser Pro Lys Arg Leu Ile Tyr
        35                  40                  45

Asp Thr Ser Lys Ser Ala Ser Gly Val Pro Ser Arg Phe Ser Gly Ser
    50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys His Gln Arg Ser Ser Tyr Thr Phe Gly
                85                  90                  95

Gln Gly Thr Lys Leu Glu Ile Lys Gly Gly Gly Ser Gly Gly Gly Gly
            100                 105                 110

Gly Ser Gly Gly Gly Gly Ser Gly Gly Gly Ser Gly Gly Gly Gly
        115                 120                 125

Ser Gly Gly Gly Gly Ser Gln Val Gln Leu Val Gln Ser Gly Ala Gly
    130                 135                 140

Val Ala Lys Pro Gly Ala Ser Val Lys Val Ser Cys Lys Ala Ser Gly
145                 150                 155                 160

Tyr Ser Phe Thr Arg Tyr Trp Met His Trp Val Arg Gln Pro Pro Gly
                165                 170                 175

Gln Gly Leu Glu Trp Met Gly Ala Ile Tyr Pro Gly Asn Ser Asp Thr
            180                 185                 190

Ser Tyr Ser Gln Lys Phe Glu Gly Arg Val Thr Ile Thr Ala Asp Thr
        195                 200                 205

Ser Ala Ser Thr Ala Tyr Met Glu Leu Ser Ser Leu Arg Ser Glu Asp
    210                 215                 220

Thr Ala Val Tyr Tyr Cys Ser Arg Asp Tyr Gly Tyr Tyr Phe Asp Phe
225                 230                 235                 240

Trp Gly Gln Gly Thr Thr Val Thr Val Ser Ser
                245                 250
```

```
<210> SEQ ID NO 48
<211> LENGTH: 251
<212> TYPE: PRT
<213> ORGANISM: Artificial Sequence
<220> FEATURE:
<223> OTHER INFORMATION: VCD25-L2H1-DS

<400> SEQUENCE: 48

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Ser Arg Ser Tyr Met
                20                  25                  30

Gln Trp Tyr Gln Gln Lys Pro Asp Gln Ser Pro Lys Arg Leu Ile Tyr
            35                  40                  45

Asp Thr Ser Lys Ser Ala Ser Gly Val Pro Ser Arg Phe Ser Gly Ser
        50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys His Gln Arg Ser Ser Tyr Thr Phe Gly
                85                  90                  95

Cys Gly Thr Lys Leu Glu Ile Lys Gly Gly Gly Ser Gly Gly Gly
                100                 105                 110

Gly Ser Gly Gly Gly Gly Ser Gly Gly Gly Ser Gly Gly Gly Gly
            115                 120                 125

Ser Gly Gly Gly Gly Ser Gln Val Gln Leu Val Gln Ser Gly Ala Gly
        130                 135                 140

Val Ala Lys Pro Gly Ala Ser Val Lys Val Ser Cys Lys Ala Ser Gly
145                 150                 155                 160

Tyr Ser Phe Thr Arg Tyr Trp Met His Trp Val Arg Gln Pro Pro Gly
                165                 170                 175

Gln Gly Leu Glu Trp Met Gly Ala Ile Tyr Pro Gly Asn Ser Asp Thr
            180                 185                 190

Ser Tyr Ser Gln Lys Phe Glu Gly Arg Val Thr Ile Thr Ala Asp Thr
        195                 200                 205

Ser Ala Ser Thr Ala Tyr Met Glu Leu Ser Ser Leu Arg Ser Glu Asp
    210                 215                 220

Thr Ala Val Tyr Tyr Cys Ser Arg Asp Tyr Gly Tyr Tyr Phe Asp Phe
225                 230                 235                 240

Trp Gly Gln Cys Thr Thr Val Thr Val Ser Ser
                245                 250

<210> SEQ ID NO 49
<211> LENGTH: 251
<212> TYPE: PRT
<213> ORGANISM: Artificial Sequence
<220> FEATURE:
<223> OTHER INFORMATION: VCD25-L2H2

<400> SEQUENCE: 49

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Ser Arg Ser Tyr Met
                20                  25                  30

Gln Trp Tyr Gln Gln Lys Pro Asp Gln Ser Pro Lys Arg Leu Ile Tyr
            35                  40                  45

Asp Thr Ser Lys Ser Ala Ser Gly Val Pro Ser Arg Phe Ser Gly Ser
```

```
            50                  55                  60
Gly Ser Gly Thr Asp Tyr Thr Leu Thr Ile Asn Ser Leu Glu Ala Glu
 65                  70                  75                  80

Asp Ala Ala Thr Tyr Tyr Cys His Gln Arg Ser Ser Tyr Thr Phe Gly
                 85                  90                  95

Gln Gly Thr Lys Leu Glu Ile Lys Gly Gly Gly Ser Gly Gly Gly
            100                 105                 110

Gly Ser Gly Gly Gly Ser Gly Gly Gly Ser Gly Gly Gly
            115                 120                 125

Ser Gly Gly Gly Ser Gln Val Gln Leu Val Gln Ser Gly Ala Glu
            130                 135                 140

Val Lys Lys Pro Gly Ala Ser Val Lys Val Ser Cys Lys Ala Ser Gly
145                 150                 155                 160

Tyr Ser Phe Thr Arg Tyr Trp Met His Trp Val Arg Gln Pro Pro Gly
                165                 170                 175

Gln Arg Leu Glu Trp Met Gly Ala Ile Tyr Pro Gly Asn Ser Asp Thr
            180                 185                 190

Ser Tyr Ser Gln Lys Phe Glu Gly Arg Val Thr Ile Thr Ala Asp Thr
            195                 200                 205

Ser Ala Ser Thr Ala Tyr Met Glu Leu Ser Ser Leu Arg Ser Glu Asp
210                 215                 220

Thr Ala Val Tyr Tyr Cys Ser Arg Asp Tyr Gly Tyr Tyr Phe Asp Phe
225                 230                 235                 240

Trp Gly Gln Gly Thr Thr Val Thr Val Ser Ser
                245                 250
```

<210> SEQ ID NO 50
<211> LENGTH: 251
<212> TYPE: PRT
<213> ORGANISM: Artificial Sequence
<220> FEATURE:
<223> OTHER INFORMATION: VCD25-L2H2-DS

<400> SEQUENCE: 50

```
Glu Ile Val Leu Thr Gln Ser Pro Asp Phe Gln Ser Val Thr Pro Lys
 1               5                  10                  15

Glu Lys Val Thr Ile Thr Cys Arg Ala Ser Ser Ser Arg Ser Tyr Met
            20                  25                  30

Gln Trp Tyr Gln Gln Lys Pro Asp Gln Ser Pro Lys Arg Leu Ile Tyr
         35                  40                  45

Asp Thr Ser Lys Ser Ala Ser Gly Val Pro Ser Arg Phe Ser Gly Ser
 50                  55                  60

Gly Ser Gly Thr Asp Tyr Thr Leu Thr Ile Asn Ser Leu Glu Ala Glu
 65                  70                  75                  80

Asp Ala Ala Thr Tyr Tyr Cys His Gln Arg Ser Ser Tyr Thr Phe Gly
                 85                  90                  95

Cys Gly Thr Lys Leu Glu Ile Lys Gly Gly Gly Ser Gly Gly Gly
            100                 105                 110

Gly Ser Gly Gly Gly Ser Gly Gly Gly Ser Gly Gly Gly
            115                 120                 125

Ser Gly Gly Gly Ser Gln Val Gln Leu Val Gln Ser Gly Ala Glu
            130                 135                 140

Val Lys Lys Pro Gly Ala Ser Val Lys Val Ser Cys Lys Ala Ser Gly
145                 150                 155                 160

Tyr Ser Phe Thr Arg Tyr Trp Met His Trp Val Arg Gln Pro Pro Gly
```

```
                    165                 170                 175
Gln Arg Leu Glu Trp Met Gly Ala Ile Tyr Pro Gly Asn Ser Asp Thr
                180                 185                 190

Ser Tyr Ser Gln Lys Phe Glu Gly Arg Val Thr Ile Thr Ala Asp Thr
            195                 200                 205

Ser Ala Ser Thr Ala Tyr Met Glu Leu Ser Ser Leu Arg Ser Glu Asp
        210                 215                 220

Thr Ala Val Tyr Tyr Cys Ser Arg Asp Tyr Gly Tyr Tyr Phe Asp Phe
225                 230                 235                 240

Trp Gly Gln Cys Thr Thr Val Thr Val Ser Ser
                245                 250

<210> SEQ ID NO 51
<211> LENGTH: 330
<212> TYPE: PRT
<213> ORGANISM: Homo Sapiens

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 52
<211> LENGTH: 327
<212> TYPE: PRT
<213> ORGANISM: Homo Sapiens

<400> SEQUENCE: 52

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325
```

<210> SEQ ID NO 53
<211> LENGTH: 327
<212> TYPE: PRT
<213> ORGANISM: Artificial Sequence
<220> FEATURE:
<223> OTHER INFORMATION: V-IGG4-A

<400> SEQUENCE: 53

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Ala Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 54
<211> LENGTH: 242
<212> TYPE: PRT
<213> ORGANISM: Artificial Sequence
<220> FEATURE:
<223> OTHER INFORMATION: V-IGG4-A-Fc

<400> SEQUENCE: 54

Gly Gly Gly Gly Ser Gly Gly Gly Ser Gly Gly Gly Ser Lys
1               5                   10                  15

Tyr Gly Pro Pro Cys Pro Pro Cys Pro Ala Pro Glu Ala Ala Gly Gly
            20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser Gln Glu
50                  55                  60

Asp Pro Glu Val Gln Phe Asn Trp Tyr Val Asp Gly Val Glu Val His
65                  70                  75                  80

Asn Ala Lys Thr Lys Pro Arg Glu Glu Gln Phe Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Ala Val Ser Asn Lys Gly Leu Pro Ser Ser Ile Glu
            115                 120                 125

Lys Thr Ile Ser Lys Ala Lys Gly Gln Pro Arg Glu Pro Gln Val Tyr
130                 135                 140

Thr Leu Pro Pro Ser Gln Glu Glu Met Thr Lys Asn Gln Val Ser Leu
145                 150                 155                 160

Thr Cys Leu Val Lys Gly Phe Tyr Pro Ser Asp Ile Ala Val Glu Trp
            165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Arg Leu Thr Val Asp
            195                 200                 205

Lys Ser Arg Trp Gln Glu Gly Asn Val Phe Ser Cys Ser Val Met His
            210                 215                 220

Glu Ala Leu His Asn His Tyr Thr Gln Lys Ser Leu Ser Leu Ser Leu
225                 230                 235                 240

Gly Lys

<210> SEQ ID NO 55
<211> LENGTH: 327
<212> TYPE: PRT
<213> ORGANISM: Artificial Sequence
<220> FEATURE:
<223> OTHER INFORMATION: V-IGG4-B

<400> SEQUENCE: 55

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

```
Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Ala Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Leu Leu Tyr Ser
            275                 280                 285

Lys Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 56
<211> LENGTH: 242
<212> TYPE: PRT
<213> ORGANISM: Artificial Sequence
<220> FEATURE:
<223> OTHER INFORMATION: V-IGG4-B-Fc

<400> SEQUENCE: 56

Gly Gly Gly Gly Ser Gly Gly Gly Ser Gly Gly Gly Gly Ser Lys
1               5                   10                  15

Tyr Gly Pro Pro Cys Pro Pro Cys Pro Ala Pro Glu Ala Ala Gly Gly
            20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser Gln Glu
        50                  55                  60

Asp Pro Glu Val Gln Phe Asn Trp Tyr Val Asp Gly Val Glu Val His
65                  70                  75                  80

Asn Ala Lys Thr Lys Pro Arg Glu Glu Gln Phe Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Ala Val Ser Asn Lys Gly Leu Pro Ser Ser Ile Glu
        115                 120                 125
```

```
Lys Thr Ile Ser Lys Ala Lys Gly Gln Pro Arg Glu Pro Gln Val Tyr
            130                 135                 140
Thr Leu Pro Pro Ser Gln Glu Glu Met Thr Lys Asn Gln Val Ser Leu
145                 150                 155                 160
Thr Cys Leu Val Lys Gly Phe Tyr Pro Ser Asp Ile Ala Val Glu Trp
                165                 170                 175
Glu Ser Asn Gly Gln Pro Glu Asn Asn Tyr Lys Thr Thr Pro Pro Val
            180                 185                 190
Leu Asp Ser Asp Gly Ser Phe Leu Leu Tyr Ser Lys Leu Thr Val Asp
            195                 200                 205
Lys Ser Arg Trp Gln Glu Gly Asn Val Phe Ser Cys Ser Val Met His
            210                 215                 220
Glu Ala Leu His Asn His Tyr Thr Gln Lys Ser Leu Ser Leu Ser Leu
225                 230                 235                 240
Gly Lys

<210> SEQ ID NO 57
<211> LENGTH: 326
<212> TYPE: PRT
<213> ORGANISM: Homo Sapiens

<400> SEQUENCE: 57

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
            115                 120                 125
Thr Leu Met Ile Ser Arg Thr Pro Glu Val Thr Cys Val Val Val Asp
130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
            195                 200                 205
Ala Pro Ile Glu Lys Thr Ile Ser Lys Thr Lys Gly Gln Pro Arg Glu
            210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
```

```
Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 58
<211> LENGTH: 327
<212> TYPE: PRT
<213> ORGANISM: Artificial Sequence
<220> FEATURE:
<223> OTHER INFORMATION: V-IGG2

<400> SEQUENCE: 58

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Asp Lys Thr His Thr Cys Pro Pro Cys Pro Ala
            100                 105                 110

Pro Pro Ala Ala Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Phe Arg Val Val Ser Val Leu Thr Val Val His Gln Asp
            180                 185                 190

Trp Leu Asn Gly Lys Glu Tyr Lys Cys Ala Val Ser Asn Lys Gly Leu
        195                 200                 205

Pro Ala Pro Ile Glu Lys Thr Ile Ser Lys Thr Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ser Val Glu Trp Glu Ser Asn Gly Gln Pro Glu Asn Asn Tyr Lys
            260                 265                 270

Thr Thr Pro Pro Met Leu Asp Ser Asp Gly Ser Phe Phe Leu Tyr Ser
        275                 280                 285
```

```
Lys Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro Gly Lys
                325
```

<210> SEQ ID NO 59
<211> LENGTH: 241
<212> TYPE: PRT
<213> ORGANISM: Artificial Sequence
<220> FEATURE:
<223> OTHER INFORMATION: V-IGG2-Fc

<400> SEQUENCE: 59

```
Gly Gly Gly Gly Ser Gly Gly Gly Ser Gly Gly Gly Gly Ser Asp
1               5                   10                  15

Lys Thr His Thr Cys Pro Pro Cys Pro Ala Pro Pro Ala Ala Gly Pro
                20                  25                  30

Ser Val Phe Leu Phe Pro Pro Lys Pro Lys Asp Thr Leu Met Ile Ser
            35                  40                  45

Arg Thr Pro Glu Val Thr Cys Val Val Val Asp Val Ser His Glu Asp
        50                  55                  60

Pro Glu Val Gln Phe Asn Trp Tyr Val Asp Gly Val Glu Val His Asn
65                  70                  75                  80

Ala Lys Thr Lys Pro Arg Glu Glu Gln Phe Asn Ser Thr Phe Arg Val
                85                  90                  95

Val Ser Val Leu Thr Val Val His Gln Asp Trp Leu Asn Gly Lys Glu
            100                 105                 110

Tyr Lys Cys Ala Val Ser Asn Lys Gly Leu Pro Ala Pro Ile Glu Lys
        115                 120                 125

Thr Ile Ser Lys Thr Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ser Val Glu Trp Glu
                165                 170                 175

Ser Asn Gly Gln Pro Glu Asn Asn Tyr Lys Thr Thr Pro Pro Met Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys
```

<210> SEQ ID NO 60
<211> LENGTH: 327
<212> TYPE: PRT
<213> ORGANISM: Artificial Sequence
<220> FEATURE:
<223> OTHER INFORMATION: V-IGG2-A

<400> SEQUENCE: 60

```
Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                 85                  90                  95

Thr Val Glu Arg Lys Asp Lys Thr His Thr Cys Pro Pro Cys Pro Ala
            100                 105                 110

Pro Pro Ala Ala Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Phe Arg Val Val Ser Val Leu Thr Val Val His Gln Asp
            180                 185                 190

Trp Leu Asn Gly Lys Glu Tyr Lys Cys Ala Val Ser Asn Lys Gly Leu
        195                 200                 205

Pro Ala Pro Ile Glu Lys Thr Ile Ser Lys Thr Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ser Val Glu Trp Glu Ser Asn Gly Gln Pro Glu Asn Asn Tyr Lys
            260                 265                 270

Thr Thr Pro Pro Met Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 61
<211> LENGTH: 241
<212> TYPE: PRT
<213> ORGANISM: Artificial Sequence
<220> FEATURE:
<223> OTHER INFORMATION: V-IGG2-A-Fc

<400> SEQUENCE: 61

Gly Gly Gly Gly Ser Gly Gly Gly Ser Gly Gly Gly Ser Asp
1               5                   10                  15

Lys Thr His Thr Cys Pro Pro Cys Pro Ala Pro Pro Ala Ala Gly Pro
            20                  25                  30

Ser Val Phe Leu Phe Pro Pro Lys Pro Lys Asp Thr Leu Met Ile Ser
        35                  40                  45
```

```
Arg Thr Pro Glu Val Thr Cys Val Val Val Asp Val Ser His Glu Asp
 50                  55                  60

Pro Glu Val Gln Phe Asn Trp Tyr Val Asp Gly Val Glu Val His Asn
 65                  70                  75                  80

Ala Lys Thr Lys Pro Arg Glu Glu Gln Phe Asn Ser Thr Phe Arg Val
                 85                  90                  95

Val Ser Val Leu Thr Val Val His Gln Asp Trp Leu Asn Gly Lys Glu
            100                 105                 110

Tyr Lys Cys Ala Val Ser Asn Lys Gly Leu Pro Ala Pro Ile Glu Lys
            115                 120                 125

Thr Ile Ser Lys Thr Lys Gly Gln Pro Arg Glu Pro Gln Val Tyr Thr
        130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ser Val Glu Trp Glu
                165                 170                 175

Ser Asn Gly Gln Pro Glu Asn Asn Tyr Lys Thr Thr Pro Pro Met Leu
            180                 185                 190

Asp Ser Asp Gly Ser Phe Phe Leu Tyr Ser Arg Leu Thr Val Asp Lys
            195                 200                 205

Ser Arg Trp Gln Gln Gly Asn Val Phe Ser Cys Ser Val Met His Glu
        210                 215                 220

Ala Leu His Asn His Tyr Thr Gln Lys Ser Leu Ser Leu Ser Pro Gly
225                 230                 235                 240

Lys
```

<210> SEQ ID NO 62
<211> LENGTH: 327
<212> TYPE: PRT
<213> ORGANISM: Artificial Sequence
<220> FEATURE:
<223> OTHER INFORMATION: V-IGG2-B

<400> SEQUENCE: 62

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Asp Lys Thr His Thr Cys Pro Pro Cys Pro Ala
            100                 105                 110

Pro Pro Ala Ala Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser His Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
            165                 170                 175

Asn Ser Thr Phe Arg Val Val Ser Val Leu Thr Val Val His Gln Asp
            180                 185                 190

Trp Leu Asn Gly Lys Glu Tyr Lys Cys Ala Val Ser Asn Lys Gly Leu
            195                 200                 205

Pro Ala Pro Ile Glu Lys Thr Ile Ser Lys Thr Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
            245                 250                 255

Ile Ser Val Glu Trp Glu Ser Asn Gly Gln Pro Glu Asn Asn Tyr Lys
            260                 265                 270

Thr Thr Pro Pro Met Leu Asp Ser Asp Gly Ser Phe Leu Leu Tyr Ser
            275                 280                 285

Lys Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 63
<211> LENGTH: 241
<212> TYPE: PRT
<213> ORGANISM: Artificial Sequence
<220> FEATURE:
<223> OTHER INFORMATION: V-IGG2-B-Fc

<400> SEQUENCE: 63

Gly Gly Gly Gly Ser Gly Gly Gly Ser Gly Gly Gly Ser Asp
1               5                   10                  15

Lys Thr His Thr Cys Pro Pro Cys Pro Ala Pro Ala Ala Gly Pro
            20                  25                  30

Ser Val Phe Leu Phe Pro Pro Lys Pro Lys Asp Thr Leu Met Ile Ser
            35                  40                  45

Arg Thr Pro Glu Val Thr Cys Val Val Val Asp Val Ser His Glu Asp
50                  55                  60

Pro Glu Val Gln Phe Asn Trp Tyr Val Asp Gly Val Glu Val His Asn
65                  70                  75                  80

Ala Lys Thr Lys Pro Arg Glu Glu Gln Phe Asn Ser Thr Phe Arg Val
            85                  90                  95

Val Ser Val Leu Thr Val Val His Gln Asp Trp Leu Asn Gly Lys Glu
            100                 105                 110

Tyr Lys Cys Ala Val Ser Asn Lys Gly Leu Pro Ala Pro Ile Glu Lys
            115                 120                 125

Thr Ile Ser Lys Thr Lys Gly Gln Pro Arg Glu Pro Gln Val Tyr Thr
            130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ser Val Glu Trp Glu
            165                 170                 175

Ser Asn Gly Gln Pro Glu Asn Asn Tyr Lys Thr Thr Pro Pro Met Leu
            180                 185                 190
```

```
Asp Ser Asp Gly Ser Phe Leu Leu Tyr Ser Lys Leu Thr Val Asp Lys
            195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys

<210> SEQ ID NO 64
<211> LENGTH: 326
<212> TYPE: PRT
<213> ORGANISM: Artificial Sequence
<220> FEATURE:
<223> OTHER INFORMATION: V-IGG2-C

<400> SEQUENCE: 64

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Tyr Gly Pro Pro Cys Pro Pro Cys Pro Ala Pro
            100                 105                 110

Pro Ala Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Ala Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
```

```
                            305              310              315              320
Ser Leu Ser Pro Gly Lys
                325

<210> SEQ ID NO 65
<211> LENGTH: 240
<212> TYPE: PRT
<213> ORGANISM: Artificial Sequence
<220> FEATURE:
<223> OTHER INFORMATION: V-IGG2-C-Fc

<400> SEQUENCE: 65

Gly Gly Gly Gly Ser Gly Gly Gly Ser Gly Gly Gly Gly Ser Tyr
1               5                   10                  15

Gly Pro Pro Cys Pro Pro Cys Pro Ala Pro Ala Ala Gly Pro Ser
                20                  25                  30

Val Phe Leu Phe Pro Pro Lys Pro Lys Asp Thr Leu Met Ile Ser Arg
                35                  40                  45

Thr Pro Glu Val Thr Cys Val Val Val Asp Val Ser His Glu Asp Pro
    50                  55                  60

Glu Val Gln Phe Asn Trp Tyr Val Asp Gly Val Glu Val His Asn Ala
65                  70                  75                  80

Lys Thr Lys Pro Arg Glu Glu Gln Phe Asn Ser Thr Phe Arg Val Val
                85                  90                  95

Ser Val Leu Thr Val Val His Gln Asp Trp Leu Asn Gly Lys Glu Tyr
                100                 105                 110

Lys Cys Ala Val Ser Asn Lys Gly Leu Pro Ala Pro Ile Glu Lys Thr
                115                 120                 125

Ile Ser Lys Thr Lys Gly Gln Pro Arg Glu Pro Gln Val Tyr Thr Leu
    130                 135                 140

Pro Pro Ser Arg Glu Glu Met Thr Lys Asn Gln Val Ser Leu Thr Cys
145                 150                 155                 160

Leu Val Lys Gly Phe Tyr Pro Ser Asp Ile Ser Val Glu Trp Glu Ser
                165                 170                 175

Asn Gly Gln Pro Glu Asn Asn Tyr Lys Thr Thr Pro Pro Met Leu Asp
                180                 185                 190

Ser Asp Gly Ser Phe Phe Leu Tyr Ser Lys Leu Thr Val Asp Lys Ser
                195                 200                 205

Arg Trp Gln Gln Gly Asn Val Phe Ser Cys Ser Val Met His Glu Ala
    210                 215                 220

Leu His Asn His Tyr Thr Gln Lys Ser Leu Ser Leu Ser Pro Gly Lys
225                 230                 235                 240

<210> SEQ ID NO 66
<211> LENGTH: 326
<212> TYPE: PRT
<213> ORGANISM: Artificial Sequence
<220> FEATURE:
<223> OTHER INFORMATION: V-IGG2-D

<400> SEQUENCE: 66

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45
```

-continued

```
Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Tyr Gly Pro Pro Cys Pro Cys Pro Ala Pro
            100                 105                 110

Pro Ala Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Ala Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Arg
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 67
<211> LENGTH: 240
<212> TYPE: PRT
<213> ORGANISM: Artificial Sequence
<220> FEATURE:
<223> OTHER INFORMATION: V-IGG2-D-Fc

<400> SEQUENCE: 67

Gly Gly Gly Gly Ser Gly Gly Gly Ser Gly Gly Gly Ser Tyr
 1               5                  10                  15

Gly Pro Pro Cys Pro Pro Cys Pro Ala Pro Pro Ala Ala Gly Pro Ser
                 20                  25                  30

Val Phe Leu Phe Pro Pro Lys Pro Lys Asp Thr Leu Met Ile Ser Arg
             35                  40                  45

Thr Pro Glu Val Thr Cys Val Val Val Asp Val Ser His Glu Asp Pro
 50                  55                  60

Glu Val Gln Phe Asn Trp Tyr Val Asp Gly Val Glu Val His Asn Ala
 65                  70                  75                  80
```

```
Lys Thr Lys Pro Arg Glu Glu Gln Phe Asn Ser Thr Phe Arg Val Val
            85                  90                  95

Ser Val Leu Thr Val Val His Gln Asp Trp Leu Asn Gly Lys Glu Tyr
            100                 105                 110

Lys Cys Ala Val Ser Asn Lys Gly Leu Pro Ala Pro Ile Glu Lys Thr
            115                 120                 125

Ile Ser Lys Thr Lys Gly Gln Pro Arg Glu Pro Gln Val Tyr Thr Leu
130                 135                 140

Pro Pro Ser Arg Glu Glu Met Thr Lys Asn Gln Val Ser Leu Thr Cys
145                 150                 155                 160

Leu Val Lys Gly Phe Tyr Pro Ser Asp Ile Ser Val Glu Trp Glu Ser
            165                 170                 175

Asn Gly Gln Pro Glu Asn Asn Tyr Lys Thr Thr Pro Pro Met Leu Asp
            180                 185                 190

Ser Asp Gly Ser Phe Phe Leu Tyr Ser Arg Leu Thr Val Asp Lys Ser
            195                 200                 205

Arg Trp Gln Gln Gly Asn Val Phe Ser Cys Ser Val Met His Glu Ala
            210                 215                 220

Leu His Asn His Tyr Thr Gln Lys Ser Leu Ser Leu Ser Pro Gly Lys
225                 230                 235                 240

<210> SEQ ID NO 68
<211> LENGTH: 326
<212> TYPE: PRT
<213> ORGANISM: Artificial Sequence
<220> FEATURE:
<223> OTHER INFORMATION: V-IGG2-E

<400> SEQUENCE: 68

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Tyr Gly Pro Pro Cys Pro Pro Cys Pro Ala Pro
            100                 105                 110

Pro Ala Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
            180                 185                 190

Leu Asn Gly Lys Glu Tyr Lys Cys Ala Val Ser Asn Lys Gly Leu Pro
            195                 200                 205
```

-continued

```
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Leu Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 69
<211> LENGTH: 240
<212> TYPE: PRT
<213> ORGANISM: Artificial Sequence
<220> FEATURE:
<223> OTHER INFORMATION: V-IGG2-E-Fc

<400> SEQUENCE: 69

Gly Gly Gly Gly Ser Gly Gly Gly Ser Gly Gly Gly Ser Tyr
1               5                   10                  15

Gly Pro Pro Cys Pro Pro Cys Pro Ala Pro Pro Ala Ala Gly Pro Ser
                20                  25                  30

Val Phe Leu Phe Pro Pro Lys Pro Lys Asp Thr Leu Met Ile Ser Arg
            35                  40                  45

Thr Pro Glu Val Thr Cys Val Val Val Asp Val Ser His Glu Asp Pro
        50                  55                  60

Glu Val Gln Phe Asn Trp Tyr Val Asp Gly Val Glu Val His Asn Ala
65                  70                  75                  80

Lys Thr Lys Pro Arg Glu Glu Gln Phe Asn Ser Thr Phe Arg Val Val
                85                  90                  95

Ser Val Leu Thr Val Val His Gln Asp Trp Leu Asn Gly Lys Glu Tyr
            100                 105                 110

Lys Cys Ala Val Ser Asn Lys Gly Leu Pro Ala Pro Ile Glu Lys Thr
        115                 120                 125

Ile Ser Lys Thr Lys Gly Gln Pro Arg Glu Pro Gln Val Tyr Thr Leu
    130                 135                 140

Pro Pro Ser Arg Glu Glu Met Thr Lys Asn Gln Val Ser Leu Thr Cys
145                 150                 155                 160

Leu Val Lys Gly Phe Tyr Pro Ser Asp Ile Ser Val Glu Trp Glu Ser
                165                 170                 175

Asn Gly Gln Pro Glu Asn Asn Tyr Lys Thr Thr Pro Pro Met Leu Asp
            180                 185                 190

Ser Asp Gly Ser Phe Leu Leu Tyr Ser Lys Leu Thr Val Asp Lys Ser
        195                 200                 205

Arg Trp Gln Gln Gly Asn Val Phe Ser Cys Ser Val Met His Glu Ala
    210                 215                 220

Leu His Asn His Tyr Thr Gln Lys Ser Leu Ser Leu Ser Pro Gly Lys
225                 230                 235                 240
```

<210> SEQ ID NO 70
<211> LENGTH: 107
<212> TYPE: PRT
<213> ORGANISM: Homo Sapiens

<400> SEQUENCE: 70

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 71
<211> LENGTH: 5
<212> TYPE: PRT
<213> ORGANISM: Artificial Sequence
<220> FEATURE:
<223> OTHER INFORMATION: Linker sequence

<400> SEQUENCE: 71

Gly Gly Gly Gly Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Hinge sequence

<400> SEQUENCE: 72

Cys Pro Pro Cys Pro Ala Pro
1               5

<210> SEQ ID NO 73
<211> LENGTH: 5
<212> TYPE: PRT
<213> ORGANISM: Artificial Sequence
<220> FEATURE:
<223> OTHER INFORMATION: CD3 VL CDR1

<400> SEQUENCE: 73

Ser Ser Val Ser Tyr
1               5

<210> SEQ ID NO 74
<211> LENGTH: 3
<212> TYPE: PRT
<213> ORGANISM: Artificial Sequence
<220> FEATURE:
<223> OTHER INFORMATION: CD3 VL CDR2

<400> SEQUENCE: 74

Asp Thr Ser
1

```
<210> SEQ ID NO 75
<211> LENGTH: 9
<212> TYPE: PRT
<213> ORGANISM: Artificial Sequence
<220> FEATURE:
<223> OTHER INFORMATION: CD3 VL CDR3

<400> SEQUENCE: 75

Gln Gln Trp Ser Ser Asn Pro Phe Thr
1               5

<210> SEQ ID NO 76
<211> LENGTH: 8
<212> TYPE: PRT
<213> ORGANISM: Artificial Sequence
<220> FEATURE:
<223> OTHER INFORMATION: CD3 VH CDR1

<400> SEQUENCE: 76

Gly Tyr Thr Phe Thr Arg Tyr Thr
1               5

<210> SEQ ID NO 77
<211> LENGTH: 8
<212> TYPE: PRT
<213> ORGANISM: Artificial Sequence
<220> FEATURE:
<223> OTHER INFORMATION: CD3 VH CDR2

<400> SEQUENCE: 77

Ile Asn Pro Ser Arg Gly Tyr Thr
1               5

<210> SEQ ID NO 78
<211> LENGTH: 12
<212> TYPE: PRT
<213> ORGANISM: Artificial Sequence
<220> FEATURE:
<223> OTHER INFORMATION: CD3 VH CDR3

<400> SEQUENCE: 78

Ala Arg Tyr Tyr Asp Asp His Tyr Cys Leu Asp Tyr
1               5                   10

<210> SEQ ID NO 79
<211> LENGTH: 5
<212> TYPE: PRT
<213> ORGANISM: Artificial Sequence
<220> FEATURE:
<223> OTHER INFORMATION: CD25 VL CDR1

<400> SEQUENCE: 79

Ser Ser Arg Ser Tyr
1               5

<210> SEQ ID NO 80
<211> LENGTH: 3
<212> TYPE: PRT
<213> ORGANISM: Artificial Sequence
<220> FEATURE:
<223> OTHER INFORMATION: CD25 VL CDR2

<400> SEQUENCE: 80

Asp Thr Ser
1
```

<210> SEQ ID NO 81
<211> LENGTH: 7
<212> TYPE: PRT
<213> ORGANISM: Artificial Sequence
<220> FEATURE:
<223> OTHER INFORMATION: CD25 VL CDR3

<400> SEQUENCE: 81

His Gln Arg Ser Ser Tyr Thr
1               5

<210> SEQ ID NO 82
<211> LENGTH: 8
<212> TYPE: PRT
<213> ORGANISM: Artificial Sequence
<220> FEATURE:
<223> OTHER INFORMATION: CD25 VH CDR1

<400> SEQUENCE: 82

Gly Tyr Ser Phe Thr Arg Tyr Trp
1               5

<210> SEQ ID NO 83
<211> LENGTH: 8
<212> TYPE: PRT
<213> ORGANISM: Artificial Sequence
<220> FEATURE:
<223> OTHER INFORMATION: CD25 VH CDR2

<400> SEQUENCE: 83

Ile Tyr Pro Gly Asn Ser Asp Thr
1               5

<210> SEQ ID NO 84
<211> LENGTH: 10
<212> TYPE: PRT
<213> ORGANISM: Artificial Sequence
<220> FEATURE:
<223> OTHER INFORMATION: CD25 VH CDR3

<400> SEQUENCE: 84

Ser Arg Asp Tyr Gly Tyr Tyr Phe Asp Phe
1               5                   10

<210> SEQ ID NO 85
<211> LENGTH: 11
<212> TYPE: PRT
<213> ORGANISM: Homo Sapiens

<400> SEQUENCE: 85

Cys Cys Val Glu Cys Pro Pro Cys Pro Ala Pro
1               5                   10

<210> SEQ ID NO 86
<211> LENGTH: 12
<212> TYPE: PRT
<213> ORGANISM: Homo Sapiens

<400> SEQUENCE: 86

Asp Lys Thr His Thr Cys Pro Pro Cys Pro Ala Pro
1               5                   10

<210> SEQ ID NO 87
<211> LENGTH: 11
<212> TYPE: PRT

```
<213> ORGANISM: Artificial Sequence
<220> FEATURE:
<223> OTHER INFORMATION: IgG4 hinge with S228P

<400> SEQUENCE: 87

Tyr Gly Pro Pro Cys Pro Pro Cys Pro Ala Pro
1               5                   10

<210> SEQ ID NO 88
<211> LENGTH: 107
<212> TYPE: PRT
<213> ORGANISM: Homo Sapiens

<400> SEQUENCE: 88

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 89
<211> LENGTH: 106
<212> TYPE: PRT
<213> ORGANISM: Homo Sapiens

<400> SEQUENCE: 89

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 90
<211> LENGTH: 106
<212> TYPE: PRT
<213> ORGANISM: Homo Sapiens

<400> SEQUENCE: 90

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
```

```
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 91
<211> LENGTH: 106
<212> TYPE: PRT
<213> ORGANISM: Homo Sapiens

<400> SEQUENCE: 91

```
Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 92
<211> LENGTH: 106
<212> TYPE: PRT
<213> ORGANISM: Homo Sapiens

<400> SEQUENCE: 92

```
Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Lys Val Ala Trp Lys Ala Asp Gly Ser Pro
            35                  40                  45

Val Asn Thr Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105
```

<210> SEQ ID NO 93
<211> LENGTH: 106
<212> TYPE: PRT

```
<213> ORGANISM: Homo Sapiens

<400> SEQUENCE: 93

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
                100                 105
```

CD3/CD25 ANTIBODIES FOR NEURO-IMMUNE DISEASES

The present invention relates to the use of anti-CD3 and anti-CD25 antibodies for the management and treatment of inflammatory diseases and psycho-immune disorders, such as depression, autism (ASD) and attention deficit/hyperactivity disorder (ADHD).

Provided are compositions related to novel, humanized antibodies or bispecific antibodies, multivalent formats and adjuvants, carriers and methods of administration of such antibodies or bispecific antibodies, including by oral or nasal delivery in humans or preclinical models. This invention further relates to a companion diagnostic as a method of selection of subjects that may benefit from anti-CD3/anti-CD25 therapy and a biomarker for rapid and easy monitoring of response to treatment.

TECHNICAL BACKGROUND

Inflammation is an immune response to protect the body from physical and emotional stressors that can cause or exacerbate psychological disorders (Miller and Raison 2016, Wang 2018, Leffa 2018, Dunn 2019, Gupta 2014, Siniscalco 2018).

Depression is currently the leading cause of disability globally (World Health Organization (WHO)— Depression and Other Common Mental Disorders Global Health Estimates, report 2017; NIH-NIMH, report 2017; BCBS report 2018; Gautam, 2017, www_who.int/news-room/fact-sheets/detail/depression, GBD 2018). The prevalence of depression ranges from 3% of the population in Japan to 17% in the United States (Orsolini 2020). In the United States, 3.2% of children ages 3-17 years (approximately 1.9 million) have diagnosed depression, frequently co-diagnosed with ADHD (17%) or ASD (14%) (CDC website, 2020, Ghandour 2018). Numbers have risen sharply in recent years, particularly among millennials and adolescents (47% for boys and 65% for girls since 2013). 50% of all new cases of depression are diagnosed before the age of 14 and 75% of cases by the age of 24 (BCBS report, 2018). Two thirds of youth suicide cases in the United States have been linked to depression and the overall risk for suicide for people with depression is estimated at 15% (Orsolini 2020, CDC, 2008).

Mechanisms of Disease

Gut microbiota dysbiosis, which causes local, and through disruption of the intestinal barrier systemic inflammation (Belizario 2018) is prevalent in people with depression, ADHD and ASD (Valles-Colomer 2019, Zheng 2019, Bezewada 2020, Xu 2019, Stevens 2019), and may affect brain function through both systemic and autonomic pathways (Tengeler 2020, Sharon 2019).

Serotonin is an essential neurotransmitter that enhances mood, social connections, memory and healthy sleep patterns. Depression has been associated with a disturbance in serotonin (5-HT) and noradrenaline neurotransmission (Coopen and Swede, 1988) and MRI studies have suggested a correlation between increased risk of suicide and low levels of brain serotonin (Mann, 1990, Sullivan, 2015).

The relationship between inflammation and psychiatric disorders is not fully understood (Miller and Raison, 2016, Dantzer, 2011, Smith 1991). Smith (1991) suggested that depression is caused by excessive levels of pro-inflamatory cytokines in response to acute or chronic stress that penetrate the blood-brain barrier and alter the metabolism and synaptic signaling of neurotransmitters. Furthermore, brain microglia, activated by peripheral signals may release additional inflammatory cytokines locally.

It has been reported that brain areas targeted by cytokines overlap with those that are altered in depressed patients and include the prefrontal cortex (Juengling et al 2000), the anterior cingulate cortex (Capuron 2005), the putamen, the basal ganglia and cerebellum (Capuron et al 2007).

CD4+CD25+ TREGs release IL-10 and TGF-b which inhibit cytotoxic T cells and their secretion of pro-inflammatory cytokines, preventing excessive activation of effector immune cells (Montufar Solis, 2007).

TREGs also express programmed death receptors and ligands, which stabilize the relationship between Tregs and antigen presenting cells (APCs) while promoting the differentiation of inducible regulatory T cells (iTREGs). Moreover, TREGs can downregulate the expression levels of costimulatory molecules CD80 and CD86 on DCs and affect the function of DCs, thereby achieving immunosuppressive effects.

CD3 and CD25

CD3 is a protein complex and T cell co-receptor that is involved in activating T cells. CD3 is selectively expressed on T cells in blood, bone marrow and lymphoid tissues, but not on other normal tissues and with no cross reactivity to other animals except for chimpanzee.

CD25 (IL-2 receptor subunit a) is another T cell surface glycoprotein, expressed in activated T cells and present in the the spleen, tonsils, marrow and lymphoid tissue. Blockade of CD25 prevents IL-2 binding and results in both inhibition of cytotoxic T cell proliferation and activation of TREGs which secrete the anti-inflammatory cytokines IL-10, IL-35 and TGF-B and further inhibit effector T cells.

SUMMARY OF THE INVENTION

It has been estimated that 76% and 85% of people in low- and middle-income countries receive no treatment for their mental disorder due to the lack of mental health policies, financial aid, infrastructure and effective interventions (WHO, 2017; Wang, The Lancet, 2007). Thus, there is a need for easily available and effective means for management and treatment of such disorders.

The WHO has warned that current healthcare systems are not prepared to address the anticipated surge in mental disease burden in the next decade and that treatment options that are effective and safe are sorely needed (World Health Organization (WHO 2012, 2017). Thus, there is a need for effective and safe means for management and treatment of such disorders.

The lack of clear understanding of the etiology of depression, the lack of experimental models of disease and the lack of biomarkers to select patients that may benefit from a given treatment or to assess response as well as the prohibitive cost of currently available imaging technologies contribute to the challenges in developing therapies for depression (Arnow, 2015). Numerous clinical trials have failed and only a few new antidepressants have been approved in the last 20 years (Blackburn 2019). Thus, there is a need for effective and reliable means for diagnosing, monitoring and treating such disorders.

Currently available drugs for depression, ADHD or ASD are not optimized for children, have suboptimal efficacy, high levels of relapse/recurrence and associated with withdrawal syndrome or side-effects including black box warnings. Thus, there is a need for effective and safe means for management and treatment of such disorders in children and adolescents.

As many as ⅓ of the population diagnosed with any type of depression fails conventional therapy (Blackburn 2019), presenting recurrent or relapsed disease. The majority of these individuals present inflammatory disease, in particular children previously exposed to adverse events (Blackburn 2019, Al-Harbi 2012, Dantzer 2011, Miller and Cole 2012). Similar findings linking inflammation to ADHD and ASD have been reported (Leffa 2018, Siniscalco 2019). Thus, there is a need for effective and safe means for management and treatment of such recurrent or relapsed disease.

To the best of the inventor's knowledge, there are no biological therapies in development for depression, ADHD or ASD, although the use of antibodies for the treatment of cancers and other inflammatory conditions is a well-known strategy (Labrijn 2019, Kaplon 2020, Lu 2020). Thus, there is a need for biological therapies for management and treatment of conditions such as depression, ADHD or ASD.

Standard of care antidepressants include selective serotonin reuptake inhibitors (SSRIs) but also tricyclic antidepressants, mirtazapine, bupropion, and venlafaxine, which may be taken indefinitely, until relapse or side-effects are observed. Optional treatments include electroconvulsive therapy (ECT) and psychosocial interventions, repetitive transcranial magnetic stimulation (rTMS), light therapy, transcranial direct stimulation, vagal nerve stimulation, deep brain stimulation and sleep deprivation treatment. Benzodiazepines may be used as adjunctive treatment, and lithium and thyroid supplements may be used as an augmenting agent when a patient is not responding to antidepressants (Gautam, 2017).

Studies have also shown that increased glutamate excitatory transmission predicts suicidal behavior in patients with MDD prompting the use of NMDA glutamate receptor inhibitors ketamine or esketamine (Yuksel and Orgun, 2010, Serafini, 2015, Matthews, 2012, Zhao, 2018, Lent 2019, esketamine FDA label).

Despite the available drug repertoire, as many as ⅓ of the population diagnosed with any type of depression fails conventional therapy (Al-Harbi, 2012), presenting resistant or relapsed disease. Thus, there is a need for effective and safe means for management and treatment of depression. There is a need for effective and safe means for management and treatment of depression in subjects that fails conventional therapy. There is a need for effective and safe means for management and treatment of resistant or relapsed depression.

In addition, current medication for ADHD and ASD is based on drugs with substantial side-effects. Methylphenidate and atomoxetine inhibit the re-uptake of dopamine and norepinephrine respectively and are approved for ADHD. Risperidone and aripiprazole are non-indication specific anti-psychotics and the only drugs approved by the FDA for children with autism spectrum disorder to help with irritability. Thus, there is a need for safer means for management and treatment of such disorders. There is a need for means for management and treatment of such disorders with fever side-effects. There is a need for safer means for management and treatment of such disorders, potentially with fewer side-effect and potentially more suitable for children and adolescents.

A wide range of anti-inflammatory agents such as COX2 inhibitors have been tested in patients suffering from major depressive disorder however their efficacy requires further evaluation (MDD) (Muller, 2010). Thus, there is a need for effective and safe means for management and treatment of such disorders.

Several non-clinical and clinical studies suggest that inflammation is related at least in part by regulatory T cells (TREGs) insufficiency (da Cunha, 2011, Kuhn and Weiner, 2016, Moaaz, 2019) which inhabit the intestinal tract. Moaaz et al 2019 showed a systemic TREG imbalance that correlated negatively with the severity of disease in children with ASD. The role of TREGs has been also described in Inflammatory Bowl Disease (Ding 2020). Thus, there is a need for a better understanding of TREGs role in these diseases.

Recently, human CD3 transgenic mice have been engineered, facilitating the study of anti-CD3 immunotherapies. Anti-CD3 based therapies such as muromomab-CD3 (Janssen, Orthoclone, OKT3) have been extensively studied in humans both systemically and orally for ulcerative cholitis and metabolic syndrome (da Cunha 2011, Ilan 2010-NCT01287195, NCT01205087). Thus, there is a need for improved therapeutics targeting CD3.

Anti-CD3 bispecific antibody platforms that bridge tumors and T cells such as blinatumomab and catumaxomab have been approved for the treatment of cancer and several others CD3 bispecifics are in clinical development (Suurs, 2019).

Systemic anti-CD3 therapy for management of graft rejection is associated with high toxicity due to general depletion of T cells and cytokine release syndrome (Kuhn and Weiner, 2016, X). Moreover, early studies used murine antibodies, limiting their clinical utility and precluding high or repeat dosing strategies. Thus, there is a need for improved therapeutics targeting CD3.

Da Cunha (2011), Ochi (2006), Kuhn (2016), Ishikawa (2007), Boden (2019) and Rezende (2019) have described the immunosuppressive effect of murine and humanized anti-CD3 antibodies (moromomab, teplizumab, visilizumab and foralumab) in autoimmune diseases, hepatitis and diabetes.

Daclixumab was approved for multiple sclerosis and was later withdrawn due to safety concerns. Several groups are currently investigating the use of anti-CD25 antibodies to target cancer (camidanlumab-Genmab, aCD25NIB-Roche, AACR 2018 abstract 2787 and 192). Thus, there is a need for improved therapeutics targeting CD25

It is speculated that a CD3/CD25 multivalent antibody format will minimize off-target, non-TREG T cell binding and increase the potency of an anti-inflammatory, anti-depressive effect. TREG activation inhibits effector T cell pro-inflammatory cytokine release, secretes immune suppressive cytokines and activates dendritic cells to produce substrates necessary for neurotransmitter synthesis such as tryptophan for serotonin (5H-T) and inhibit NMDA mediated excitatory signaling.

According to an aspect, the invention concerns an antibody or fragment thereof, capable of binding to CD3 and/or CD25.

According to another aspect, the invention concerns a pharmaceutical composition comprising an antibody or fragment thereof according to the invention and an excipient, such as a pharmaceutically-acceptable carrier.

According to another aspect, the invention concerns a method of preventing, treating and/or alleviating an inflammatory disease, a psycho-immune disorder, an auto-immune disease and/or a mood disorder comprising administering to a patient in need thereof a therapeutically effective amount of the antibody or fragment thereof and/or pharmaceutical composition according to the invention.

According to another aspect, the invention concerns a method of preventing, treating and/or alleviating an inflammatory disease comprising administering to a patient in need thereof a therapeutically effective amount of the antibody or fragment thereof and/or pharmaceutical composition according to the invention.

According to another aspect, the invention concerns a method of preventing, treating and/or alleviating a mood disorder comprising administering to a patient in need thereof a therapeutically effective amount of the antibody or fragment thereof and/or pharmaceutical composition according to the invention.

According to another aspect, the invention concerns a method of preventing, treating and/or alleviating a psycho-immune disorder comprising administering to a patient in need thereof a therapeutically effective amount of the antibody or fragment thereof and/or pharmaceutical composition according to the invention.

According to another aspect, the invention concerns a diagnostic kit comprising the antibody or fragment thereof according to the invention and instructions for use.

According to another aspect, the invention concerns a method of diagnosing a disease in a subject, wherein said method comprises the following steps:
  a) Providing a blood and/or salivary sample from said subject.
  b) Contacting said blood and/or salivary sample with an antibody or fragment thereof according to the invention.

According to another aspect, the invention concerns a method of screening and/or monitoring progression of a disease in a subject, wherein said method comprises the following steps:
  a) Providing a blood and/or salivary sample from said subject.
  b) Contacting said blood and/or salivary sample with an antibody or fragment thereof according to the invention.

According to another aspect, the invention concerns an isolated nucleic acid molecule encoding an antibody agent or fragment thereof according to the invention.

According to another aspect, the invention concerns a recombinant vector comprising a nucleic acid molecule of the invention.

According to another aspect, the invention concerns a host cell comprising the recombinant vector of the invention.

According to another aspect, the invention concerns a method for the production of an antibody or fragment thereof according to the invention comprising a step of culturing the host cell according to the invention in a culture medium under conditions allowing the expression of the antibody or fragment thereof and separating the antibody or fragment thereof from the culture medium.

According to another aspect, the invention concerns a method for generating a heterodimeric antibody, said method comprising the following steps:
  a) providing a first homodimeric antibody comprising a first Fc region, said first Fc region comprising a first CH3 region selected from the group consisting of a human IgG2 CH3 region and a human IgG4 CH3 region, but with an amino acid substitution at a position selected from the group consisting of: 405, 409, 234, 235 and 322 (EU numbering);
  b) providing a second homodimeric antibody comprising a second Fc region, said second Fc region comprising a second CH3 region selected from the group consisting of a human IgG2 CH3 region and a human IgG4 CH3 region, but with an amino acid substitution at a position selected from the group consisting of: 405, 409, 234, 235 and 322 (EU numbering), wherein the sequences of said first and second antibody CH3 regions are different,
  c) incubating said first antibody together with said second antibody under reducing conditions sufficient to allow the cysteines in the hinge region to undergo disulfide-bond isomerization, to obtain a heterodimeric antibody.

According to another aspect, the invention concerns a method for generating a heterodimeric antibody, said method comprising the following steps:
  a) providing a first homodimeric antibody comprising an Fc region, said Fc region comprising a first CH3 region selected from the group consisting of a human IgG2 CH3 region and a human IgG4 CH3 region, but with an amino acid substitution at position 409 (EU numbering);
  b) providing a second homodimeric antibody comprising an Fc region, said Fc region comprising a second CH3 region selected from the group consisting of a human IgG2 CH3 region and a human IgG4 CH3 region, but with an amino acid substitution at position 405 (EU numbering),
  c) incubating said first antibody together with said second antibody under reducing conditions sufficient to allow the cysteines in the hinge region to undergo disulfide-bond isomerization,
to obtain a heterodimeric antibody,
wherein the heterodimeric interaction between said first and second antibodies in the resulting heterodimeric antibody is such that no Fab-arm exchange occurs at 0.5 mM GSH after 24 hours at 37° C., and According to another aspect, the invention concerns a method for generating a heterodimeric antibody, said method comprising the following steps:
  a) providing a first homodimeric antibody comprising an Fc region, said Fc region comprising a first CH3 region selected from the group consisting of a human IgG2 CH3 region and a human IgG4 CH3 region;
  b) providing a second homodimeric antibody comprising an Fc region, said Fc region comprising a second CH3 region selected from the group consisting of a human IgG2 CH3 region and a human IgG4 CH3 region, but with an amino acid substitution at position 405 and an amino acid substitution at position 409 (EU numbering),
  c) incubating said first antibody together with said second antibody under reducing conditions sufficient to allow the cysteines in the hinge region to undergo disulfide-bond isomerization,
to obtain a heterodimeric antibody,
wherein the heterodimeric interaction between said first and second antibodies in the resulting heterodimeric antibody is such that no Fab-arm exchange occurs at 0.5 mM GSH after 24 hours at 37° C.

According to another aspect, the invention concerns a heterodimeric antibody obtainable by the method according to the invention.

According to another aspect, the invention concerns a heterodimeric antibody comprising:
  A first heavy chain comprising a first Fc region, said first Fc region comprising a first CH3 region selected from the group consisting of a human IgG2 CH3 region and a human IgG4 CH3 region, but with an amino acid substitution at position 405 (EU numbering), and
  A second heavy chain comprising a second Fc region, said second Fc region comprising a second CH3 region selected from the group consisting of a human IgG2 CH3 region and a human IgG4 CH3, but with an amino acid substitution at position 409 (EU numbering);

Wherein the sequences of the first and second CH3 regions are different.

According to another aspect, the invention concerns a heterodimeric antibody comprising:

A first heavy chain comprising a first Fc region, said first Fc region comprising a first CH3 region selected from the group consisting of a human IgG2 CH3 region and a human IgG4 CH3 region, and A second heavy chain comprising a second Fc region, said second Fc region comprising a second CH3 region selected from the group consisting of a human IgG2 CH3 region and a human IgG4 CH3, but with an amino acid substitution at position 405 and an amino acid substitution at position 409 (EU numbering);

Wherein the sequences of the first and second CH3 regions are different.

According to another aspect, the invention concerns a pharmaceutical composition comprising a heterodimeric antibody according to the invention and an excipient, such as a pharmaceutical carrier.

According to another aspect, the invention concerns a bispecific antibody or fragment thereof comprising a first antigen binding site capable of binding to a first antigen and a second antigen binding site capable of binding to a second antigen, wherein said first antigen binding site is comprised in a Fab fragment and said second antigen binding site is comprised in a moiety selected from the group consisting of scFv, antibody fragments and protein moiety, wherein said moiety being attached to the light chain of said Fab fragment.

According to another aspect, the invention concerns a heterodimeric antibody, wherein said heterodimeric antibody comprises a human IgG4 Fc domain, wherein said heterodimeric antibody binds to two or more different targets and wherein said heterodimeric antibody further comprises a component selected from
(i) a Fab,
(ii) a scFv,
(iii) a variable heavy homodimer (VHH), and/or
(iv) an antibody fragment.

According to another aspect, the invention concerns a heterodimeric antibody, wherein said heterodimeric antibody comprises a human IgG2 Fc domain, wherein said heterodimeric antibody binds to two or more different targets and wherein said heterodimeric antibody further comprises a component selected from
(i) a Fab,
(ii) a scFv,
(iii) a variable heavy homodimer (VHH), and/or
(iv) an antibody fragment.

According to another aspect, the invention concerns an IgG2, IgG3 or IgG4 molecule that comprises a light chain and an antibody domain and/or protein fused to the C-terminus of said light chain, wherein said antibody domain is selected from
(i) a Fab,
(ii) a scFv,
(iii) a variable heavy homodimer (VHH), and/or
(iv) an antibody fragment.

DETAILED DISCLOSURE

According to an embodiment, the invention concerns an antibody or fragment thereof, capable of binding to CD3 and/or CD25.

According to an embodiment, the invention concerns the antibody or fragment thereof, capable of binding to CD3.

According to an embodiment, the invention concerns the antibody or fragment thereof, wherein said antibody or fragment thereof comprises at least one of the amino acid sequences of CDR1, CDR2 and CDR3 of the murine antibody OKT3 variable light chain and/or at least one of the amino acid sequences of CDR1, CDR2 and CDR3 of the murine antibody OKT3 variable heavy chain.

According to an embodiment, the invention concerns the antibody or fragment thereof, wherein said antibody or fragment thereof comprises the amino acid sequences of CDR1, CDR2 and CDR3 of the murine antibody OKT3 variable light chain and/or the amino acid sequences of CDR1, CDR2 and CDR3 of the murine antibody OKT3 variable heavy chain.

According to an embodiment, the invention concerns the antibody or fragment thereof, wherein said antibody or fragment thereof comprises variable light chain CDR sequences of SEQ ID NO:73-75.

According to an embodiment, the invention concerns the antibody or fragment thereof, wherein said antibody or fragment thereof comprises variable heavy chain CDR sequences of SEQ ID NO:76-78.

According to an embodiment, the invention concerns the antibody or fragment thereof, wherein said antibody or fragment thereof comprises variable light chain CDR sequences of SEQ ID NO:73-75 and variable heavy chain CDR sequences of SEQ ID NO:76-78.

According to an embodiment, the invention concerns the antibody or fragment thereof, wherein all antigen contact residues of murine antibody OKT3 are contained.

According to an embodiment, the invention concerns the antibody or fragment thereof, wherein all CDR sequences of murine antibody OKT3 are contained.

According to an embodiment, the invention concerns the antibody or fragment thereof wherein all antigen contact residues and all CDR sequences of murine antibody OKT3 are contained.

According to an embodiment, the invention concerns the antibody or fragment thereof comprising the murine antibody OKT3 variable heavy chain residue K82 (IMGT numbering).

According to an embodiment, the invention concerns the antibody or fragment thereof, wherein said antibody or fragment thereof comprises a variable heavy chain domain of SEQ ID NO:6-10 and a variable light chain domain of SEQ ID NO:1-5.

According to an embodiment, the invention concerns the antibody or fragment thereof, wherein said antibody or fragment thereof comprises a Cys114Ser mutation (IMGT numbering) in the heavy chain CDR3 region.

According to an embodiment, the invention concerns the antibody or fragment thereof, capable of binding to CD25.

According to an embodiment, the invention concerns the antibody or fragment thereof, wherein said antibody or fragment thereof comprises at least one of the amino acid sequences of CDR1, CDR2 and CDR3 of the monoclonal antibody Basiliximab variable light chain and/or at least one of the amino acid sequences of CDR1, CDR2 and CDR3 of the monoclonal antibody Basiliximab variable heavy chain.

According to an embodiment, the invention concerns the antibody or fragment thereof, wherein said antibody or fragment thereof comprises the amino acid sequences of CDR1, CDR2 and CDR3 of the monoclonal antibody Basiliximab variable light chain and/or the amino acid sequences of CDR1, CDR2 and CDR3 of the monoclonal antibody Basiliximab variable heavy chain.

According to an embodiment, the invention concerns the antibody or fragment thereof, wherein said antibody or fragment thereof comprises variable light chain CDR sequences of
SEQ ID NO:79-81.

According to an embodiment, the invention concerns the antibody or fragment thereof, wherein said antibody or fragment thereof comprises variable heavy chain CDR sequences of SEQ ID NO:82-84.

According to an embodiment, the invention concerns the antibody or fragment thereof, wherein said antibody or fragment thereof comprises variable light chain CDR sequences of SEQ ID NO:79-81 and variable heavy chain CDR sequences of SEQ ID NO:82-84.

According to an embodiment, the invention concerns the antibody or fragment thereof, wherein all antigen contact residues of monoclonal antibody Basiliximab are contained.

According to an embodiment, the invention concerns the antibody or fragment thereof, wherein all CDR sequences of monoclonal antibody Basiliximab are contained.

According to an embodiment, the invention concerns the antibody or fragment thereof, wherein all antigen contact residues and all CDR sequences of monoclonal antibody Basiliximab are contained.

According to an embodiment, the invention concerns the antibody or fragment thereof, wherein said antibody or fragment thereof comprises a variable heavy chain domain of SEQ ID NO:29-31 and a variable light chain domain of SEQ ID NO:32-34.

According to an embodiment, the invention concerns the antibody or fragment thereof, wherein said antibody or fragment thereof is humanized.

According to an embodiment, the invention concerns the antibody or fragment thereof, wherein said antibody or fragment thereof comprises a scFv.

According to an embodiment, the invention concerns the antibody or fragment thereof, wherein said antibody or fragment thereof is a scFv.

According to an embodiment, the invention concerns the antibody or fragment thereof, wherein said scFv has increased disulfide stabilization.

According to an embodiment, the invention concerns the antibody or fragment thereof, wherein said scFv comprises at least one Cys substitution at a position selected from VH44-VL100 according to Kabat numbering.

According to an embodiment, the invention concerns the antibody or fragment thereof, wherein said antibody or fragment thereof comprises a linker.

According to an embodiment, the invention concerns the antibody or fragment thereof, wherein said scFv comprises a linker.

According to an embodiment, the invention concerns the antibody or fragment thereof, wherein said linker is a peptide linker.

According to an embodiment, the invention concerns the antibody or fragment thereof, wherein said linker comprises the sequence of SEQ ID NO:71.

According to an embodiment, the invention concerns the antibody or fragment thereof, wherein said scFv binds CD3 and comprises a sequence selected from the group consisting of SEQ ID NO:11-28.

According to an embodiment, the invention concerns the antibody or fragment thereof, wherein said scFv binds CD25 and comprises a sequence selected from the group consisting of SEQ ID NO:35-50.

According to an embodiment, the invention concerns the antibody or fragment thereof, wherein said antibody or fragment thereof comprises a constant light chain (CL) domain selected from the group consisting of kappa CL domain and lambda CL domain.

According to an embodiment, the invention concerns the antibody or fragment thereof, wherein said antibody or fragment thereof comprises a sequence selected from the group consisting of a kappa CL domain sequence and a lambda CL domain sequence.

According to an embodiment, the invention concerns the antibody or fragment thereof, wherein said antibody or fragment thereof comprises a sequence of SEQ ID NO:70.

According to an embodiment, the invention concerns the antibody or fragment thereof, wherein said antibody or fragment thereof is a heterodimeric construct.

According to an embodiment, the invention concerns the antibody or fragment thereof, wherein said heterodimeric construct comprises IgG2 and/or IgG4 constant domain.

According to an embodiment, the invention concerns the antibody or fragment thereof, wherein said heterodimeric construct comprises a point mutation selected from the group consisting of K409R, R409K, F405L, L234A, F234A, V234A, L235A, K322A and S228P.

According to an embodiment, the invention concerns the antibody or fragment thereof, wherein said antibody or fragment thereof comprises a sequence selected from the group consisting of SEQ ID NO:51-69.

According to an embodiment, the invention concerns the antibody or fragment thereof, wherein said antibody or fragment thereof is a monospecific antibody.

According to an embodiment, the invention concerns the antibody or fragment thereof, wherein said antibody or fragment thereof is a bispecific antibody.

According to an embodiment, the invention concerns the antibody or fragment thereof, wherein said antibody or fragment thereof is a multispecific antibody.

According to an embodiment, the invention concerns the antibody or fragment thereof, wherein said antibody or fragment thereof is a 4 chain IgG antibody.

According to an embodiment, the invention concerns the antibody or fragment thereof, wherein said antibody or fragment thereof is a 2 chain scFv-Fc antibody.

According to an embodiment, the invention concerns the antibody or fragment thereof, wherein said antibody or fragment thereof is a 2 chain scFv-Fc-scFv antibody.

According to an embodiment, the invention concerns the antibody or fragment thereof, wherein said antibody or fragment thereof is 2 chain scFv-IgG4-Fc antibody.

According to an embodiment, the invention concerns the antibody or fragment thereof, wherein said antibody or fragment thereof comprises a first antigen binding site capable of binding to CD3 and a second antigen binding site capable of binding to CD25, wherein said first antigen binding site is comprised in a Fab fragment and said second antigen binding site is comprised in a moiety selected from the group consisting of scFv, antibody fragments and protein moiety, wherein said moiety being attached to the light chain of said Fab fragment.

According to an embodiment, the invention concerns the antibody or fragment thereof, wherein said moiety is a scFv.

According to an embodiment, the invention concerns the antibody or fragment thereof, wherein said moiety is attached to the C-terminus or N-terminus of the light chain of said Fab fragment.

According to an embodiment, the invention concerns the antibody or fragment thereof, wherein said moiety is attached to the C-terminus of the light chain of said Fab fragment.

According to an embodiment, the invention concerns the antibody or fragment thereof, wherein said Fab fragment is derived from an IgG or an IgM.

According to an embodiment, the invention concerns the antibody or fragment thereof, wherein said Fab fragment is derived from an IgG.

According to an embodiment, the invention concerns the antibody or fragment thereof, wherein said Fab fragment is derived from an IgG selected from the group consisting of IgG1, IgG2, IgG3 and IgG4.

According to an embodiment, the invention concerns the antibody or fragment thereof, wherein said Fab fragment is derived from an IgG2 or an IgG4.

According to an embodiment, the invention concerns the antibody or fragment thereof, wherein said antibody or fragment thereof is isolated.

According to an embodiment, the invention concerns the antibody or fragment thereof, wherein said antibody or fragment thereof has increased stability and/or increased manufacturability.

According to an embodiment, the invention concerns a pharmaceutical composition comprising an antibody or fragment thereof according to the invention and an excipient, such as a pharmaceutically-acceptable carrier.

According to an embodiment, the invention concerns the pharmaceutical composition comprising an adjuvant.

According to an embodiment, the invention concerns the pharmaceutical composition, wherein said adjuvant is selected from the group consisting of β-D-galactosylceramide, α-D-galactosylceramide and β-glucan.

According to an embodiment, the invention concerns the pharmaceutical composition, wherein said pharmaceutical composition is a stabilized pharmaceutical.

According to an embodiment, the invention concerns the antibody or fragment thereof and/or pharmaceutical composition according to the invention, wherein said antibody or antigen binding fragment and/or pharmaceutical composition allows administration through a route selected among subcutaneous administration, intradermal administration, intramuscular administration, oral administration and/or nasal administration.

According to an embodiment, the invention concerns the antibody or fragment thereof and/or pharmaceutical composition according to the invention, wherein said antibody or antigen binding fragment and/or pharmaceutical composition allows administration through a route selected among oral and nasal administration.

According to an embodiment, the invention concerns a method of preventing, treating and/or alleviating an inflammatory disease, a psycho-immune disorder, an auto-immune disease and/or a mood disorder comprising administering to a patient in need thereof a therapeutically effective amount of the antibody or fragment thereof and/or pharmaceutical composition according to the invention.

According to an embodiment, the invention concerns a method of preventing, treating and/or alleviating an inflammatory disease comprising administering to a patient in need thereof a therapeutically effective amount of the antibody or fragment thereof and/or pharmaceutical composition according to the invention.

According to an embodiment, the invention concerns a method of preventing, treating and/or alleviating a mood disorder comprising administering to a patient in need thereof a therapeutically effective amount of the antibody or fragment thereof and/or pharmaceutical composition according to the invention.

According to an embodiment, the invention concerns a method of preventing, treating and/or alleviating a psycho-immune disorder comprising administering to a patient in need thereof a therapeutically effective amount of the antibody or fragment thereof and/or pharmaceutical composition according to the invention.

According to an embodiment, the invention concerns the method, wherein said inflammatory disease, psycho-immune disorder and/or a mood disorder is selected from the group consisting of depression, major depressive disorder, autism (ASD) and attention deficit/hyperactivity disorder (ADHD), bipolar disorder, seasonal affective disorder (SAD), cyclothymic disorder, premenstrual dysphoric disorder, persistent depressive disorder, disruptive mood dysregulation disorder, depression related to medical illness, depression induced by substance use or medication.

According to an embodiment, the invention concerns the method, wherein said subject is an adult or a pediatric subject.

According to an embodiment, the invention concerns the method, wherein said antibody or fragment thereof and/or pharmaceutical composition is administered subcutaneously, intradermally, intramuscularly, orally and/or nasally.

According to an embodiment, the invention concerns the method, wherein said antibody or fragment thereof and/or pharmaceutical composition is administered subcutaneously, intradermally, intramuscularly, orally and/or nasally.

According to an embodiment, the invention concerns a diagnostic kit comprising the antibody or fragment thereof according to the invention and instructions for use.

According to an embodiment, the invention concerns the diagnostic kit, wherein said diagnostic kit is for companion diagnostic.

According to an embodiment, the invention concerns the diagnostic kit, wherein said diagnostic kit is for the selection of patients that may benefit from treatment with an antibody of fragment thereof according to the invention.

According to an embodiment, the invention concerns a method of diagnosing a disease in a subject, wherein said method comprises the following steps:
  a. Providing a blood and/or salivary sample from said subject.
  b. Contacting said blood and/or salivary sample with an antibody or fragment thereof according to the invention.

According to an embodiment, the invention concerns a method of screening and/or monitoring progression of a disease in a subject, wherein said method comprises the following steps:
  a. Providing a blood and/or salivary sample from said subject.
  b. Contacting said blood and/or salivary sample with an antibody or fragment thereof according to the invention.

According to an embodiment, the invention concerns the method, wherein blood and/or salivary sample is monitored for a blood and/or salivary biomarker.

According to an embodiment, the invention concerns the method, wherein blood and/or salivary biomarker is a TREG cell biomarker.

According to an embodiment, the invention concerns an isolated nucleic acid molecule encoding an antibody agent or fragment thereof according to the invention.

According to an embodiment, the invention concerns a recombinant vector comprising the nucleic acid molecule of the invention.

According to an embodiment, the invention concerns a host cell comprising the recombinant vector of the invention.

According to an embodiment, the invention concerns a method for the production of an antibody or fragment thereof according to the invention comprising a step of culturing the host cell according to the invention in a culture medium under conditions allowing the expression of the antibody or fragment thereof and separating the antibody or fragment thereof from the culture medium.

According to an embodiment, the invention concerns the antibody or fragment thereof, wherein the antibody or fragment thereof is produced by a recombinant vector comprising a nucleic acid encoding said antibody.

According to an embodiment, the invention concerns a method for generating a heterodimeric antibody, said method comprising the following steps:
  a) providing a first homodimeric antibody comprising a first Fc region, said first Fc region comprising a first CH3 region selected from the group consisting of a human IgG2 CH3 region and a human IgG4 CH3 region, but with an amino acid substitution at a position selected from the group consisting of: 405, 409, 234, 235 and 322 (EU numbering);
  b) providing a second homodimeric antibody comprising a second Fc region, said second Fc region comprising a second CH3 region selected from the group consisting of a human IgG2 CH3 region and a human IgG4 CH3 region, but with an amino acid substitution at a position selected from the group consisting of: 405, 409, 234, 235 and 322 (EU numbering),
  wherein the sequences of said first and second antibody CH3 regions are different,
  c) incubating said first antibody together with said second antibody under reducing conditions sufficient to allow the cysteines in the hinge region to undergo disulfide-bond isomerization,
  to obtain a heterodimeric antibody.

According to an embodiment, the invention concerns a method for generating a heterodimeric antibody, said method comprising the following steps:
  a) providing a first homodimeric antibody comprising an Fc region, said Fc region comprising a first CH3 region selected from the group consisting of a human IgG2 CH3 region and a human IgG4 CH3 region, but with an amino acid substitution at position 409 (EU numbering);
  b) providing a second homodimeric antibody comprising an Fc region, said Fc region comprising a second CH3 region selected from the group consisting of a human IgG2 CH3 region and a human IgG4 CH3 region, but with an amino acid substitution at position 405 (EU numbering),
  c) incubating said first antibody together with said second antibody under reducing conditions sufficient to allow the cysteines in the hinge region to undergo disulfide-bond isomerization,
  to obtain a heterodimeric antibody,
  wherein the heterodimeric interaction between said first and second antibodies in the resulting heterodimeric antibody is such that no Fab-arm exchange occurs at 0.5 mM GSH after 24 hours at 37° C., and According to an embodiment, the invention concerns a method for generating a heterodimeric antibody, said method comprising the following steps:
  a) providing a first homodimeric antibody comprising an Fc region, said Fc region comprising a first CH3 region selected from the group consisting of a human IgG2 CH3 region and a human IgG4 CH3 region;
  b) providing a second homodimeric antibody comprising an Fc region, said Fc region comprising a second CH3 region selected from the group consisting of a human IgG2 CH3 region and a human IgG4 CH3 region, but with an amino acid substitution at position 405 and an amino acid substitution at position 409 (EU numbering),
  c) incubating said first antibody together with said second antibody under reducing conditions sufficient to allow the cysteines in the hinge region to undergo disulfide-bond isomerization,
  to obtain a heterodimeric antibody,
  wherein the heterodimeric interaction between said first and second antibodies in the resulting heterodimeric antibody is such that no Fab-arm exchange occurs at 0.5 mM GSH after 24 hours at 37° C.

According to an embodiment, the invention concerns the method, wherein said method is performed in vitro.

According to an embodiment, the invention concerns the method, wherein said first and/or second CH3 region is of human IgG2.

According to an embodiment, the invention concerns the method, wherein said first and/or second CH3 region is of human IgG4.

According to an embodiment, the invention concerns the method, wherein said first and/or second Fc region is of human IgG2 or human IgG4.

According to an embodiment, the invention concerns the method, wherein said heterodimeric antibody comprises a hinge region selected from a IgG1 hinge region or a IgG4 hinge region with a S228P mutation.

According to an embodiment, the invention concerns the method, wherein said first Fc region and/or said second Fc region is chimeric, humanized, or human.

According to an embodiment, the invention concerns the method, wherein said amino acid substitution is selected from the group consisting of: F405L, K409R, L234A, F234A, V234A, L235A, N297A and K322A (EU numbering).

According to an embodiment, the invention concerns the method, wherein said first and second homodimeric antibodies bind different epitopes.

According to an embodiment, the invention concerns the method, wherein the heterodimeric interaction between said first and second antibodies in the resulting heterodimeric antibody is such that no Fab-arm exchange occurs.

According to an embodiment, the invention concerns the method, wherein the heterodimeric interaction between said first and second antibodies in the resulting heterodimeric antibody is such that no Fab-arm exchange occurs at 0.5 mM GSH after 24 hours at 37° C.

According to an embodiment, the invention concerns the method, wherein the heterodimeric interaction between said first and second antibodies in the resulting heterodimeric antibody is such that no Fab-arm exchange occurs and wherein said first and/or second Fc region is of human IgG4 but with an amino acid substitution at a position 228 (EU numbering).

According to an embodiment, the invention concerns the method, wherein said amino acid substitution is S228P.

According to an embodiment, the invention concerns the method, wherein said first homodimeric antibody has an amino acid other than Lys at position 409 and said second homodimeric antibody has an amino acid other than Phe at position 405.

According to an embodiment, the invention concerns the method, wherein said first homodimeric antibody comprises an Arg at position 409 and said second homodimeric antibody comprises a Leu at position 405.

According to an embodiment, the invention concerns the method, wherein said first and second homodimeric antibodies provided in steps a) and b) are purified.

According to an embodiment, the invention concerns the method, wherein said first and/or second homodimeric antibody is conjugated to a drug, a prodrug or a toxin or contains an acceptor group for the same.

According to an embodiment, the invention concerns the method, wherein the reducing conditions in step c) comprise the addition of a reducing agent.

According to an embodiment, the invention concerns the method, wherein step d) comprises removal of a reducing agent.

According to an embodiment, the invention concerns the method, wherein said first homodimeric antibody and/or second homodimeric antibody binds CD3.

According to an embodiment, the invention concerns the method, wherein said first homodimeric antibody and/or second homodimeric antibody binds CD25.

According to an embodiment, the invention concerns the method, wherein said first homodimeric antibody binds CD3 and said second homodimeric antibody binds CD25.

According to an embodiment, the invention concerns the method, wherein said heterodimeric antibody comprises a sequence of SEQ ID NO:51-69.

According to an embodiment, the invention concerns the method, wherein said heterodimeric antibody comprises a sequence with a least 70%, preferably 75%, more preferred 80%, preferably 85%, more preferred 90%, preferably 95%, more preferred 97% sequence identity to a sequence of SEQ ID NO:51-69.

According to an embodiment, the invention concerns a heterodimeric antibody obtainable by the method according to the invention.

According to an embodiment, the invention concerns a heterodimeric antibody comprising:

A first heavy chain comprising a first Fc region, said first Fc region comprising a first CH3 region selected from the group consisting of a human IgG2 CH3 region and a human IgG4 CH3 region, but with an amino acid substitution at position 405 (EU numbering), and A second heavy chain comprising a second Fc region, said second Fc region comprising a second CH3 region selected from the group consisting of a human IgG2 CH3 region and a human IgG4 CH3, but with an amino acid substitution at position 409 (EU numbering);

Wherein the sequences of the first and second CH3 regions are different. According to an embodiment, the invention concerns a heterodimeric antibody comprising:

A first heavy chain comprising a first Fc region, said first Fc region comprising a first CH3 region selected from the group consisting of a human IgG2 CH3 region and a human IgG4 CH3 region, and A second heavy chain comprising a second Fc region, said second Fc region comprising a second CH3 region selected from the group consisting of a human IgG2 CH3 region and a human IgG4 CH3, but with an amino acid substitution at position 405 and an amino acid substitution at position 409 (EU numbering);

Wherein the sequences of the first and second CH3 regions are different.

According to an embodiment, the invention concerns the heterodimeric antibody, wherein said first and/or second CH3 region is of human IgG2.

According to an embodiment, the invention concerns the heterodimeric antibody, wherein said first and/or second CH3 region is of human IgG4.

According to an embodiment, the invention concerns the heterodimeric antibody, wherein said first Fc region comprises an Arg at position 409 (EU numbering).

According to an embodiment, the invention concerns the heterodimeric antibody, wherein said second Fc region comprises a Leu at position 405 (EU numbering).

According to an embodiment, the invention concerns the heterodimeric antibody, wherein said first Fc region comprises an Arg at position 409 (EU numbering) and said second Fc region comprises a Leu at position 405 (EU numbering).

According to an embodiment, the invention concerns the heterodimeric antibody, further comprising an amino acid substitution at position 234 (EU numbering).

According to an embodiment, the invention concerns the heterodimeric antibody, further comprising an amino acid substitution at position 235 (EU numbering).

According to an embodiment, the invention concerns the heterodimeric antibody, further comprising an amino acid substitution at position 234 and/or position 235 (EU numbering).

According to an embodiment, the invention concerns the heterodimeric antibody, wherein said heterodimeric antibody comprises an Ala at position 234 (EU numbering).

According to an embodiment, the invention concerns the heterodimeric antibody, wherein said heterodimeric antibody comprises an Ala at position 235 (EU numbering).

According to an embodiment, the invention concerns the heterodimeric antibody, further comprising an amino acid substitution at position 322 (EU numbering).

According to an embodiment, the invention concerns the heterodimeric antibody, wherein said heterodimeric antibody comprises an Ala at position 322 (EU numbering).

According to an embodiment, the invention concerns the heterodimeric antibody, further comprising an amino acid substitution at position 228 (EU numbering).

According to an embodiment, the invention concerns the heterodimeric antibody, wherein said heterodimeric antibody comprises a Pro at position 228 (EU numbering).

According to an embodiment, the invention concerns the heterodimeric antibody, further comprising an amino acid substitution at position 297 (EU numbering).

According to an embodiment, the invention concerns the heterodimeric antibody, wherein said heterodimeric antibody comprises an Ala at position 297 (EU numbering).

According to an embodiment, the invention concerns the heterodimeric antibody, wherein said heterodimeric antibody comprises a hinge region.

According to an embodiment, the invention concerns the heterodimeric antibody, wherein said hinge region is selected from naturally occurring and modified hinge regions.

According to an embodiment, the invention concerns the heterodimeric antibody, wherein said hinge region is selected from the group consisting of naturally occurring IgG1, IgG2, IgG3 and IgG4 hinge regions.

According to an embodiment, the invention concerns the heterodimeric antibody, wherein said hinge region is selected from the group consisting of modified IgG1, IgG2, IgG3 and IgG4 hinge regions.

According to an embodiment, the invention concerns the heterodimeric antibody, wherein said hinge region is having at least 80%, alternatively at least 85%, alternatively at least 90%, alternatively at least 95% sequence similarity to a hinge region selected from the group consisting of naturally occurring IgG1, IgG2, IgG3 and IgG4 hinge regions.

According to an embodiment, the invention concerns the heterodimeric antibody, wherein said heterodimeric antibody comprises a hinge region selected from an IgG1 hinge region or an IgG4 hinge region with a S228P mutation.

According to an embodiment, the invention concerns the heterodimeric antibody, wherein said hinge region comprises two disulfide bonds.

According to an embodiment, the invention concerns the heterodimeric antibody, wherein said hinge region comprises a sequence of CPAP.

According to an embodiment, the invention concerns the heterodimeric antibody, wherein said hinge region comprises a sequence of SEQ ID NO: 72.

According to an embodiment, the invention concerns the heterodimeric antibody, wherein said hinge region comprises a sequence of SEQ ID NO: 72 with one amino acid substitution, one amino acid modification, one amino acid deletion or one amino acid addition.

According to an embodiment, the invention concerns the heterodimeric antibody, wherein said heterodimeric antibody comprises a CH1 region and said CH1 region comprises a Cys within the first 20 amino acid residues of said CH1 region.

According to an embodiment, the invention concerns the heterodimeric antibody, wherein said heterodimeric antibody comprises a CH1 region and said CH1 region comprises a Cys at position 14 of said CH1 region.

According to an embodiment, the invention concerns the heterodimeric antibody, wherein said heterodimeric antibody comprises a CH1 region selected from the group consisting of IgG2 CH1 regions, IgG3 CH1 regions and IgG4 CH1 regions.

According to an embodiment, the invention concerns the heterodimeric antibody, wherein said heterodimeric antibody comprises a linker.

According to an embodiment, the invention concerns the heterodimeric antibody, wherein said first heavy chain and/or said second heavy chain is chimeric, humanized, or human.

According to an embodiment, the invention concerns the heterodimeric antibody, wherein said first and second heavy chains are full-length heavy chains.

According to an embodiment, the invention concerns the heterodimeric antibody, wherein said first and second heavy chains bind different epitopes.

According to an embodiment, the invention concerns the heterodimeric antibody, wherein said first and second heavy chains are full-length heavy chains of two antibodies that bind different epitopes.

According to an embodiment, the invention concerns the heterodimeric antibody, further comprising two full-length light chains.

According to an embodiment, the invention concerns a pharmaceutical composition comprising a heterodimeric antibody according to the invention and an excipient, such as a pharmaceutically-acceptable carrier.

According to an embodiment, the invention concerns the method, wherein step c) further comprises co-expressing one or more nucleic-acid constructs encoding a light-chain in said host cell.

According to an embodiment, the invention concerns the heterodimeric antibody, wherein said first and/or second heavy chains bind CD3.

According to an embodiment, the invention concerns the heterodimeric antibody, wherein said first and/or second heavy chains bind CD25.

According to an embodiment, the invention concerns the heterodimeric antibody, wherein said first heavy chain binds CD3 and said second heavy chain binds CD25.

According to an embodiment, the invention concerns the heterodimeric antibody, wherein said heterodimeric antibody comprises a sequence selected from the group consisting of SEQ ID NO:51-69.

According to an embodiment, the invention concerns the heterodimeric antibody, wherein said heterodimeric antibody comprises a sequence with a least 70%, preferably 75%, more preferred 80%, preferably 85%, more preferred 90%, preferably 95%, more preferred 97% sequence identity to a sequence selected from the group consisting of SEQ ID NO:51-69.

According to an embodiment, the invention concerns a bispecific antibody or fragment thereof comprising a first antigen binding site capable of binding to a first antigen and a second antigen binding site capable of binding to a second antigen, wherein said first antigen binding site is comprised in a Fab fragment and said second antigen binding site is comprised in a moiety selected from the group consisting of scFv, antibody fragments and protein moiety, wherein said moiety being attached to the light chain of said Fab fragment.

According to an embodiment, the invention concerns the bispecific antibody or fragment thereof, wherein said moiety is a scFv.

According to an embodiment, the invention concerns the bispecific antibody, wherein said moiety is attached to the C-terminus or N-terminus of the light chain of said Fab fragment.

According to an embodiment, the invention concerns the bispecific antibody, wherein said moiety is attached to the C-terminus of the light chain of said Fab fragment.

According to an embodiment, the invention concerns the bispecific antibody, wherein said Fab fragment is derived from an IgG or an IgM.

According to an embodiment, the invention concerns the bispecific antibody, wherein said Fab fragment is derived from an IgG.

According to an embodiment, the invention concerns the bispecific antibody, wherein said Fab fragment is derived from an IgG selected from the group consisting of IgG1, IgG2, IgG3 and IgG4.

According to an embodiment, the invention concerns the bispecific antibody, wherein said Fab fragment is derived from an IgG2 or an IgG4.

According to an embodiment, the invention concerns the bispecific antibody, wherein said Fab fragment is derived from an IgG2 or an IgG4 as defined according to the invention.

According to an embodiment, the invention concerns the bispecific antibody, wherein said moiety is attached to a light chain of an IgG2 or IgG4 as defined according to the invention.

According to an embodiment, the invention concerns the bispecific antibody, wherein said first antigen is CD3 or CD25.

According to an embodiment, the invention concerns the bispecific antibody, wherein said second antigen is CD3 or CD25.

According to an embodiment, the invention concerns a heterodimeric antibody, preferably according to the invention, wherein said heterodimeric antibody comprises a human IgG4 Fc domain, wherein said heterodimeric antibody binds to two or more different targets and wherein said heterodimeric antibody further comprises a component selected from
(i) a Fab,
(ii) a scFv,
(iii) a variable heavy homodimer (VHH), and/or
(iv) an antibody fragment.

According to an embodiment, the invention concerns the heterodimeric antibody further comprising a S228P mutation (EU numbering) in the hinge region.

According to an embodiment, the invention concerns the heterodimeric antibody, wherein said heterodimeric antibody comprises
(i) a first Fc domain comprising native sequence in position 405-409 (EU numbering) of the CH3 domain and
(ii) a second Fc domain comprising F405L and R409K mutations (EU numbering) in the CH3 domain.

According to an embodiment, the invention concerns the heterodimeric antibody, wherein said heterodimeric antibody comprises a Fc-null mutation selected from the group consisting of V234A, N297A, and K322A (EU numbering).

According to an embodiment, the invention concerns a heterodimeric antibody, wherein said heterodimeric antibody comprises a human IgG2 Fc domain,
wherein said heterodimeric antibody binds to two or more different targets and
wherein said heterodimeric antibody further comprises a component selected from (i) a Fab,
(ii) a scFv,
(iii) a variable heavy homodimer (VHH), and/or
(iv) an antibody fragment.

According to an embodiment, the invention concerns the heterodimeric antibody, wherein the native IgG2 hinge is replaced by an IgG1 hinge or an IgG4 hinge with S228P mutation (EU numbering).

According to an embodiment, the invention concerns the heterodimeric antibody, wherein said native IgG2 hinge comprises the sequence CCVECPPCPAP (SEQ ID NO:85), said IgG1 hinge comprises the sequence DKTHTCPPCPAP (SEQ ID NO:86) and said IgG4 hinge with S228P mutation comprises the sequence YGPPCPPCPAP (SEQ ID NO:87).

According to an embodiment, the invention concerns the heterodimeric antibody, wherein said heterodimeric antibody comprises
(i) a first Fc domain comprising a K409R mutation (EU numbering) in the CH3 domain and
(ii) a second Fc domain comprising a F405L mutation (EU numbering) in the CH3 domain.

According to an embodiment, the invention concerns the heterodimeric antibody, wherein said heterodimeric antibody comprises a Fc-null mutation selected from the group consisting of F234A, L235A, N297A, and K322A (EU numbering).

According to an embodiment, the invention concerns an IgG2, IgG3 or IgG4 molecule that comprises a light chain and an antibody domain and/or protein fused to the C-terminus of said light chain, wherein said antibody domain is selected from
(i) a Fab,
(ii) a scFv,
(iii) a variable heavy homodimer (VHH), and/or
(iv) an antibody fragment.

According to an embodiment, the invention concerns the IgG2, IgG3 or IgG4 molecule further comprising a linker.

According to an embodiment, the invention concerns the IgG2, IgG3 or IgG4 molecule, wherein said linker comprises a GGGGS repeat.

According to an embodiment, the invention concerns the IgG2, IgG3 or IgG4 molecule, wherein said linker comprises a number of GGGGS repeats selected from 1, 2, 3, 4, 5, 6, 7 and 8 repeats, preferably 4-6 repeats.

According to an embodiment, the invention concerns the IgG2, IgG3 or IgG4 molecule, wherein the IgG2, IgG3 or IgG4 molecule comprises a CH1 region and said CH1 region comprises a Cys at position 14 of said CH1 region.

Immunoglobulins are glycoproteins composed of one or more units, each containing four polypeptide chains: two identical heavy chains (HCs) and two identical light chains (LCs). The amino terminal ends of the polypeptide chains show considerable variation in amino acid composition and are referred to as the variable (V) regions to distinguish them from the relatively constant (C) regions. Each light chain consists of one variable domain, VL, and one constant domain, CL. The heavy chains consist of a variable domain, VH, and three constant domains CH1, CH2 and CH3. Heavy and light chains are held together by a combination of non-covalent interactions and covalent interchain disulfide bonds, forming a bilaterally symmetric structure. The V regions of H and L chains comprise the antigen-binding sites of the immunoglobulin (Ig) molecules. Each Ig monomer contains two antigen-binding sites and is said to be bivalent.

The Fab contains one complete L chain in its entirety and the V and CH1 portion of one H chain. The Fab can be further divided into a variable fragment (Fv) composed of the VH and VL domains, and a constant fragment (Fb) composed of the CL and CH1 domains.

The H chain constant domain is generally defined as CH1-CH2-CH3 (IgG, IgA, IgD) with an additional domain (CH4) for IgM and IgE. As described above, the CH1 domain is located within the F(ab) region whereas the remaining CH domains (CH2-CH3 or CH2-CH4) comprise the Fc fragment. This Fc fragment defines the isotype and subclass of the immunoglobulin.

CH3 domain: The terms CH3 domain and CH3 region are used interchangeable herein.

CH1 domain: The terms CH1 domain and CH1 region are used interchangeable herein.

Hinge region: The hinge region is the area of the heavy chains between the first and second C region domains and is held together by disulfide bonds. A hinge region typically comprises between 10 and 30 amino acid residues. IgG hinge region sequences might be defined as the underlined sequences below:

| Construct | Hinge region sequence (underlined) |
|---|---|
| IgG1 | KS--C<u>DKTHT----------CPPCPAP</u> |
| IgG2 | K---------------<u>CCVECPPCPAP</u> |

-continued

| Construct | Hinge region sequence (underlined) |
|---|---|
| IgG3 | K<u>TPLGDTTHTPEPKSCDTPPPCPRCPAP</u> |
| IgG4 | K<u>Y--G--------------PPCPSCPAP</u> |
| V-IGG2, -A, -B (contains IgG1 hinge) | K<u>D---------------KTHTCPPCPAP</u> |
| V-IGG2-C, -D, -E (contains IgG4 hinge) | K<u>----------------YGPPCPPCPAP</u> |

Linker: A linker might be a peptide linker or a non-peptide linker. An example of a peptide linker is a Gly/Ser peptide linker comprising a five amino acid residue unit, GGGGS (SEQ ID NO:71), that can be repeated a suitable amount of times. A linker might be a naturally occurring linker or a synthetically produced linker. A linker might occur naturally in a molecule or might be synthetically added to a molecule.

Antibody fragment: As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen-binding fragment of an antibody may be produced by any means. For example, an antigen-binding fragment of an antibody may be enzymatically or chemically produced by fragmentation of an intact antibody and/or it may be recombinantly produced from a gene encoding the partial antibody sequence. Alternatively or additionally, antigen-binding fragment of an antibody may be wholly or partially synthetically produced. An antigen-binding fragment of an antibody may optionally comprise a single chain antibody fragment. Alternatively or additionally, an antigen-binding fragment of an antibody may comprise multiple chains that are linked together, for example, by disulfide linkages. An antigen-binding fragment of an antibody may optionally comprise a multi-molecular complex. A functional antibody fragment typically comprises at least about 50 amino acids and more typically comprises at least about 200 amino acids.

Antibody or fragment thereof: As used herein, an "antibody or fragment thereof" refers to an antibody or antibody fragment as defined above.

Humanized antibodies: Humanized antibodies are antibodies from non-human species whose protein sequences have been modified to increase their similarity to antibody variants produced naturally in humans.

Single-chain Fv (scFv): Single-chain Fvs (scFvs) are widely known and used in the art. A single-chain Fv is a fusion protein of the variable regions of the heavy (VH) and light chains (VL) of immunoglobulins, often connected by a short linker peptide (see, e.g., see, e.g., Benny K. C. Lo (ed.), Antibody Engineering—Methods and Protocols, Humana Press 2004, and references cited therein).

The light chains of immunoglobulins can be a lambda (λ) or kappa (κ) chain. Lambda light chain sequence and kappa light chain sequence might be defined as below:

| Construct | Sequence |
|---|---|
| IGKC HUMAN Immunoglobulin kappa constant | RTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVT KSFNRGEC (SEQ ID NO: 88) |
| IGLC1 HUMAN Immunoglobulin lambda constant 1 | GQPKANPTVTLFPPSSEELQANKATLVCLISDF YPGAVTVAWKADGSPVKAGVETTKPSKQSNNKY AASSYLSLTPEQWKSHRSYSCQVTHEGSTVEKT VAPTECS (SEQ ID NO: 89) |
| IGLC2 HUMAN Immunoglobulin lambda constant 2 | GQPKAAPSVTLFPPSSEELQANKATLVCLISDF YPGAVTVAWKADSSPVKAGVETTTPSKQSNNKY AASSYLSLTPEQWKSHRSYSCQVTHEGSTVEKT VAPTECS (SEQ ID NO: 90) |
| IGLC3 HUMAN Immunoglobulin lambda constant 3 | GQPKAAPSVTLFPPSSEELQANKATLVCLISDF YPGAVTVAWKADSSPVKAGVETTTPSKQSNNKY AASSYLSLTPEQWKSHKSYSCQVTHEGSTVEKT VAPTECS (SEQ ID NO: 91) |
| IGLC6 HUMAN Immunoglobulin lambda constant 6 | GQPKAAPSVTLFPPSSEELQANKATLVCLISDF YPGAVKVAWKADGSPVNTGVETTTPSKQSNNKY AASSYLSLTPEQWKSHRSYSCQVTHEGSTVEKT VAPAECS (SEQ ID NO: 92) |
| IGLC7 HUMAN Immunoglobulin lambda constant 7 | GQPKAAPSVTLFPPSSEELQANKATLVCLVSDF NPGAVTVAWKADGSPVKVGVETTKPSKQSNNKY AASSYLSLTPEQWKSHRSYSCRVTHEGSTVEKT VAPAECS (SEQ ID NO: 93) |

Throughout this application, "EU numbering" refers to numbering according to the EU Index.

A psycho-immune disorder may be understood as a psychiatric disorder caused and/or affected by inflammation, and/or an inflammatory disorder caused and/or affected by a psychiatric disorder.

A mood disorder may be defined as a general emotional state or mood that is distorted or inconsistent with the circumstances and interferes with a subject's ability to function. A subject may be extremely sad, empty or irritable (depressed), or may have periods of depression alternating with being excessively happy (mania). A mood disorder may also be understood as a disorder classified by the American Psychiatric Association's Diagnostic and Statistical Manual of Mental Disorders (DSM-V).

According to an embodiment, the invention concerns an antibody or fragment thereof comprising a variable light chain sequence with at least 82% identity to a human germline variable light chain sequence.

According to an embodiment, the invention concerns an antibody or fragment thereof comprising a variable light chain sequence with at least 83%, alternatively at least 84%, alternatively at least 85%, alternatively at least 86%, alternatively at least 87% identity to a human germline variable light chain sequence.

According to an embodiment, the invention concerns an antibody or fragment thereof comprising a variable heavy chain sequence with at least 80% identity to a human germline variable heavy chain sequence.

According to an embodiment, the invention concerns antibody or fragment thereof comprising a variable heavy chain sequence with at least 80%, alternatively at least 81%, alternatively at least 82%, alternatively at least 83%, alternatively at least 84%, alternatively at least 85%, alternatively at least 86%, alternatively at least 87%, alternatively at least 88%, alternatively at least 89% identity to a human germline variable heavy chain sequence.

According to an embodiment, the invention concerns an antibody or fragment thereof comprising a variable light chain sequence with at least 70% identity to a human germline variable light chain sequence According to an embodiment, the invention concerns an antibody or fragment thereof comprises a variable light chain sequence with at least 70%, alternatively at least 75%, alternatively at least 80%, alternatively at least 81%, alternatively at least 82%, alternatively at least 83%, alternatively at least 84% identity to a human germline variable light chain sequence.

According to an embodiment, the invention concerns an antibody or fragment thereof comprises a variable heavy chain sequence with at least 70% identity to a human germline variable heavy chain sequence.

According to an embodiment, the invention concerns an antibody or fragment thereof comprises a variable heavy chain sequence with at least 70%, alternatively at least 75%, alternatively at least 80%, alternatively at least 81%, alternatively at least 82%, alternatively at least 83%, alternatively at least 84%, alternatively at least 85%, alternatively at least 86% identity to a human germline variable heavy chain sequence.

According to an embodiment, the invention concerns an antibody or fragment thereof, wherein the antigen contact residues are determined using IMGT.

FIGURES

FIG. 1 shows a schematic representation of monospecific and bispecific antibodies. VIT-100 is a 4 chain IgG anti-CD3 monospecific antibody, VIT-101 is a 4 chain IgG anti-CD25 monospecific antibody, VIT-102 is a 4 chain IgG antiCD3/anti-CD25 bispecific antibody, VIT-103 is a 2 chain scFv-Fc anti-CD3 monospecific antibody, VIT-104 is a 2 chain scFv-Fc anti-CD25 monospecific antibody and VIT-105 is 2 chain scFv-Fc anti-CD3/anti-CD25 bispecific antibody.

Figure 2:
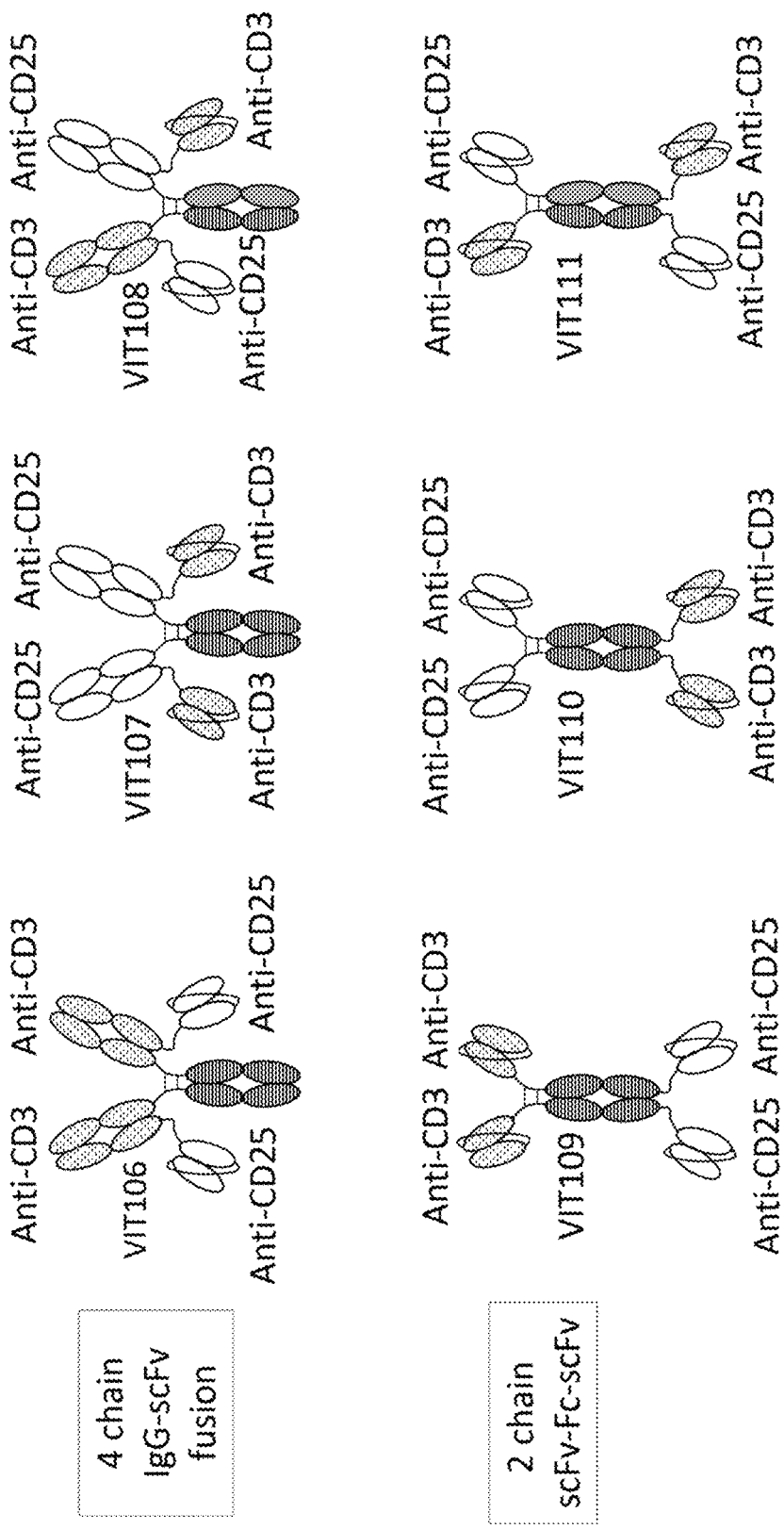

FIG. 2 shows a schematic representation of 2+2 bispecific antibodies. VIT106-108 are 4 chain IgG-scFv fusion anti-CD3/anti-CD25 bispecific antibodies and VIT-109-111 are 2 chain scFv-Fc-scFv anti-CD3/anti-CD25 bispecific antibodies.

All cited references are incorporated by reference.

The accompanying Figures and Examples are provided to explain rather than limit the present invention. It will be clear to the person skilled in the art that aspects, embodiments, claims and any items of the present invention may be combined.

Unless otherwise mentioned, all percentages are in weight/weight. Unless otherwise mentioned, all measurements are conducted under standard conditions (ambient temperature and pressure). Unless otherwise mentioned, test conditions are according to European Pharmacopoeia 8.0.

EXAMPLES

Example 1: Design of Humanized Anti-CD3 Sequences

A proposed sequence for a humanized anti-CD3 murine mAb muromomab (OKT3) is hereby provided as follows.

The sequence of anti-CD3 murine mAb muromomab (OKT3) is shown below, antigen contact residues are shown in bold and IMGT CDR sequences are underlined.

```
VL:                                       (SEQ ID NO: 1)
QIVLICISPAIMSASPGEKVTMTCSASSSVSYMNWYQQKSGTSPKRWIYD

TSKLASGVPAHFRGSGSGTSYSLTISGMEAEDAATYYCQQWSSNPFTFGS

GTKLEIN

VH:                                       (SEQ ID NO: 6)
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSS
```

All contact residues were retained in the humanized sequences. It was noted that the previous humanized OKT3 sequence found in Teplizumab did not retain the non-CDR contact residue H:K82 (IMGT numbering).

All IMGT CDR residues were retaining with the exception of an unpaired H:Cys114 (IMGT numbering) in H:CDR3, which was mutated to Ser in the humanized constructs. The Cys was not a contact residue and it is speculated that it causes aggregation of the humanized products.

Humanizing mutations were made based on identity to human germline sequence or prevalence in human antibody sequences. Final constructs are presented in Table 1 and Table 2.

TABLE 1

Anti-CD3 VL sequences

| Construct | Sequence | % human germline | Predicted immunogenic peptides | Notes |
|---|---|---|---|---|
| mOKT3 VL | QIVLTQSPAIMSAS PGEKVTMTCSASSS VSYMNWYQQKSG TSPKRWIYDTSKLA SGVPAHFRGSGSG TSYSLTISGMEAED AATYYCQQWSSNP FTFGSGTKLEIN (SEQ ID NO: 1) | 61.1% IGKV3-11*01 | QIVLTQSPAIMSASP | |

TABLE 1-continued

Anti-CD3 VL sequences

| Construct | Sequence | % human germline | Predicted immunogenic peptides | Notes |
|---|---|---|---|---|
| Teplizumab VL | DIQMTQSPSSLSAS VGDRVTITCSASSS VSYMNWYQQTPG KAPKRWIYDTSKLA SGVPSRFSGSGSGT DYTFTISSLQPEDIA TYYCQQWSSNPFT FGQGTKLQIT (SEQ ID NO: 2) | 81.1% IGKV1-33*01 | none | |
| VCD3-L1 | DIQMTQSPSSLSAS VGDRVTITCQASSS VSYMNWYQQKPG KAPKRWIYDTSKLA SGVPSRFSGSGSGT DYTFTISSLQPEDIA TYYCQQWSSNPFT FGQGTKLEIK (SEQ ID NO: 3) | 83.2% IGKV1-33*01 | none | Based on germline IGKV1-33 |
| VCD3-L2 | EIVLTQSPATLSLSP GERATLSCRASSSV SYMNWYQQKPGQ APRRLIYDTSKRAT G I PARFSGSGSGTD YTLTISSLEPEDAAV YYCQQWSSNPFTF GQGTKLEIK (SEQ ID NO: 4) | 87.4% IGKV3-11*01 | EI<u>VLTQSPATLSLSP</u> QAP<u>RRLIYDTSKRAT</u> | Based on germline IGKV3-11 |
| VCD3-L3 | EIQLTQSPATLSLSP GERATLSCRASSSV SYMNWYQQKPGQ APRRWIYDTSKLAT GIPARFSGSGSGTD YTLTISSLEPEDAAV YYCQQWSSNPFTF GQGTKLEIK (SEQ ID NO: 5) | 84.2% IGKV3-11*01 | none | Removed immunogenic epitopes In V2 |

TABLE 2

Anti-CD3 VH sequences

| Construct | Sequence | % human germline | Predicted immunogenic peptides | Notes |
|---|---|---|---|---|
| mOKT3 VH | QVQLQQSGAELA RPGASVKMSCKA SGYTFTRYTMHW VKQRPGQGLEWI GYINPSRGYTNYN QKFKDKATLTTDK SSSTAYMQLSSLTS EDSAVYYCARYYD DHYCLDYWGQGT TLTVSS (SEQ ID NO: 6) | 72.4% IGHV1-46*01 | <u>GYITTRYTMHINVK QR</u> | |
| Teplizumab VH | QVQLVQSGGGVV QPGRSLRLSCKAS GYTFTRYTMHWV RQAPGKGLEWIG YINPSRGYTNYNQ KVKDRFTISRDNS KNTAFLQMDSLRP EDTGVYFCARYYD | 72.4% IGHV3-30*10 | <u>RYTMHWVRQAPGK GL</u> <u>KNTAFLQMDSLRPE D</u> | |

TABLE 2-continued

Anti-CD3 VH sequences

| Construct | Sequence | % human germline | Predicted immunogenic peptides | Notes |
|---|---|---|---|---|
| | DHYCLDYWGQGT PVTVSS (SEQ ID NO: 7) | | | |
| VCD3-H1 | QVQLVQSGGGVV QPGRSLRLSCAAS GYTFTRYTMHWV RQAPGKGLEWVG YINPSRGYTNYTD SVKGRFTISTDKSK NTAYLQMNSLRA EDTAVYYCARYYD DHYSLDYWGQGT TVTVSS (SEQ ID NO: 8) | 81.6% IGHV3-30*10 | RYTMHWVRQAPGK GL KNTAYLQMNSLRAE D | Based on germline IGHV3-30 |
| VCD3-H2 | QVQLVQSGAEVK KPGASVKVSCKAS GYTFTRYTMHWV RQAPGQGLEWM GYINPSRGYTNYN QKFQGRVTMTTD KSTSTAYMELSSLR SEDTAVYYCARYY DDHYSLDYWGQG TTVTVSS (SEQ ID NO: 9) | 89.8% IGHV1-46*01 | RYTMHVRQAPG QGL | Based on germline IGHV1-46 |
| VCD3-H3 | QVQLVQSGAEVK KPGASVKVSCKAS GYTFTRYTMHWV RQSPGQGLEWM GYINPSRGYTNYN QKFQGRVTMTTD KSTSTAYMELSSLR SEDTAVYYCARYY DDHYSLDYWGQG TTVTVSS (SEQ ID NO: 10) | 88.8% IGHV1-46*01 | none | Removed immunogenic epitopes in V2 |

Single chain variable fragments (scFv) were designed based on a VH-VL orientation and are presented in Table 3. Additional disulfide stabilization between the VH and VL domains was engineered by substituting Cys at positions VH44-VL100 (Kabat numbering).

TABLE 3

Anti-CD3 scFv sequences

| Construct | Sequence |
|---|---|
| VCD3-H1L1 | QVQLVQSGGGVVQPGRSLRLSCAASGYTFTRYTMHWVRQAPGKGLEWVGYINPSRGYTNYNDSV KGRFTISTDKSKNTAYLQMNSLRAEDTAVYYCARYYDDHYSLDYWGQGTTVTVSSGGGGSGGGGS GGGGSGGGGSGGGGSGGGGS DIQMTQSPSSLSASVGDRVTITCQASSSVSYMNWYQQKPGKAPKRWIYDTSKLASGVPSRFSGSGS GTDYTFTISSLQPEDIATYYCQQWSSNPFTFGQGTKLEIK (SEQ ID NO: 11) |
| VCD3-H1L1-DS | QVQLVQSGGGVVQPGRSLRLSCAASGYTFTRYTMHWVRQAPGKCLEWVGYINPSRGYTNYNDSV KGRFTISTDKSKNTAYLQMNSLRAEDTAVYYCARYYDDHYSLDYWGQGTTVTVSSGGGGSGGGGS GGGGSGGGGSGGGGSGGGGS DIQMTQSPSSLSASVGDRVTITCQASSSVSYMNWYQQKPGKAPKRWIYDTSKLASGVPSRFSGSGS GTDYTFTISSLQPEDIATYYCQQWSSNPFTFGCGTKLEIK (SEQ ID NO: 12) |
| VCD3-H1L2 | QVQLVQSGGGVVQPGRSLRLSCAASGYTFTRYTMHWVRQAPGKGLEWVGYINPSRGYTNYNDSV KGRFTISTDKSKNTAYLQMNSLRAEDTAVYYCARYYDDHYSLDYWGQGTTVTVSSGGGGSGGGGS GGGGSGGGGSGGGGSGGGGS EIVLTQSPATLSLSPGERATLSCRASSSVSYMNWYQQKPGQAPRRLIYDTSKRATGIPARFSGSGSGT DYTLTISSLEPEDAAVYYCQQWSSNPFTFGQGTKLEIK (SEQ ID NO: 13) |

TABLE 3-continued

Anti-CD3 scFv sequences

| Construct | Sequence |
|---|---|
| VCD3-H1L2-DS | QVQLVQSGGGVVQPGRSLRLSCAASGYTFTRYTMHWVRQAPGKCLEWVGYINPSRGYTNYNDSV<br>KGRFTISTDKSKNTAYLQMNSLRAEDTAVYYCARYYDDHYSLDYWGQGTTVTVSSGGGGSGGGGS<br>*GGGGSGGGGSGGGGSGGGGS*<br>EIVLTQSPATLSLSPGERATLSCRASSSVSYMNWYQQKPGQAPRRLIYDTSKRATGIPARFSGSGSGT<br>DYTLTISSLEPEDAAVYYCQQWSSNPFTFGCGTKLEIK (SEQ ID NO: 14) |
| VCD3-H1L3 | QVQLVQSGGGVVQPGRSLRLSCAASGYTFTRYTMHWVRQAPGKGLEWVGYINPSRGYTNYNDSV<br>KGRFTISTDKSKNTAYLQMNSLRAEDTAVYYCARYYDDHYSLDYWGQGTTVTVSSGGGGSGGGGS<br>*GGGGSGGGGSGGGGSGGGGS*<br>EIQLTQSPATLSLSPGERATLSCRASSSVSYMNWYQQKPGQAPRRWIYDTSKLATGIPARFSGSGSGT<br>DYTLTISSLEPEDAAVYYCQQWSSNPFTFGCGTKLEIK (SEQ ID NO: 15) |
| VCD3-H1L3-DS | QVQLVQSGGGVVQPGRSLRLSCAASGYTFTRYTMHWVRQAPGKCLEWVGYINPSRGYTNYNDSV<br>KGRFTISTDKSKNTAYLQMNSLRAEDTAVYYCARYYDDHYSLDYWGQGTTVTVSSGGGGSGGGGS<br>*GGGGSGGGGSGGGGSGGGGS*<br>EIQLTQSPATLSLSPGERATLSCRASSSVSYMNWYQQKPGQAPRRWIYDTSKLATGIPARFSGSGSGT<br>DYTLTISSLEPEDAAVYYCQQWSSNPFTFGCGTKLEIK (SEQ ID NO: 16) |
| VCD3-H2L1 | QVQLVQSGAEVKKPGASVKVSCKASGYTFTRYTMHWVRQAPGQGLEWMGYINPSRGYTNYNQKF<br>QGRVTMTTDKSTSTAYMELSSLRSEDTAVYYCARYYDDHYSLDYWGQGTTVTVSSGGGGSGGGGS<br>*GGGGSGGGGSGGGGSGGGGS*<br>DIQMTQSPSSLSASVGDRVTITCQASSSVSYMNWYQQKPGKAPKRWIYDTSKLASGVPSRFSGSGS<br>GTDYTFTISSLQPEDIATYYCQQWSSNPFTFGQGTKLEIK (SEQ ID NO: 17) |
| VCD3-H2L1-DS | QVQLVQSGAEVKKPGASVKVSCKASGYTFTRYTMHWVRQAPGQCLEWMGYINPSRGYTNYNQKF<br>QGRVTMTTDKSTSTAYMELSSLRSEDTAVYYCARYYDDHYSLDYWGQGTTVTVSSGGGGSGGGGS<br>*GGGGSGGGGSGGGGSGGGGS*<br>DIQMTQSPSSLSASVGDRVTITCQASSSVSYMNWYQQKPGKAPKRWIYDTSKLASGVPSRFSGSGS<br>GTDYTFTISSLQPEDIATYYCQQWSSNPFTFGQGTKLEIK (SEQ ID NO: 18) |
| VCD3-H2L2 | QVQLVQSGAEVKKPGASVKVSCKASGYTFTRYTMHWVRQAPGQGLEWMGYINPSRGYTNYNQKF<br>QGRVTMTTDKSTSTAYMELSSLRSEDTAVYYCARYYDDHYSLDYWGQGTTVTVSSGGGGSGGGGS<br>*GGGGSGGGGSGGGGSGGGGS*<br>EIVLTQSPATLSLSPGERATLSCRASSSVSYMNWYQQKPGQAPRRLIYDTSKRATGIPARFSGSGSGT<br>DYTLTISSLEPEDAAVYYCQQWSSNPFTFGCGTKLEIK (SEQ ID NO: 19) |
| VCD3-H2L2-DS | QVQLVQSGAEVKKPGASVKVSCKASGYTFTRYTMHWVRQAPGQCLEWMGYINPSRGYTNYNQKF<br>QGRVTMTTDKSTSTAYMELSSLRSEDTAVYYCARYYDDHYSLDYWGQGTTVTVSSGGGGSGGGGS<br>*GGGGSGGGGSGGGGSGGGGS*<br>EIVLTQSPATLSLSPGERATLSCRASSSVSYMNWYQQKPGQAPRRLIYDTSKRATGIPARFSGSGSGT<br>DYTLTISSLEPEDAAVYYCQQWSSNPFTFGCGTKLEIK (SEQ ID NO: 20) |
| VCD3-H2L3 | QVQLVQSGAEVKKPGASVKVSCKASGYTFTRYTMHWVRQAPGQGLEWMGYINPSRGYTNYNQKF<br>QGRVTMTTDKSTSTAYMELSSLRSEDTAVYYCARYYDDHYSLDYWGQGTTVTVSSGGGGSGGGGS<br>*GGGGSGGGGSGGGGSGGGGS*<br>EIQLTQSPATLSLSPGERATLSCRASSSVSYMNWYQQKPGQAPRRWIYDTSKLATGIPARFSGSGSGT<br>DYTLTISSLEPEDAAVYYCQQWSSNPFTFGCGTKLEIK (SEQ ID NO: 21) |
| VCD3-H2L3-DS | QVQLVQSGAEVKKPGASVKVSCKASGYTFTRYTMHWVRQAPGQCLEWMGYINPSRGYTNYNQKF<br>QGRVTMTTDKSTSTAYMELSSLRSEDTAVYYCARYYDDHYSLDYWGQGTTVTVSSGGGGSGGGGS<br>*GGGGSGGGGSGGGGSGGGGS*<br>EIQLTQSPATLSLSPGERATLSCRASSSVSYMNWYQQKPGQAPRRWIYDTSKLATGIPARFSGSGSGT<br>DYTLTISSLEPEDAAVYYCQQWSSNPFTFGCGTKLEIK (SEQ ID NO: 22) |
| VCD3-H3L1 | QVQLVQSGAEVKKPGASVKVSCKASGYTFTRYTMHWVRQSPGQGLEWMGYINPSRGYTNYNQKF<br>QGRVTMTTDKSTSTAYMELSSLRSEDTAVYYCARYYDDHYSLDYWGQGTTVTVSSGGGGSGGGGS<br>*GGGGSGGGGSGGGGSGGGGS*<br>DIQMTQSPSSLSASVGDRVTITCQASSSVSYMNWYQQKPGKAPKRWIYDTSKLASGVPSRFSGSGS<br>GTDYTFTISSLQPEDIATYYCQQWSSNPFTFGQGTKLEIK (SEQ ID NO: 23) |
| VCD3-H3L1-DS | QVQLVQSGAEVKKPGASVKVSCKASGYTFTRYTMHWVRQSPGQCLEWMGYINPSRGYTNYNQKF<br>QGRVTMTTDKSTSTAYMELSSLRSEDTAVYYCARYYDDHYSLDYWGQGTTVTVSSGGGGSGGGGS<br>*GGGGSGGGGSGGGGSGGGGS*<br>DIQMTQSPSSLSASVGDRVTITCQASSSVSYMNWYQQKPGKAPKRWIYDTSKLASGVPSRFSGSGS<br>GTDYTFTISSLQPEDIATYYCQQWSSNPFTFGQGTKLEIK (SEQ ID NO: 24) |
| VCD3-H3L2 | QVQLVQSGAEVKKPGASVKVSCKASGYTFTRYTMHWVRQSPGQGLEWMGYINPSRGYTNYNQKF<br>QGRVTMTTDKSTSTAYMELSSLRSEDTAVYYCARYYDDHYSLDYWGQGTTVTVSSGGGGSGGGGS<br>*GGGGSGGGGSGGGGSGGGGS*<br>EIVLTQSPATLSLSPGERATLSCRASSSVSYMNWYQQKPGQAPRRLIYDTSKRATGIPARFSGSGSGT<br>DYTLTISSLEPEDAAVYYCQQWSSNPFTFGCGTKLEIK (SEQ ID NO: 25) |
| VCD3-H3L2-DS | QVQLVQSGAEVKKPGASVKVSCKASGYTFTRYTMHWVRQSPGQCLEWMGYINPSRGYTNYNQKF<br>QGRVTMTTDKSTSTAYMELSSLRSEDTAVYYCARYYDDHYSLDYWGQGTTVTVSSGGGGSGGGGS<br>*GGGGSGGGGSGGGGSGGGGS* |

TABLE 3-continued

Anti-CD3 scFv sequences

| Construct | Sequence |
|---|---|
| | EIVLTQSPATLSLSPGERATLSCRASSSVSYMNWYQQKPGQAPRRLIYDTSKRATGIPARFSGSGT DYTLTISSLEPEDAAVYYCQQWSSNPFTFGCGTKLEIK (SEQ ID NO: 26) |
| VCD3-H3L3 | QVQLVQSGAEVKKPGASVKVSCKASGYTFTRYTMHWVRQSPGQGLEWMGYINPSRGYTNYNQKF QGRVTMTTDKSTSTAYMELSSLRSEDTAVYYCARYYDDHYSLDYWGQGTTVTVSSGGGGSGGGGS GGGGSGGGGSGGGGSGGGGS EIQLTQSPATLSLSPGERATLSCRASSSVSYMNWYQQKPGQAPRRWIYDTSKLATGIPARFSGSGT DYTLTISSLEPEDAAVYYCQQWSSNPFTFGCGTKLEIK (SEQ ID NO: 27) |
| VCD3-H3L3-DS | QVQLVQSGAEVKKPGASVKVSCKASGYTFTRYTMHWVRQSPGQCLEWMGYINPSRGYTNYNQKF QGRVTMTTDKSTSTAYMELSSLRSEDTAVYYCARYYDDHYSLDYWGQGTTVTVSSGGGGSGGGGS GGGGSGGGGSGGGGSGGGGS EIQLTQSPATLSLSPGERATLSCRASSSVSYMNWYQQKPGQAPRRWIYDTSKLATGIPARFSGSGT DYTLTISSLEPEDAAVYYCQQWSSNPFTFGCGTKLEIK (SEQ ID NO: 28) |

Example 2: Design of Humanized Anti-CD25 Sequences

A proposed sequence for a humanized anti-CD25 chimeric mAb basiliximab is hereby provided as follows.

The sequence of anti-CD25 chimeric mAb basiliximab is shown below, antigen contact residues are shown in bold and IMGT CDR sequences are underlined.

VH: (SEQ ID NO: 29)
QVQLQQSGTVLARPGASVKMSCKAS<u>GYSFTRYW</u>HWIKQRPGQGLEWIGA<u>I</u>

<u>YPGNSDT</u>SYNQKFEGKAKLTAVISASTAYMELSSLTHEDSAVYYC<u>SRDYG</u>

<u>YYFDF</u>WGQGTTLIVSS

VL: (SEQ ID NO: 32)
QIVSTQSPAIMSASPGEKVTMTCSAS<u>SSRSY</u>MQWYQQKPGTSPKRWIY<u>DT</u>

<u>S</u>KLASGVPARFSGSGSGTSYSLTISSMEAEDAATYYC<u>HQ</u><u>RSSYT</u>FGGGTK

LEIK

All contact residues and IMGT CDR sequences were retained in the humanized sequences.

Humanizing mutations were made based on identity to human germline sequence or prevalence in human antibody sequences. Final constructs are presented in Table 4 and Table 5.

TABLE 4

Anti-CD25 VH sequences

| Construct | Sequence | % human V-region | Predicted immunogenic peptides | Notes |
|---|---|---|---|---|
| mBasil VH | QVQLQQSGTVLARPGAS VKMSCKASGYSFTRYW MHWIKQRPGQGLEWIG AIYPGNSDTSYNQKFEGK AKLTAVTSASTAYMELSS LTHEDSAVYYCSRDYGYY FDFWGQGTTLTVSS (SEQ ID NO: 29) | 66.3% HV1-3*01 | GYSFTR<u>YWMHWKQR</u> | |
| VCD25-H1 | QVQLVQSGAGVAKPGA SVKVSCKASGYSFTRYW MHWVRQPPGQGLEW MGAIYPGNSDTSYSQKF EGRVTITADTSASTAYME LSSLRSEDTAVYYCSRDY GYYFDFWGQGTTVTVSS (SEQ ID NO: 30) | 83.7% HV1-3*01 | none | |

TABLE 4-continued

Anti-CD25 VH sequences

| Construct | Sequence | % human V-region | Predicted immunogenic peptides | Notes |
|---|---|---|---|---|
| VCD25-H2 | QVQLVQSGAEVKKPGAS VKVSCKASGYSFTRYWM HWVRQPPGQRLEWMG AIYPGNSDTSYSQKFEGR VTITADTSASTAYMELSSL RSEDTAVYYCSRDYGYYF DFWGQGTTVTVSS (SEQ ID NO: 31) | 86.7% HV1-3*01 | none | |

TABLE 5

Anti-CD25 VL sequences

| Construct | Sequence | % human germline | Predicted immunogenic peptides | Notes |
|---|---|---|---|---|
| mBasil VL | QIVSTQSPAIMSASPGE KVTMTCSASSSRSYMQ WYQQKPGTSPKRWIYD TSKLASGVPARFSGSGS GTSYSLTISSMEAEDAA TYYCHQRSSYTFGGGTK LEIK (SEQ ID NO:32) | 64.5% IGKV6-21*02 | none | |
| VCD25-L1 | QIVSTQSPDTQSVTPKE KVTITCRASSSRSYMQ WYQQKPDQSPKRWIY DTSKSASGVPSRFSGSG SGTDYTLTINSLEAEDAA TYYCHQRSSYTFGQGTK LEIK (SEQ ID NO: 33) | 80.6% IGKV6-21*02 | none | |
| VCD25-L2 | EIVLTQSPDFQSVTPKEK VTITCRASSSRSYMQWY QQKPDQSPKRLIYDTSK SASGVPSRFSGSGSGTD YTLTINSLEAEDAATYYC HQRSSYTFGQGTKLEIK (SEQ ID NO: 34) | 84.9% IGKV6-21*02 | none | |

Single chain variable fragments (scFv) were designed based on a VH-VL and VL-VH orientations and are presented in Table 6. Additional disulfide stabilization between the VH and VL domains was engineered by substituting Cys at positions VH44-VL100 (Kabat numbering).

TABLE 6

Anti-CD25 scFv sequences

| Construct | Sequence |
|---|---|
| VCD25-H1L1 | QVQLVQSGAGVAKPGASVKVSCKASGYSFTRYWMHWVRQPPGQGLEWMGAIYPGNSDTSYSQK FEGRVTITADTSASTAYMELSSLRSEDTAVYYCSRDYGYYFDFWGQGTTVTVSS *GGGGSGGGGSGGGGSGGGGSGGGGSGGGGS* QIVSTQSPDTQSVTPKEKVTITCRASSSRSYMQWYQQKPDQSPKRWIYDTSKSASGVPSRFSGSGSG TDYTLTINSLEAEDAATYYCHQRSSYTFGQGTKLEIK (SEQ ID NO: 35) |
| VCD25-H1L1-DS | QVQLVQSGAGVAKPGASVKVSCKASGYSFTRYWMHWVRQPPGQGLEWMGAIYPGNSDTSYSQK FEGRVTITADTSASTAYMELSSLRSEDTAVYYCSRDYGYYFDFWGQCTIVIVSS *GGGGSGGGGSGGGGSGGGGSGGGGSGGGGS* QIVSTQSPDTQSVTPKEKVTITCRASSSRSYMQWYQQKPDQSPKRWIYDTSKSASGVPSRFSGSGSG TDYTLTINSLEAEDAATYYCHQRSSYTFGCGTKLEIK (SEQ ID NO: 36) |

TABLE 6-continued

Anti-CD25 scFv sequences

| Construct | Sequence |
|---|---|
| VCD25-H1L2 | QVQLVQSGAGVAKPGASVKVSCKASGYSFTRYWMHWVRQPPGQGLEWMGAIYPGNSDTSYSQK FEGRVTITADTSASTAYMELSSLRSEDTAVYYCSRDYGYYFDFWGQGTTVTVSS *GGGGSGGGGSGGGGSGGGGSGGGGSGGGGS* EIVLTQSPDFQSVTPKEKVTITCRASSSRSYMQWYQQKPDQSPKRLIYDTSKSASGVPSRFSGSGSGT DYTLTINSLEAEDAATYYCHQRSSYTFGQGTKLEIK (SEQ ID NO: 37) |
| VCD25-H1L2-DS | QVQLVQSGAGVAKPGASVKVSCKASGYSFTRYWMHWVRQPPGQCLEWMGAIYPGNSDTSYSQK FEGRVTITADTSASTAYMELSSLRSEDTAVYYCSRDYGYYFDFWGQGTTVTVSS *GGGGSGGGGSGGGGSGGGGSGGGGSGGGGS* EIVLTQSPDFQSVTPKEKVTITCRASSSRSYMQWYQQKPDQSPKRLIYDTSKSASGVPSRFSGSGSGT DYTLTINSLEAEDAATYYCHQRSSYTFGCGTKLEIK (SEQ ID NO: 38) |
| VCD25-H2L1 | QVQLVQSGAEVKKPGASVKVSCKASGYSFTRYWMHWVRQPPGQRLEWMGAIYPGNSDTSYSQKF EGRVTITADTSASTAYMELSSLRSEDTAVYYCSRDYGYYFDFWGQGTTVTVSS *GGGGSGGGGSGGGGSGGGGSGGGGSGGGGS* QIVSTQSPDTQSVTPKEKVTITCRASSSRSYMQWYQQKPDQSPKRWIYDTSKSASGVPSRFSGSGSG TDYTLTINSLEAEDAATYYCHQRSSYTFGQGTKLEIK (SEQ ID NO: 39) |
| VCD25-H2L1-DS | QVQLVQSGAEVKKPGASVKVSCKASGYSFTRYWMHWVRQPPGQCLEWMGAIYPGNSDTSYSQKF EGRVTITADTSASTAYMELSSLRSEDTAVYYCSRDYGYYFDFWGQGTTVTVSS *GGGGSGGGGSGGGGSGGGGSGGGGSGGGGS* QIVSTQSPDTQSVTPKEKVTITCRASSSRSYMQWYQQKPDQSPKRWIYDTSKSASGVPSRFSGSGSG TDYTLTINSLEAEDAATYYCHQRSSYTFGCGTKLEIK (SEQ ID NO: 40) |
| VCD25-H2L2 | QVQLVQSGAEVKKPGASVKVSCKASGYSFTRYWMHWVRQPPGQRLEWMGAIYPGNSDTSYSQKF EGRVTITADTSASTAYMELSSLRSEDTAVYYCSRDYGYYFDFWGQGTTVTVSS *GGGGSGGGGSGGGGSGGGGSGGGGSGGGGS* EIVLTQSPDFQSVTPKEKVTITCRASSSRSYMQWYQQKPDQSPKRLIYDTSKSASGVPSRFSGSGSGT DYTLTINSLEAEDAATYYCHQRSSYTFGQGTKLEIK (SEQ ID NO: 41) |
| VCD25-H2L2-DS | QVQLVQSGAEVKKPGASVKVSCKASGYSFTRYWMHWVRQPPGQCLEWMGAIYPGNSDTSYSQKF EGRVTITADTSASTAYMELSSLRSEDTAVYYCSRDYGYYFDFWGQGTTVTVSS *GGGGSGGGGSGGGGSGGGGSGGGGSGGGGS* EIVLTQSPDFQSVTPKEKVTITCRASSSRSYMQWYQQKPDQSPKRLIYDTSKSASGVPSRFSGSGSGT DYTLTINSLEAEDAATYYCHQRSSYTFGCGTKLEIK (SEQ ID NO: 42) |
| VCD25-L1H1 | QIVSTQSPDTQSVTPKEKVTITCRASSSRSYMQWYQQKPDQSPKRWIYDTSKSASGVPSRFSGSGSG TDYTLTINSLEAEDAATYYCHQRSSYTFGQGTKLEIK *GGGGSGGGGSGGGGSGGGGSGGGGSGGGGS* QVQLVQSGAGVAKPGASVKVSCKASGYSFTRYWMHWVRQPPGQGLEWMGAIYPGNSDTSYSQK FEGRVTITADTSASTAYMELSSLRSEDTAVYYCSRDYGYYFDFWGQGTTVTVSS (SEQ ID NO: 43) |
| VCD25-L1H1-DS | QIVSTQSPDTQSVTPKEKVTITCRASSSRSYMQWYQQKPDQSPKRWIYDTSKSASGVPSRFSGSGSG TDYTLTINSLEAEDAATYYCHQRSSYTFGCGTKLEIK *GGGGSGGGGSGGGGSGGGGSGGGGSGGGGS* QVQLVQSGAGVAKPGASVKVSCKASGYSFTRYWMHWVRQPPGQCLEWMGAIYPGNSDTSYSQK FEGRVTITADTSASTAYMELSSLRSEDTAVYYCSRDYGYYFDFWGQGTTVTVSS (SEQ ID NO: 44) |
| VCD25-L1H2 | QIVSTQSPDTQSVTPKEKVTITCRASSSRSYMQWYQQKPDQSPKRWIYDTSKSASGVPSRFSGSGSG TDYTLTINSLEAEDAATYYCHQRSSYTFGQGTKLEIK *GGGGSGGGGSGGGGSGGGGSGGGGSGGGGS* QVQLVQSGAEVKKPGASVKVSCKASGYSFTRYWMHWVRQPPGQRLEWMGAIYPGNSDTSYSQKF EGRVTITADTSASTAYMELSSLRSEDTAVYYCSRDYGYYFDFWGQGTTVTVSS (SEQ ID NO: 45) |
| VCD25-L1H2-DS | QIVSTQSPDTQSVTPKEKVTITCRASSSRSYMQWYQQKPDQSPKRWIYDTSKSASGVPSRFSGSGSG TDYTLTINSLEAEDAATYYCHQRSSYTFGCGTKLEIK *GGGGSGGGGSGGGGSGGGGSGGGGSGGGGS* QVQLVQSGAEVKKPGASVKVSCKASGYSFTRYWMHWVRQPPGQRLEWMGAIYPGNSDTSYSQKF EGRVTITADTSASTAYMELSSLRSEDTAVYYCSRDYGYYFDFWGQCTTVTVSS (SEQ ID NO: 46) |
| VCD25-L2H1 | EIVLTQSPDFQSVTPKEKVTITCRASSSRSYMQWYQQKPDQSPKRLIYDTSKSASGVPSRFSGSGSGT DYTLTINSLEAEDAATYYCHQRSSYTFGQGTKLEIK *GGGGSGGGGSGGGGSGGGGSGGGGSGGGGS* QVQLVQSGAGVAKPGASVKVSCKASGYSFTRYWMHWVRQPPGQGLEWMGAIYPGNSDTSYSQK FEGRVTITADTSASTAYMELSSLRSEDTAVYYCSRDYGYYFDFWGQGTTVTVSS (SEQ ID NO: 47) |
| VCD25-L2H1-DS | EIVLTQSPDFQSVTPKEKVTITCRASSSRSYMQWYQQKPDQSPKRLIYDTSKSASGVPSRFSGSGSGT DYTLTINSLEAEDAATYYCHQRSSYTFGCGTKLEIK *GGGGSGGGGSGGGGSGGGGSGGGGSGGGGS* QVQLVQSGAGVAKPGASVKVSCKASGYSFTRYWMHWVRQPPGQGLEWMGAIYPGNSDTSYSQK FEGRVTITADTSASTAYMELSSLRSEDTAVYYCSRDYGYYFDFWGQCTTVTVSS (SEQ ID NO: 48) |
| VCD25-L2H2 | EIVLTQSPDFQSVTPKEKVTITCRASSSRSYMQWYQQKPDQSPKRLIYDTSKSASGVPSRFSGSGSGT DYTLTINSLEAEDAATYYCHQRSSYTFGQGTKLEIK *GGGGSGGGGSGGGGSGGGGSGGGGSGGGGS* |

TABLE 6-continued

Anti-CD25 scFv sequences

| Construct | Sequence |
|---|---|
| | QVQLVQSGAEVKKPGASVKVSCKASGYSFTRYWMHWVRQPPGQRLEWMGAIYPGNSDTSYSQKF<br>EGRVTITADTSASTAYMELSSLRSEDTAVYYCSRDYGYYFDFWGQGTTVTVSS (SEQ ID NO: 49) |
| VCD25-<br>L2H2-DS | EIVLTQSPDFQSVTPKEKVTITCRASSSRSYMQWYQQKPDQSPKRLIYDTSKSASGVPSRFSGSGSGT<br>DYTLTINSLEAEDAATYYCHQRSSYTFGCGTKLEIK<br>*GGGGSGGGGSGGGGSGGGGSGGGGSGGGGS*<br>QVQLVQSGAEVKKPGASVKVSCKASGYSFTRYWMHWVRQPPGQRLEWMGAIYPGNSDTSYSQKF<br>EGRVTITADTSASTAYMELSSLRSEDTAVYYCSRDYGYYFDFWGQCTTVTVSS (SEQ ID NO: 50) |

Example 3: Design of Antibody Heterodimer Platforms

Human IgG2 and IgG4 antibodies have the lowest ADCC and CDC among human IgG antibodies, and were chosen for optimization for creating novel heterodimeric constructs, which are outlined in Table 7.

Heterodimerization of the IgG2 and IgG4 constructs are based on including K409R (on one half-antibody) and F405L (on second antibody) mutations in the CH3 domains (numbering according to the EU Index, referred to as "EU numbering". Reference https://www.nature.com/articles/nprot.2014.169). Each half antibody is first generated as a single homodimer, then mixed together and allowed to recombine as heterodimers under reducing and oxidizing conditions.

To further reduce any potential ADCC/ADCP/CDC effector functions, LALA mutations L234A/L235A (EU numbering) were incorporated (from 1992 paper: https://pubmed.ncbi.nlm.nih.gov/1530984/), as well as K322A (Ref https://pubmed.ncbi.nlm.nih.gov/11711607/).

For the IgG4 constructs, S228P mutations (EU numbering) were incorporated in IgG4 designs to prevent Fab arm exchange.

For the IgG2 constructs, the WT IGG2 hinge was replaced with an IGG1 hinge (DKTHTCPPCPAP) or an IGG4 hinge with S228P mutation (YGPPCPPCPAP) to maintain 2 disulfide bonds at the hinge rather than 4. It is speculated that this might decrease the possibility of proteolytic cleavage and enhance heterodimerization formation with inserted K409R/F405L mutations.

For IgG4 heterodimers, V-IGG4-A pairs with V-IGG4-B. For IgG2 heterodimers, V-IGG2-A pairs with V-IGG2-B, and V-IGG2-D pairs with V-IGG2-E.

TABLE 7

Sequences for Fc heterodimerization

| Construct | Sequence | Notes |
|---|---|---|
| WT huIgG1<br>CH1-CH2-CH3 | ASTKGPSVFPLAPSSKSTSGGTAALGCLVKDYFPEPVTVSWNSG<br>ALTSGVHTFPAVLQSSGLYSLSSVVTVPSSSLGTQTYICNVNHKP<br>SNTKVDKKVEPKSCDKTHTCPPCPAPELLGGPSVFLFPPKPKDTL<br>MISRTPEVTCVVVDVSHEDPEVKFNWYVDGVEVHNAKTKPRE<br>EQYNSTYRVVSVLTVLHQDWLNGKEYKCKVSNKALPAPIEKTIS<br>KAKGQPREPQVYTLPPSRDELTKNQVSLTCLVKGFYPSDIAVEW<br>ESNGQPENNYKTTPPVLDSDGSFFLYSKLTVDKSRWQQGNVFS<br>CSVMHEALHNHYTQKSLSLSPGK (SEQ ID NO: 51) | |
| WT huIgG4<br>CH1-CH2-CH3 | ASTKGPSVFPLAPCSRSTSESTAALGCLVKDYFPEPVTVSWNSG<br>ALTSGVHTFPAVLQSSGLYSLSSVVTVPSSSLGTKTYTCNVDHKP<br>SNTKVDKRVESKYGPPCPSCPAPEFLGGPSVFLFPPKPKDTLMIS<br>RTPEVTCVVVDVSQEDPEVQFNWYVDGVEVHNAKTKPREEQF<br>NSTYRVVSVLTVLHQDWLNGKEYKCKVSNKGLPSSIEKTISKAK<br>GQPREPQVYTLPPSQEEMTKNQVSLTCLVKGFYPSDIAVEWES<br>NGQPENNYKTTPPVLDSDGSFFLYSRLTVDKSRWQEGNVFSCS<br>VMHEALHNHYTQKSLSLSLGK (SEQ ID NO: 52) | |
| V-IGG4-A | ASTKGPSVFPLAPCSRSTSESTAALGCLVKDYFPEPVTVSWNSG<br>ALTSGVHTFPAVLQSSGLYSLSSVVTVPSSSLGTKTYTCNVDHKP<br>SNTKVDKRVESKYGPPCPPCPAPEAAGGPSVFLFPPKPKDTLMI<br>SRTPEVTCVVVDVSQEDPEVQFNWYVDGVEVHNAKTKPREEQ<br>FNSTYRVVSVLTVLHQDWLNGKEYKCAVSNKGLPSSIEKTISKAK<br>GQPREPQVYTLPPSQEEMTKNQVSLTCLVKGFYPSDIAVEWES<br>NGQPENNYKTTPPVLDSDGSFFLYSRLTVDKSRWQEGNVFSCS<br>VMHEALHNHYTQKSLSLSLGK (SEQ ID NO: 53) | S228P<br>FALA (F234A, L235A)<br>K322A<br>Naturally contains<br>F405 and R409 |
| V-IGG4-A-Fc | GGGGSGGGGSGGGGSKYGPPCPPCPAPEAAGGPSVFLFPPKP<br>KDTLMISRTPEVTCVVVDVSQEDPEVQFNWYVDGVEVHNAKT<br>KPREEQFNSTYRVVSVLTVLHQDWLNGKEYKCAVSNKGLPSSIE<br>KTISKAKGQPREPQVYTLPPSQEEMTKNQVSLTCLVKGFYPSDI<br>AVEWESNGQPENNYKTTPPVLDSDGSFFLYSRLTVDKSRWQE<br>GNVFSCSVMHEALHNHYTQKSLSLSLGK (SEQ ID NO: 54) | Same as SEQ ID<br>NO: 53, but with<br>linker and fc<br>only |

TABLE 7-continued

Sequences for Fc heterodimerization

| Construct | Sequence | Notes |
|---|---|---|
| V-IGG4-B | ASTKGPSVFPLAPCSRSTSESTAALGCLVKDYFPEPVTVSWNSG<br>ALTSGVHTFPAVLQSSGLYSLSSVVTVPSSSLGTKTYTCNVDHKP<br>SNTKVDKRVESKYGPPCPPCPAPEAAGGPSVFLFPPKPKDTLMI<br>SRTPEVTCVVVDVSQEDPEVQFNWYVDGVEVHNAKTKPREEQ<br>FNSTYRVVSVLTVLHQDWLNGKEYKCAVSNKGLPSSIEKTISKAK<br>GQPREPQVYTLPPSQEEMTKNQVSLTCLVKGFYPSDIAVEWES<br>NGQPENNYKTTPPVLDSDGSFLLYSKLTVDKSRWQEGNVFSCS<br>VMHEALHNHYTQKSLSLSLGK (SEQ ID NO: 55) | S228P<br>FALA (F234A, L235A)<br>K322A<br>F405L, R409K |
| V-IGG4-B-Fc | GGGGSGGGGSGGGGSKYGPPCPPCPAPEAAGGPSVFLFPPKP<br>KDTLMISRTPEVTCVVVDVSQEDPEVQFNWYVDGVEVHNAKT<br>KPREEQFNSTYRVVSVLTVLHQDWLNGKEYKCAVSNKGLPSSIE<br>KTISKAKGQPREPQVYTLPPSQEEMTKNQVSLTCLVKGFYPSDI<br>AVEWESNGQPENNYKTTPPVLDSDGSFLLYSKLTVDKSRWQE<br>GNVFSCSVMHEALHNHYTQKSLSLSLGK (SEQ ID NO: 56) | Same as SEQ ID<br>NO: 55, but with<br>linker and fc only |
| WT huIgG2<br>CH1-CH2-CH3 | ASTKGPSVFPLAPCSRSTSESTAALGCLVKDYFPEPVTVSWNSG<br>ALTSGVHTFPAVLQSSGLYSLSSVVTVPSSNFGTQTYTCNVDHK<br>PSNTKVDKTVERKCCVECPPCPAPPVAGPSVFLFPPKPKDTLMI<br>SRTPEVTCVVVDVSHEDPEVQFNWYVDGVEVHNAKTKPREEQ<br>FNSTFRVVSVLTVVHQDWLNGKEYKCKVSNKGLPAPIEKTISKT<br>KGQPREPQVYTLPPSREEMTKNQVSLTCLVKGFYPSDISVEWES<br>NGQPENNYKTTPPMLDSDGSFFLYSKLTVDKSRWQQGNVFSC<br>SVMHEALHNHYTQKSLSLSPGK (SEQ ID NO: 57) | |
| V-IGG2 | ASTKGPSVFPLAPCSRSTSESTAALGCLVKDYFPEPVTVSWNSG<br>ALTSGVHTFPAVLQSSGLYSLSSVVTVPSSNFGTQTYTCNVDHK<br>PSNTKVDKTVERKDKTHTCPPCPAPPAAGPSVFLFPPKPKDTLM<br>ISRTPEVTCVVVDVSHEDPEVQFNWYVDGVEVHNAKTKPREE<br>QFNSTFRVVSVLTVVHQDWLNGKEYKCAVSNKGLPAPIEKTISK<br>TKGQPREPQVYTLPPSREEMTKNQVSLTCLVKGFYPSDISVEWE<br>SNGQPENNYKTTPPMLDSDGSFFLYSKLTVDKSRWQQGNVFS<br>CSVMHEALHNHYTQKSLSLSPGK (SEQ ID NO: 58) | Contains IgG1 hinge<br>(DKTHTCPPCPAP)<br>VA (V234A)<br>K322A |
| V-IGG2-Fc | GGGGSGGGGSGGGGSDKTHTCPPCPAPPAAGPSVFLFPPKPK<br>DTLMISRTPEVTCVVVDVSHEDPEVQFNWYVDGVEVHNAKTK<br>PREEQFNSTFRVVSVLTVVHQDWLNGKEYKCAVSNKGLPAPIE<br>KTISKTKGQPREPQVYTLPPSREEMTKNQVSLTCLVKGFYPSDIS<br>VEWESNGQPENNYKTTPPMLDSDGSFFLYSKLTVDKSRWQQG<br>NVFSCSVMHEALHNHYTQKSLSLSPGK (SEQ ID NO: 59) | Same as SEQ ID<br>NO: 58, but with<br>linker and fc only |
| V-IGG2-A | ASTKGPSVFPLAPCSRSTSESTAALGCLVKDYFPEPVTVSWNSG<br>ALTSGVHTFPAVLQSSGLYSLSSVVTVPSSNFGTQTYTCNVDHK<br>PSNTKVDKTVERKDKTHTCPPCPAPPAAGPSVFLFPPKPKDTLM<br>ISRTPEVTCVVVDVSHEDPEVQFNWYVDGVEVHNAKTKPREE<br>QFNSTFRVVSVLTVVHQDWLNGKEYKCAVSNKGLPAPIEKTISK<br>TKGQPREPQVYTLPPSREEMTKNQVSLTCLVKGFYPSDISVEWE<br>SNGQPENNYKTTPPMLDSDGSFFLYSRLTVDKSRWQQGNVFS<br>CSVMHEALHNHYTQKSLSLSPGK (SEQ ID NO: 60) | Contains IgG1 hinge<br>(DKTHTCPPCPAP)<br>VA (V234A)<br>K322A<br>K409R |
| V-IGG2-A-Fc | GGGGSGGGGSGGGGSDKTHTCPPCPAPPAAGPSVFLFPPKPK<br>DTLMISRTPEVTCVVVDVSHEDPEVQFNWYVDGVEVHNAKTK<br>PREEQFNSTFRVVSVLTVVHQDWLNGKEYKCAVSNKGLPAPIE<br>KTISKTKGQPREPQVYTLPPSREEMTKNQVSLTCLVKGFYPSDIS<br>VEWESNGQPENNYKTTPPMLDSDGSFFLYSRLTVDKSRWQQG<br>NVFSCSVMHEALHNHYTQKSLSLSPGK (SEQ ID NO: 61) | Same as SEQ ID<br>NO: 60, but with<br>linker and fc only |
| V-IGG2-B | ASTKGPSVFPLAPCSRSTSESTAALGCLVKDYFPEPVTVSWNSG<br>ALTSGVHTFPAVLQSSGLYSLSSVVTVPSSNFGTQTYTCNVDHK<br>PSNTKVDKTVERKDKTHTCPPCPAPPAAGPSVFLFPPKPKDTLM<br>ISRTPEVTCVVVDVSHEDPEVQFNWYVDGVEVHNAKTKPREE<br>QFNSTFRVVSVLTVVHQDWLNGKEYKCAVSNKGLPAPIEKTISK<br>TKGQPREPQVYTLPPSREEMTKNQVSLTCLVKGFYPSDISVEWE<br>SNGQPENNYKTTPPMLDSDGSFFLYSKLTVDKSRWQQGNVFS<br>CSVMHEALHNHYTQKSLSLSPGK (SEQ ID NO: 62) | Contains IgG1 hinge<br>(DKTHTCPPCPAP)<br>LALA (V234A)<br>K322A<br>F405L |
| V-IGG2-B-Fc | GGGGSGGGGSGGGGSDKTHTCPPCPAPPAAGPSVFLFPPKPK<br>DTLMISRTPEVTCVVVDVSHEDPEVQFNWYVDGVEVHNAKTK<br>PREEQFNSTFRVVSVLTVVHQDWLNGKEYKCAVSNKGLPAPIE<br>KTISKTKGQPREPQVYTLPPSREEMTKNQVSLTCLVKGFYPSDIS<br>VEWESNGQPENNYKTTPPMLDSDGSFLLYSKLTVDKSRWQQG<br>NVFSCSVMHEALHNHYTQKSLSLSPGK (SEQ ID NO: 63) | Same SEQ ID NO: 62,<br>but with linker and<br>fc only |
| V-IGG2-C | ASTKGPSVFPLAPCSRSTSESTAALGCLVKDYFPEPVTVSWNSG<br>ALTSGVHTFPAVLQSSGLYSLSSVVTVPSSNFGTQTYTCNVDHK | Contains IgG4 hinge<br>(YGPPCPPCPAP) with |

TABLE 7-continued

Sequences for Fc heterodimerization

| Construct | Sequence | Notes |
|---|---|---|
|  | PSNTKVDKTVERKYGPPCPPCPAPPAAGPSVFLFPPKPKDTLMI SRTPEVTCVVVDVSHEDPEVQFNWYVDGVEVHNAKTKPREEQ FNSTFRVVSVLTVVHQDWLNGKEYKCAVSNKGLPAPIEKTISKT KGQPREPQVYTLPPSREEMTKNQVSLTCLVKGFYPSDISVEWES NGQPENNYKTTPPMLDSDGSFFLYSKLTVDKSRWQQGNVFSC SVMHEALHNHYTQKSLSLSPGK (SEQ ID NO: 64) | S228P LALA (V234A) K322A |
| V-IGG2-C-Fc | GGGGSGGGGSGGGGSYGPPCPPCPAPPAAGPSVFLFPPKPKD TLMISRTPEVTCVVVDVSHEDPEVQFNWYVDGVEVHNAKTKP REEQFNSTFRVVSVLTVVHQDWLNGKEYKCAVSNKGLPAPIEK TISKTKGQPREPQVYTLPPSREEMTKNQVSLTCLVKGFYPSDISV EWESNGQPENNYKTTPPMLDSDGSFFLYSKLTVDKSRWQQG NVFSCSVMHEALHNHYTQKSLSLSPGK (SEQ ID NO: 65) | Same as SEQ ID NO: 64, but with linker and fc only |
| V-IGG2-D | ASTKGPSVFPLAPCSRSTSESTAALGCLVKDYFPEPVTVSWNSG ALTSGVHTFPAVLQSSGLYSLSSVVTVPSSNFGTQTYTCNVDHK PSNTKVDKTVERKYGPPCPPCPAPPAAGPSVFLFPPKPKDTLMI SRTPEVTCVVVDVSHEDPEVQFNWYVDGVEVHNAKTKPREEQ FNSTFRVVSVLTVVHQDWLNGKEYKCAVSNKGLPAPIEKTISKT KGQPREPQVYTLPPSREEMTKNQVSLTCLVKGFYPSDISVEWES NGQPENNYKTTPPMLDSDGSFFLYSRLTVDKSRWQQGNVFSC SVMHEALHNHYTQKSLSLSPGK (SEQ ID NO: 66) | Contains IgG4 hinge (YGPPCPPCPAP) with 5228P LALA (V234A) K322A K409R |
| V-IGG2-D-Fc | GGGGSGGGGSGGGGSYGPPCPPCPAPPAAGPSVFLFPPKPKD TLMISRTPEVTCVVVDVSHEDPEVQFNWYVDGVEVHNAKTKP REEQFNSTFRVVSVLTVVHQDWLNGKEYKCAVSNKGLPAPIEK TISKTKGQPREPQVYTLPPSREEMTKNQVSLTCLVKGFYPSDISV EWESNGQPENNYKTTPPMLDSDGSFFLYSRLTVDKSRWQQG NVFSCSVMHEALHNHYTQKSLSLSPGK (SEQ ID NO: 67) | Same as SEQ ID NO: 66, but with linker and fc only |
| V-IGG2-E | ASTKGPSVFPLAPCSRSTSESTAALGCLVKDYFPEPVTVSWNSG ALTSGVHTFPAVLQSSGLYSLSSVVTVPSSNFGTQTYTCNVDHK PSNTKVDKTVERKYGPPCPPCPAPPAAGPSVFLFPPKPKDTLMI SRTPEVTCVVVDVSHEDPEVQFNWYVDGVEVHNAKTKPREEQ FNSTFRVVSVLTVVHQDWLNGKEYKCAVSNKGLPAPIEKTISKT KGQPREPQVYTLPPSREEMTKNQVSLTCLVKGFYPSDISVEWES NGQPENNYKTTPPMLDSDGSFLLYSKLTVDKSRWQQGNVFSC SVMHEALHNHYTQKSLSLSPGK (SEQ ID NO: 68) | Contains IgG4 hinge (YGPPCPPCPAP) with 5228P LALA (V234A) K322A F405L |
| V-IGG2-E-Fc | GGGGSGGGGSGGGGSYGPPCPPCPAPPAAGPSVFLFPPKPKD TLMISRTPEVTCVVVDVSHEDPEVQFNWYVDGVEVHNAKTKP REEQFNSTFRVVSVLTVVHQDWLNGKEYKCAVSNKGLPAPIEK TISKTKGQPREPQVYTLPPSREEMTKNQVSLTCLVKGFYPSDISV EWESNGQPENNYKTTPPMLDSDGSFLLYSKLTVDKSRWQQGN VFSCSVMHEALHNHYTQKSLSLSPGK (SEQ ID NO: 69) | Same as SEQ ID NO: 68, but with linker and fc only |

Example 4: Design of Monospecific and 1+1 Bispecific Antibodies

Monospecific anti-CD3, anti-CD25 and 1+1 bispecific anti-CD3×anti-CD25 antibodies were constructed based on sequences from Examples 1-3 and are presented in FIG. 1 and Table 8.

TABLE 8

Sequences of monospecific anti-CD3, anti-CD25 and 1 + 1 bispecific anti-CD3 × anti-CD25 antibodies For the constructs in TABLE 8, the Kappa CL domain (KCL) is defined as:
(SEQ ID NO: 70)
RTVAAPSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC

| Construct | Sequence of Chain 1 | Sequence of Chain 2 | Sequence of Chain 3 | Sequence of Chain 4 |
|---|---|---|---|---|
| VIT-100 | (VCD3-L1 or VCD3-L2 or VCD3-L3)- KCL | Same as Chain 1 | (VCD3-H1 or VCD3-H2 or VCD3-H3)- (V-IGG4-A or V-IGG2 or V-IGG2-C) | Same as Chain 3 |

TABLE 8-continued

Sequences of monospecific anti-CD3, anti-CD25 and 1 + 1 bispecific anti-CD3 × anti-CD25 antibodies

| | Chain 1 | Chain 2 | Chain 3 | Chain 4 |
|---|---|---|---|---|
| VIT-101 | (VCD25-L1 or VCD25-L2)- KCL | Same as Chain 1 | (VCD25-H1 or VCD25-H2)- (V-IGG4-A or V-IGG2 or V-IGG2-C) | Same as Chain 3 |
| VIT-102 | (VCD3-L1 or VCD3-L2 or VCD3-L3)- KCL | (VCD25-L1 or VCD25-L2)-KCL | (VCD3-H1 or VCD3-H2 or VCD3-H3)- (V-IGG4-A or V-IGG2-A or V-IGG2-D) | (VCD25-H1 or VCD25-H2)- (V-IGG4-B or V-IGG2-B or V-IGG2-E) |
| VIT-103 | (any sequence from TABLE 3)- (V-IGG4-A-Fc or V-IGG2-Fc or V-IGG2-C-Fc) | Same as Chain 1 | | |
| VIT-104 | (any sequence from TABLE 6)- (V-IGG4-A-Fc or V-IGG2-Fc or V-IGG2-C-Fc) | Same as Chain 1 | | |
| VIT-105 | (any sequence from TABLE 3)- (V-IGG4-A-Fc or V-IGG2-A-Fc or V-IGG2-D-Fc) | (any sequence from TABLE 6)- (V-IGG4-B-Fc or V-IGG2-B-Fc or V-IGG2-E-Fc) | | |

Example 5: Design of 2+2 Bispecific Antibodies

2+2 bispecific anti-CD3×anti-CD25 antibodies were constructed based on sequences from Examples 1-3 and are presented in FIG. 2 and Table 9.

For the constructs VIT-106, VIT-107 and VIT-108, the specificity on one antigen is encoded in a Fab domain, and the specificity of the second antigen is encoded by a scFv fused to the end of the light chain. It is speculated that IgG2 and IgG4 domains are ideal to make LC-scFv fusions (both as homodimers and heterodimers) because of the position of the CL-CH1 interdomain disulfide bond, which is in a different location than IgG1.

TABLE 9

Sequences of 2 + 2 bispecific anti-CD3 × anti-CD25 antibodies

| Construct | Sequence of Chain 1 | Sequence of Chain 2 | Sequence of Chain 3 | Sequence of Chain 4 |
|---|---|---|---|---|
| VIT-106 | (VCD3-L1 or VCD3-L2 L3)-KCL-GGGGSGGGGSGG GGS-(any sequence from TABLE 6) | Same as Chain1 or VCD3- | (VCD3-H1 or VCD3-H2 or VCD3-H3)- (V-IGG4-A or V-IGG2 or V-IGG2-C) | Same as Chain 3 |
| VIT-107 | (VCD25-L1 or VCD25-L2)-KCL-GGGGSGGGGSGG GGS-(any sequence from TABLE 3) | Same as Chain1 | (VCD25-H1 or VCD25-H2)- (V-IGG4-A or V-IGG2 or V-IGG2-C) | Same as Chain 3 |
| VIT-108 | (VCD3-L1 or VCD3-L2 or VCD3-L3)-KCL-GGGGSGGGGSGG | (VCD25-L1 or VCD25-L2)-KCL-GGGGSGGGGSGG GGS-(any | (VCD3-H1 or VCD3-H2 or VCD3-H3)- (V-IGG4-A or V- | (VCD25-H1 or VCD25-H2)- (V-IGG4-B or V-IGG2-B or V-IGG2- |

TABLE 9-continued

Sequences of 2 + 2 bispecific anti-CD3 x anti-CD25 antibodies

| Construct | Sequence of Chain 1 | Sequence of Chain 2 | Sequence of Chain 3 | Sequence of Chain 4 |
|---|---|---|---|---|
| | GGS-any sequence from TABLE 6) | sequence from TABLE 3) | IGG2-A or V-IGG2-D) | E) |
| VIT-109 | (any sequence from TABLE 3)-(V-IGG4-A-Fc or V-IGG2-Fc or V-IGG2-C-Fc)-GGGGSGGGGSGGGGS-(any sequence from TABLE 6) | Same as Chain 1 | | |
| VIT-110 | (any sequence from TABLE 6)-(V-IGG4-A-Fc or V-IGG2-Fc or V-IGG2-C-Fc)-GGGGSGGGGSGGGGS-(any sequence from TABLE 3) | Same as Chain 1 | | |
| VIT-111 | (any sequence from TABLE 3)-(V-IGG4-A-Fc or V-IGG2-A-Fc or V-IGG2-D-Fc)-GGGGSGGGGSGGGGS-(any sequence from TABLE 6) | (any sequence from TABLE 6)-(V-IGG4-B-Fc or V-IGG2-B-Fc or V-IGG2-E-Fc)-GGGGSGGGGSGGGGS-(any sequence from TABLE 3) | | |

Items

The invention is further described by the following items.

1. An antibody or fragment thereof, capable of binding to CD3 and/or CD25.
2. The antibody or fragment thereof according to any of the precedent items, capable of binding to CD3.
3. The antibody or fragment thereof according to any of the precedent items, wherein said antibody or fragment thereof comprises at least one of the amino acid sequences of CDR1, CDR2 and CDR3 of the murine antibody OKT3 variable light chain and/or at least one of the amino acid sequences of CDR1, CDR2 and CDR3 of the murine antibody OKT3 variable heavy chain.
4. The antibody or fragment thereof according to any of the preceding items, wherein said antibody or fragment thereof comprises the amino acid sequences of CDR1, CDR2 and CDR3 of the murine antibody OKT3 variable light chain and/or the amino acid sequences of CDR1, CDR2 and CDR3 of the murine antibody OKT3 variable heavy chain.
5. The antibody or fragment thereof according to any of the preceding items, wherein said antibody or fragment thereof comprises variable light chain CDR sequences of SEQ ID NO:73-75.
6. The antibody or fragment thereof according to any of the preceding items, wherein said antibody or fragment thereof comprises variable heavy chain CDR sequences of SEQ ID NO:76-78.
7. The antibody or fragment thereof according to any of the preceding items, wherein said antibody or fragment thereof comprises variable light chain CDR sequences of SEQ ID NO:73-75 and variable heavy chain CDR sequences of SEQ ID NO:76-78.
8. The antibody or fragment thereof according to any of the preceding items, wherein all antigen contact residues of murine antibody OKT3 are contained.
9. The antibody or fragment thereof according to any of the preceding items, wherein all CDR sequences of murine antibody OKT3 are contained.
10. The antibody or fragment thereof according to any of the preceding items, wherein all antigen contact residues and all CDR sequences of murine antibody OKT3 are contained.
11. The antibody or fragment thereof according to any of the preceding items comprising the murine antibody OKT3 variable heavy chain residue K82 (IMGT numbering).
12. The antibody or fragment thereof according to any of the preceding items, wherein said antibody or fragment thereof comprises a variable heavy chain domain of SEQ ID NO:6-10 and a variable light chain domain of SEQ ID NO:1-5.
13. The antibody or fragment thereof according to any of the preceding items, wherein said antibody or fragment thereof comprises a Cys114Ser mutation (IMGT numbering) in the heavy chain CDR3 region.
14. The antibody or fragment thereof according to any of the preceding items, capable of binding to CD25.

15. The antibody or fragment thereof according to any of the preceding items, wherein said antibody or fragment thereof comprises at least one of the amino acid sequences of CDR1, CDR2 and CDR3 of the monoclonal antibody Basiliximab variable light chain and/or at least one of the amino acid sequences of CDR1, CDR2 and CDR3 of the monoclonal antibody Basiliximab variable heavy chain.
16. The antibody or fragment thereof according to any of the preceding items, wherein said antibody or fragment thereof comprises the amino acid sequences of CDR1, CDR2 and CDR3 of the monoclonal antibody Basiliximab variable light chain and/or the amino acid sequences of CDR1, CDR2 and CDR3 of the monoclonal antibody Basiliximab variable heavy chain.
17. The antibody or fragment thereof according to any of the preceding items, wherein said antibody or fragment thereof comprises variable light chain CDR sequences of SEQ ID NO:79-81.
18. The antibody or fragment thereof according to any of the preceding items, wherein said antibody or fragment thereof comprises variable heavy chain CDR sequences of SEQ ID NO:82-84.
19. The antibody or fragment thereof according to any of the preceding items, wherein said antibody or fragment thereof comprises variable light chain CDR sequences of SEQ ID NO:79-81 and variable heavy chain CDR sequences of SEQ ID NO:82-84.
20. The antibody or fragment thereof according to any of the preceding items, wherein all antigen contact residues of monoclonal antibody Basiliximab are contained.
21. The antibody or fragment thereof according to any of the preceding items, wherein all CDR sequences of monoclonal antibody Basiliximab are contained.
22. The antibody or fragment thereof according to any of the preceding items, wherein all antigen contact residues and all CDR sequences of monoclonal antibody Basiliximab are contained.
23. The antibody or fragment thereof according to any of the preceding items, wherein said antibody or fragment thereof comprises a variable heavy chain domain of SEQ ID NO:29-31 and a variable light chain domain of SEQ ID NO:32-34.
24. The antibody or fragment thereof according to any of the preceding items, wherein said antibody or fragment thereof is humanized.
25. The antibody or fragment thereof according to any of the preceding items, wherein said antibody or fragment thereof comprises a scFv.
26. The antibody or fragment thereof according to any of the preceding items, wherein said antibody or fragment thereof is a scFv.
27. The antibody or fragment thereof according to any of the preceding items, wherein said scFv has increased disulfide stabilization.
28. The antibody or fragment thereof according to any of the preceding items, wherein said scFv comprises at least one Cys substitution at a position selected from VH44-VL100 according to Kabat numbering.
29. The antibody or fragment thereof according to any of the preceding items, wherein said antibody or fragment thereof comprises a linker.
30. The antibody or fragment thereof according to any of the preceding items, wherein said scFv comprises a linker.
31. The antibody or fragment thereof according to any of the preceding items, wherein said linker is a peptide linker.
32. The antibody or fragment thereof according to any of the preceding items, wherein said linker comprises the sequence of SEQ ID NO:71.
33. The antibody or fragment thereof according to any of the preceding items, wherein said scFv binds CD3 and comprises a sequence selected from the group consisting of SEQ ID NO:11-28.
34. The antibody or fragment thereof according to any of the preceding items, wherein said scFv binds CD25 and comprises a sequence selected from the group consisting of SEQ ID NO:35-50.
35. The antibody or fragment thereof according to any of the preceding items, wherein said antibody or fragment thereof comprises a constant light chain (CL) domain selected from the group consisting of kappa CL domain and lambda CL domain.
36. The antibody or fragment thereof according to any of the preceding items, wherein said antibody or fragment thereof comprises a sequence selected from the group consisting of a kappa CL domain sequence and a lambda CL domain sequence.
37. The antibody or fragment thereof according to any of the preceding items, wherein said antibody or fragment thereof comprises a sequence of SEQ ID NO:70.
38. The antibody or fragment thereof according to any of the preceding items, wherein said antibody or fragment thereof is a heterodimeric construct.
39. The antibody or fragment thereof according to any of the preceding items, wherein said heterodimeric construct comprises IgG2 and/or IgG4 constant domain.
40. The antibody or fragment thereof according to any of the preceding items, wherein said heterodimeric construct comprises a point mutation selected from the group consisting of K409R, R409K, F405L, L234A, F234A, V234A, L235A, K322A and S228P.
41. The antibody or fragment thereof according to any of the preceding items, wherein said antibody or fragment thereof comprises a sequence selected from the group consisting of SEQ ID NO:51-69.
42. The antibody or fragment thereof according to any of the preceding items, wherein said antibody or fragment thereof is a monospecific antibody.
43. The antibody or fragment thereof according to any of the preceding items, wherein said antibody or fragment thereof is a bispecific antibody.
44. The antibody or fragment thereof according to any of the preceding items, wherein said antibody or fragment thereof is a multispecific antibody.
45. The antibody or fragment thereof according to any of the preceding items, wherein said antibody or fragment thereof is a 4 chain IgG antibody.
46. The antibody or fragment thereof according to any of the preceding items, wherein said antibody or fragment thereof is a 2 chain scFv-Fc antibody.
47. The antibody or fragment thereof according to any of the preceding items, wherein said antibody or fragment thereof is a 2 chain scFv-Fc-scFv antibody.
48. The antibody or fragment thereof according to any of the preceding items, wherein said antibody or fragment thereof is 2 chain scFv-IgG4-Fc antibody.
49. The antibody or fragment thereof according to any of the preceding items, wherein said antibody or fragment thereof comprises a first antigen binding site capable of binding to CD3 and a second antigen binding site capable of binding to CD25, wherein said first antigen binding site is comprised in a Fab fragment and said second antigen binding site is comprised in a moiety selected from the group consisting of scFv, antibody fragments and protein moiety, wherein said moiety being attached to the light chain of said Fab fragment.
50. The antibody or fragment thereof according to any of the preceding items, wherein said moiety is a scFv.
51. The antibody or fragment thereof according to any of the preceding items, wherein said moiety is attached to the C-terminus or N-terminus of the light chain of said Fab fragment.
52. The antibody or fragment thereof according to any of the preceding items, wherein said moiety is attached to the C-terminus of the light chain of said Fab fragment.
53. The antibody or fragment thereof according to any of the preceding items, wherein said Fab fragment is derived from an IgG or an IgM.
54. The antibody or fragment thereof according to any of the preceding items, wherein said Fab fragment is derived from an IgG.
55. The antibody or fragment thereof according to any of the preceding items, wherein said Fab fragment is derived from an IgG selected from the group consisting of Ig IgG2, IgG3 and IgG4.
56. The antibody or fragment thereof according to any of the preceding items, wherein said Fab fragment is derived from an IgG2 or an IgG4.
57. The antibody or fragment thereof according to any of the preceding items, wherein said antibody or fragment thereof is isolated.
58. The antibody or fragment thereof according to any of the preceding items, wherein said antibody or fragment thereof has increased stability and/or increased manufacturability.
59. A pharmaceutical composition comprising an antibody or fragment thereof according to any of the preceding items and an excipient, such as a pharmaceutically-acceptable carrier.
60. The pharmaceutical composition according to any of the preceding items comprising an adjuvant.
61. The pharmaceutical composition according to any of the preceding items, wherein said adjuvant is selected from the group consisting of β-D-galactosylceramide, α-D-galactosylceramide and β-glucan.
62. The pharmaceutical composition according to any of the preceding items, wherein said pharmaceutical composition is a stabilized pharmaceutical.
63. The antibody or fragment thereof and/or pharmaceutical composition according to any of the preceding items, wherein said antibody or antigen binding fragment and/or pharmaceutical composition allows administration through a route selected among subcutaneous administration, intradermal administration, intramuscular administration, oral administration and/or nasal administration.
64. The antibody or fragment thereof and/or pharmaceutical composition according to any of the preceding items, wherein said antibody or antigen binding fragment and/or pharmaceutical composition allows administration through a route selected among oral and nasal administration.
65. A method of preventing, treating and/or alleviating an inflammatory disease, a psycho-immune disorder, an auto-immune disease and/or a mood disorder comprising administering to a patient in need thereof a therapeutically effective amount of the antibody or fragment thereof and/or pharmaceutical composition according to any of the preceding items.
66. A method of preventing, treating and/or alleviating an inflammatory disease comprising administering to a patient in need thereof a therapeutically effective amount of the antibody or fragment thereof and/or pharmaceutical composition according to any of the preceding items.
67. A method of preventing, treating and/or alleviating a mood disorder comprising administering to a patient in need thereof a therapeutically effective amount of the antibody or fragment thereof and/or pharmaceutical composition according to any of the preceding items.
68. A method of preventing, treating and/or alleviating a psycho-immune disorder comprising administering to a patient in need thereof a therapeutically effective amount of the antibody or fragment thereof and/or pharmaceutical composition according to any of the preceding items.
69. The method according to any of the precedent items, wherein said inflammatory disease, psycho-immune disorder and/or a mood disorder is selected from the group consisting of depression, major depressive disorder, autism (ASD) and attention deficit/hyperactivity disorder (ADHD), bipolar disorder, seasonal affective disorder (SAD), cyclothymic disorder, premenstrual dysphoric disorder, persistent depressive disorder, disruptive mood dysregulation disorder, depression related to medical illness, depression induced by substance use or medication.
70. The method according to any of the preceding items, wherein said subject is an adult or a pediatric subject.
71. The method according to any of the preceding items, wherein said antibody or fragment thereof and/or pharmaceutical composition is administered subcutaneously, intradermally, intramuscularly, orally and/or nasally.
72. The method according to any of the preceding items, wherein said antibody or fragment thereof and/or pharmaceutical composition is administered orally and/or nasally.
73. A diagnostic kit comprising the antibody or fragment thereof according to any of the preceding items and instructions for use.
74. The diagnostic kit according to any of the precedent items, wherein said diagnostic kit is for companion diagnostic.
75. The diagnostic kit according to any of the precedent items, wherein said diagnostic kit is for the selection of patients that may benefit from treatment with an antibody of fragment thereof according to any of the precedent items.
76. A method of diagnosing a disease in a subject, wherein said method comprises the following steps:
    a. Providing a blood and/or salivary sample from said subject.
    b. Contacting said blood and/or salivary sample with an antibody or fragment thereof according to any of the preceding items.
77. A method of screening and/or monitoring progression of a disease in a subject, wherein said method comprises the following steps:
    a. Providing a blood and/or salivary sample from said subject.
    b. Contacting said blood and/or salivary sample with an antibody or fragment thereof according to any of the preceding items.

78. The method according to any of the preceding items, wherein blood and/or salivary sample is monitored for a blood and/or salivary biomarker.
79. The method according to any of the preceding items, wherein blood and/or salivary biomarker is a TREG cell biomarker.
80. An isolated nucleic acid molecule encoding an antibody agent or fragment thereof according to any of the precedent items.
81. A recombinant vector comprising the nucleic acid molecule of item 80.
82. A host cell comprising the recombinant vector of item 81.
83. A method for the production of an antibody or fragment thereof according to any of the precedent items comprising a step of culturing the host cell according to item 82 in a culture medium under conditions allowing the expression of the antibody or fragment thereof and separating the antibody or fragment thereof from the culture medium.
84. The antibody or fragment thereof according to any of the precedent items, wherein the antibody or fragment thereof is produced by a recombinant vector comprising a nucleic acid encoding said antibody.
85. A method for generating a heterodimeric antibody, said method comprising the following steps:
    a) providing a first homodimeric antibody comprising a first Fc region, said first Fc region comprising a first CH3 region selected from the group consisting of a human IgG2 CH3 region and a human IgG4 CH3 region, but with an amino acid substitution at a position selected from the group consisting of: 405, 409, 234, 235 and 322 (EU numbering);
    b) providing a second homodimeric antibody comprising a second Fc region, said second Fc region comprising a second CH3 region selected from the group consisting of a human IgG2 CH3 region and a human IgG4 CH3 region, but with an amino acid substitution at a position selected from the group consisting of: 405, 409, 234, 235 and 322 (EU numbering),
    wherein the sequences of said first and second antibody CH3 regions are different,
    c) incubating said first antibody together with said second antibody under reducing conditions sufficient to allow the cysteines in the hinge region to undergo disulfide-bond isomerization, to obtain a heterodimeric antibody.
86. A method for generating a heterodimeric antibody, said method comprising the following steps:
    a) providing a first homodimeric antibody comprising an Fc region, said Fc region comprising a first CH3 region selected from the group consisting of a human IgG2 CH3 region and a human IgG4 CH3 region, but with an amino acid substitution at position 409 (EU numbering);
    b) providing a second homodimeric antibody comprising an Fc region, said Fc region comprising a second CH3 region selected from the group consisting of a human IgG2 CH3 region and a human IgG4 CH3 region, but with an amino acid substitution at position 405 (EU numbering),
    c) incubating said first antibody together with said second antibody under reducing conditions sufficient to allow the cysteines in the hinge region to undergo disulfide-bond isomerization,
    to obtain a heterodimeric antibody,
    wherein the heterodimeric interaction between said first and second antibodies in the resulting heterodimeric antibody is such that no Fab-arm exchange occurs at 0.5 mM GSH after 24 hours at 37° C.
87. A method for generating a heterodimeric antibody, said method comprising the following steps:
    a) providing a first homodimeric antibody comprising an Fc region, said Fc region comprising a first CH3 region selected from the group consisting of a human IgG2 CH3 region and a human IgG4 CH3 region;
    b) providing a second homodimeric antibody comprising an Fc region, said Fc region comprising a second CH3 region selected from the group consisting of a human IgG2 CH3 region and a human IgG4 CH3 region, but with an amino acid substitution at position 405 and an amino acid substitution at position 409 (EU numbering),
    c) incubating said first antibody together with said second antibody under reducing conditions sufficient to allow the cysteines in the hinge region to undergo disulfide-bond isomerization,
    to obtain a heterodimeric antibody,
    wherein the heterodimeric interaction between said first and second antibodies in the resulting heterodimeric antibody is such that no Fab-arm exchange occurs at 0.5 mM GSH after 24 hours at 37° C.
88. The method according to any of the preceding items, wherein said method is performed in vitro.
89. The method according to any of the preceding items, wherein said first and/or second CH3 region is of human IgG2.
90. The method according to any of the preceding items, wherein said first and/or second CH3 region is of human IgG4.
91. The method according to any of the preceding items, wherein said first and/or second Fc region is of human IgG2 or human IgG4.
92. The method according to any of the preceding items, wherein said first Fc region and/or said second Fc region is chimeric, humanized, or human.
93. The method according to any of the preceding items, wherein said heterodimeric antibody comprises a hinge region selected from a IgG1 hinge region or a IgG4 hinge region with a S228P mutation.
94. The method according to any of the preceding items, wherein said amino acid substitution is selected from the group consisting of: F405L, K409R, L234A, F234A, V234A, L235A, N297A and K322A (EU numbering).
95. The method according to any of the preceding items, wherein said first and second homodimeric antibodies bind different epitopes.
96. The method according to any of the preceding items, wherein the heterodimeric interaction between said first and second antibodies in the resulting heterodimeric antibody is such that no Fab-arm exchange occurs.
97. The method according to any of the preceding items, wherein the heterodimeric interaction between said first and second antibodies in the resulting heterodimeric antibody is such that no Fab-arm exchange occurs at 0.5 mM GSH after 24 hours at 37° C.
98. The method according to any of the preceding items, wherein the heterodimeric interaction between said first and second antibodies in the resulting heterodimeric antibody is such that no Fab-arm exchange occurs and wherein said first and/or second Fc region is of human IgG4 but with an amino acid substitution at a position 228 (EU numbering).

99. The method according to item 98, wherein said amino acid substitution is S228P.

100. The method according to any of the preceding items, wherein said first homodimeric antibody has an amino acid other than Lys at position 409 and said second homodimeric antibody has an amino acid other than Phe at position 405.

101. The method according to any of the preceding items, wherein said first homodimeric antibody comprises an Arg at position 409 and said second homodimeric antibody comprises a Leu at position 405.

102. The method according to any of the preceding items, wherein said first and second homodimeric antibodies provided in steps a) and b) are purified.

103. The method according to any of the preceding items, wherein said first and/or second homodimeric antibody is conjugated to a drug, a prodrug or a toxin or contains an acceptor group for the same.

104. The method according to any of the preceding items, wherein the reducing conditions in step c) comprise the addition of a reducing agent.

105. The method according to any of the preceding items, wherein step d) comprises removal of a reducing agent.

106. The method according to any of the preceding items, wherein said first homodimeric antibody and/or second homodimeric antibody binds CD3.

107. The method according to any of the preceding items, wherein said first homodimeric antibody and/or second homodimeric antibody binds CD25.

108. The method according to any of the preceding items, wherein said first homodimeric antibody binds CD3 and said second homodimeric antibody binds CD25.

109. The method according to any of the preceding items, wherein said heterodimeric antibody comprises a sequence of SEQ ID NO:51-69.

110. The method according to any of the preceding items, wherein said heterodimeric antibody comprises a sequence with a least 70%, preferably 75%, more preferred 80%, preferably 85%, more preferred 90%, preferably 95%, more preferred 97% sequence identity to a sequence of SEQ ID NO:51-69.

111. The method according to any of the preceding items, wherein step c) further comprises co-expressing one or more nucleic-acid constructs encoding a light-chain in said host cell.

112. A heterodimeric antibody obtainable by the method according to any of the precedent items.

113. A heterodimeric antibody comprising:
   A first heavy chain comprising a first Fc region, said first Fc region comprising a first CH3 region selected from the group consisting of a human IgG2 CH3 region and a human IgG4 CH3 region, but with an amino acid substitution at position 405 (EU numbering), and
   A second heavy chain comprising a second Fc region, said second Fc region comprising a second CH3 region selected from the group consisting of a human IgG2 CH3 region and a human IgG4 CH3, but with an amino acid substitution at position 409 (EU numbering);
   Wherein the sequences of the first and second CH3 regions are different.

114. A heterodimeric antibody comprising:
   A first heavy chain comprising a first Fc region, said first Fc region comprising a first CH3 region selected from the group consisting of a human IgG2 CH3 region and a human IgG4 CH3 region, and
   A second heavy chain comprising a second Fc region, said second Fc region comprising a second CH3 region selected from the group consisting of a human IgG2 CH3 region and a human IgG4 CH3, but with an amino acid substitution at position 405 and an amino acid substitution at position 409 (EU numbering);
   Wherein the sequences of the first and second CH3 regions are different.

115. The heterodimeric antibody according to any of the preceding items, wherein said first and/or second CH3 region is of human IgG2.

116. The heterodimeric antibody according to any of the preceding items, wherein said first and/or second CH3 region is of human IgG4.

117. The heterodimeric antibody according to any of the preceding items, wherein said first Fc region comprises an Arg at position 409 (EU numbering).

118. The heterodimeric antibody according to any of the preceding items, wherein said second Fc region comprises a Leu at position 405 (EU numbering).

119. The heterodimeric antibody according to any of the preceding items, wherein said first Fc region comprises an Arg at position 409 (EU numbering) and said second Fc region comprises a Leu at position 405 (EU numbering).

120. The heterodimeric antibody according to any of the preceding items, further comprising an amino acid substitution at position 234 (EU numbering).

121. The heterodimeric antibody according to any of the preceding items, further comprising an amino acid substitution at position 235 (EU numbering).

122. The heterodimeric antibody according to any of the preceding items, further comprising an amino acid substitution at position 234 and/or position 235 (EU numbering).

123. The heterodimeric antibody according to any of the preceding items, wherein said heterodimeric antibody comprises an Ala at position 234 (EU numbering).

124. The heterodimeric antibody according to any of the preceding items, wherein said heterodimeric antibody comprises an Ala at position 235 (EU numbering).

125. The heterodimeric antibody according to any of the preceding items, further comprising an amino acid substitution at position 322 (EU numbering).

126. The heterodimeric antibody according to any of the preceding items, wherein said heterodimeric antibody comprises an Ala at position 322 (EU numbering).

127. The heterodimeric antibody according to any of the preceding items, further comprising an amino acid substitution at position 228 (EU numbering).

128. The heterodimeric antibody according to any of the preceding items, wherein said heterodimeric antibody comprises a Pro at position 228 (EU numbering).

129. The heterodimeric antibody according to any of the preceding items, further comprising an amino acid substitution at position 297 (EU numbering).

130. The heterodimeric antibody according to any of the preceding items, wherein said heterodimeric antibody comprises an Ala at position 297 (EU numbering).

131. The heterodimeric antibody according to any of the preceding items, wherein said heterodimeric antibody comprises a hinge region.

132. The heterodimeric antibody according to any of the preceding items, wherein said hinge region is selected from naturally occurring and modified hinge regions.
133. The heterodimeric antibody according to any of the preceding items, wherein said hinge region is selected from the group consisting of naturally occurring IgG1, IgG2, IgG3 and IgG4 hinge regions.
134. The heterodimeric antibody according to any of the preceding items, wherein said hinge region is selected from the group consisting of modified IgG1, IgG2, IgG3 and IgG4 hinge regions.
135. The heterodimeric antibody according to any of the preceding items, wherein said hinge region is having at least 80%, alternatively at least 85%, alternatively at least 90%, alternatively at least 95% sequence similarity to a hinge region selected from the group consisting of naturally occurring IgG1, IgG2, IgG3 and IgG4 hinge regions.
136. The heterodimeric antibody according to any of the preceding items, wherein said heterodimeric antibody comprises a hinge region selected from an IgG1 hinge region or an IgG4 hinge region with a S228P mutation.
137. The heterodimeric antibody according to any of the preceding items, wherein said hinge region comprises two disulfide bonds.
138. The heterodimeric antibody according to any of the preceding items, wherein said hinge region comprises a sequence of CPAP.
139. The heterodimeric antibody according to any of the preceding items, wherein said hinge region comprises a sequence of SEQ ID NO: 72.
140. The heterodimeric antibody according to any of the preceding items, wherein said hinge region comprises a sequence of SEQ ID NO: 72 with one amino acid substitution, one amino acid modification, one amino acid deletion or one amino acid addition.
141. The heterodimeric antibody according to any of the preceding items, wherein said heterodimeric antibody comprises a CH1 region and said CH1 region comprises a Cys within the first 20 amino acid residues of said CH1 region.
142. The heterodimeric antibody according to any of the preceding items, wherein said heterodimeric antibody comprises a CH1 region and said CH1 region comprises a Cys at position 14 of said CH1 region.
143. The heterodimeric antibody according to any of the preceding items, wherein said heterodimeric antibody comprises a CH1 region selected from the group consisting of IgG2 CH1 regions, IgG3 CH1 regions and IgG4 CH1 regions.
144. The heterodimeric antibody according to any of the preceding items, wherein said heterodimeric antibody comprises a linker.
145. The heterodimeric antibody according to any of the preceding items, wherein said first heavy chain and/or said second heavy chain is chimeric, humanized, or human.
146. The heterodimeric antibody according to any of the preceding items, wherein said first and second heavy chains are full-length heavy chains.
147. The heterodimeric antibody according to any of the preceding items, wherein said first and second heavy chains bind different epitopes.
148. The heterodimeric antibody according to any of the preceding items, wherein said first and second heavy chains are full-length heavy chains of two antibodies that bind different epitopes.
149. The heterodimeric antibody according to any of the preceding items, further comprising two full-length light chains.
150. A pharmaceutical composition comprising a heterodimeric antibody according to any of the preceding items and an excipient, such as a pharmaceutically-acceptable carrier.
151. The heterodimeric antibody according to any of the preceding items, wherein said first and/or second heavy chains bind CD3.
152. The heterodimeric antibody according to any of the preceding items, wherein said first and/or second heavy chains bind CD25.
153. The heterodimeric antibody according to any of the preceding items, wherein said first heavy chain binds CD3 and said second heavy chain binds CD25.
154. The heterodimeric antibody according to any of the preceding items, wherein said heterodimeric antibody comprises a sequence selected from the group consisting of SEQ ID NO:51-69.
155. The heterodimeric antibody according to any of the preceding items, wherein said heterodimeric antibody comprises a sequence with a least 70%, preferably 75%, more preferred 80%, preferably 85%, more preferred 90%, preferably 95%, more preferred 97% sequence identity to a sequence selected from the group consisting of SEQ ID NO:51-69.
156. A bispecific antibody or fragment thereof comprising a first antigen binding site capable of binding to a first antigen and a second antigen binding site capable of binding to a second antigen, wherein said first antigen binding site is comprised in a Fab fragment and said second antigen binding site is comprised in a moiety selected from the group consisting of scFv, antibody fragments and protein moiety, wherein said moiety being attached to the light chain of said Fab fragment.
157. The bispecific antibody or fragment thereof according to any of the preceding items, wherein said moiety is a scFv.
158. The bispecific antibody according to any of the preceding items, wherein said moiety is attached to the C-terminus or N-terminus of the light chain of said Fab fragment.
159. The bispecific antibody according to any of the preceding items, wherein said moiety is attached to the C-terminus of the light chain of said Fab fragment.
160. The bispecific antibody according to any of the preceding items, wherein said Fab fragment is derived from an IgG or an IgM.
161. The bispecific antibody according to any of the preceding items, wherein said
Fab fragment is derived from an IgG.
162. The bispecific antibody according to any of the preceding items, wherein said Fab fragment is derived from an IgG selected from the group consisting of IgG1, IgG2, IgG3 and IgG4.
163. The bispecific antibody according to any of the preceding items, wherein said Fab fragment is derived from an IgG2 or an IgG4.
164. The bispecific antibody according to any of the preceding items, wherein said Fab fragment is derived from an IgG2 or an IgG4 as defined according to any of the preceding items.
165. The bispecific antibody according to any of the preceding items, wherein said moiety is attached to a light chain of an IgG2 or IgG4 as defined according to any of the preceding items.

166. The bispecific antibody according to any of the preceding items, wherein said first antigen is CD3 or CD25.
167. The bispecific antibody according to any of the preceding items, wherein said second antigen is CD3 or CD25.
168. A heterodimeric antibody, preferably according to any of the precedent items, wherein said heterodimeric antibody comprises a human IgG4 Fc domain, wherein said heterodimeric antibody binds to two or more different targets and wherein said heterodimeric antibody further comprises a component selected from
    (i) a Fab,
    (ii) a scFv,
    (iii) a variable heavy homodimer (VHH), and/or
    (iv) an antibody fragment.
169. The heterodimeric antibody according to item 168 further comprising a S228P mutation (EU numbering) in the hinge region.
170. The heterodimeric antibody according to any of items 168-169, wherein said heterodimeric antibody comprises
    (i) a first Fc domain comprising native sequence in position 405-409 (EU numbering) of the CH3 domain and
    (ii) a second Fc domain comprising F405L and R409K mutations (EU numbering) in the CH3 domain.
171. The heterodimeric antibody according to any of items 168-170, wherein said heterodimeric antibody comprises a Fc-null mutation selected from the group consisting of V234A, N297A, and K322A (EU numbering).
172. A heterodimeric antibody, preferably according to any of the precedent items, wherein said heterodimeric antibody comprises a human IgG2 Fc domain,
    wherein said heterodimeric antibody binds to two or more different targets and
    wherein said heterodimeric antibody further comprises a component selected from
    (i) a Fab,
    (ii) a scFv,
    (iii) a variable heavy homodimer (VHH), and/or
    (iv) an antibody fragment.
173. The heterodimeric antibody according to item 172, wherein the native IgG2 hinge is replaced by an IgG1 hinge or an IgG4 hinge with S228P mutation (EU numbering).
174. The heterodimeric antibody according to any of items 172-173, wherein said native IgG2 hinge comprises the sequence CCVECPPCPAP (SEQ ID NO:85), said IgG1 hinge comprises the sequence DKTHTCPPCPAP (SEQ ID NO:86) and said IgG4 hinge with S228P mutation comprises the sequence YGPPCPPCPAP (SEQ ID NO:87).
175. The heterodimeric antibody according to any of items 172-174, wherein said heterodimeric antibody comprises
    (i) a first Fc domain comprising a K409R mutation (EU numbering) in the CH3 domain and
    (ii) a second Fc domain comprising a F405L mutation (EU numbering) in the CH3 domain.
176. The heterodimeric antibody according to any of items 172-175, wherein said heterodimeric antibody comprises a Fc-null mutation selected from the group consisting of F234A, L235A, N297A, and K322A (EU numbering).
177. An IgG2, IgG3 or IgG4 molecule that comprises a light chain and an antibody domain and/or protein fused to the C-terminus of said light chain, wherein said antibody domain is selected from
    (i) a Fab,
    (ii) a scFv,
    (iii) a variable heavy homodimer (VHH), and/or
    (iv) an antibody fragment.
178. The IgG2, IgG3 or IgG4 molecule according to item 177 further comprising a linker.
179. The IgG2, IgG3 or IgG4 molecule according to item 178, wherein said linker comprises a GGGGS repeat.
180. The IgG2, IgG3 or IgG4 molecule according to any of items 178-179, wherein said linker comprises a number of GGGGS repeats selected from 1, 2, 3, 4, 5, 6, 7 and 8 repeats, preferably 4-6 repeats.
181. The IgG2, IgG3 or IgG4 molecule according to any of items 178-180, wherein said IgG2, IgG3 or IgG4 molecule comprises a CH1 region and said CH1 region comprises a Cys at position 14 of said CH1 region.

The invention claimed is:

1. An antibody or fragment thereof, capable of binding to CD3 and/or CD25, wherein said antibody or fragment thereof comprises
   a. CDR sequences of SEQ ID NO:73-78, a variable heavy chain domain selected from the group consisting of SEQ ID NO:8-10 and a variable light chain domain selected from the group consisting of SEQ ID NO:3-5, and/or
   b. CDR sequences of SEQ ID NO:79-84, a variable heavy chain domain selected from the group consisting of SEQ ID NO:30-31 and a variable light chain domain selected from the group consisting of SEQ ID NO:33-34.

2. The antibody or fragment thereof according to claim 1, wherein said antibody or fragment thereof further comprises
   a. a scFv comprising a sequence selected from the group consisting of SEQ ID NO:11-28, and/or
   b. a scFv comprising a sequence selected from the group consisting of SEQ ID NO:35-50.

3. The antibody or fragment thereof according to claim 1, wherein said antibody or fragment thereof comprises a sequence selected from the group consisting of SEQ ID NO:51-69.

4. The antibody or fragment thereof according to claim 1, wherein said antibody or fragment thereof comprises a linker and wherein said linker comprises the sequence of SEQ ID NO:71.

5. The antibody or fragment thereof according to claim 1, wherein said antibody or fragment thereof comprises a sequence combination selected from the group consisting of
   a. a variable light chain domain selected from the group consisting of SEQ ID NO:3-5 in combination with a Kappa CL domain of SEQ ID NO:70,
   b. a variable light chain domain selected from the group consisting of SEQ ID NO:33-34 in combination with a Kappa CL domain of SEQ ID NO:70,
   c. a variable heavy chain domain selected from the group consisting of SEQ ID NO:8-10 in combination with a sequence selected from the group consisting of SEQ ID NO:53, SEQ ID NO:60 and SEQ ID NO:66, and
   d. variable heavy chain domain selected from the group consisting of SEQ ID NO:30-31 in combination with a sequence selected from the group consisting of SEQ ID NO:55, SEQ ID NO:62 and SEQ ID NO:68,
wherein the sequence combination comprises one from each of a. through d.

6. The antibody or fragment thereof according to claim 1, wherein said antibody or fragment thereof comprises a sequence combination selected from the group consisting of
   a. a scFv comprising a sequence selected from the group consisting of SEQ ID NO:11-28 in combination with a sequence selected from the group consisting of SEQ ID NO:54, SEQ ID NO:61 and SEQ ID NO:67, and
   b. a scFv comprising a sequence selected from the group consisting of SEQ ID NO:35-50 in combination with a sequence selected from the group consisting of SEQ ID NO:56, SEQ ID NO:63 and SEQ ID NO:69,
wherein the sequence combination comprises one from each of a. and b.

7. The antibody or fragment thereof according to claim 1, wherein said antibody or fragment thereof comprises a sequence combination selected from the group consisting of
   a. a variable light chain domain selected from the group consisting of SEQ ID NO:3-5 in combination with a Kappa CL domain of SEQ ID NO:70,
   b. a linker comprising SEQ ID NO:71,
   c. a scFv comprising a sequence selected from the group consisting of SEQ ID NO:35-50, and
   d. a variable heavy chain domain selected from the group consisting of SEQ ID NO:8-10 in combination with a sequence selected from the group consisting of SEQ ID NO:53, SEQ ID NO:60 and SEQ ID NO:66,
wherein the sequence combination comprises one from each of a. through d.

8. The antibody or fragment thereof according to claim 1, wherein said antibody or fragment thereof comprises a sequence combination selected from the group consisting of
   a. a scFv comprising a sequence selected from the group consisting of SEQ ID NO:11-28,
   b. a sequence selected from the group consisting of SEQ ID NO:54, SEQ ID NO:59 and SEQ ID NO:65,
   c. a linker comprising SEQ ID NO:71, and
   d. a scFv comprising a sequence selected from the group consisting of SEQ ID NO:35-50, wherein the sequence combination comprises one from each of a. through d.

9. The antibody or fragment thereof according to claim 1, wherein said antibody or fragment thereof comprises a sequence combination selected from the group consisting of
   a. a scFv comprising a sequence selected from the group consisting of SEQ ID NO:11-28,
   b. a sequence selected from the group consisting of SEQ ID NO:54, SEQ ID NO:61 and SEQ ID NO:67,
   c. a linker comprising SEQ ID NO:71,
   d. a scFv comprising a sequence selected from the group consisting of SEQ ID NO:35-50,
   e. a scFv comprising a sequence selected from the group consisting of SEQ ID NO:35-50,
   f. a sequence selected from the group consisting of SEQ ID NO:56, SEQ ID NO:63 and SEQ ID NO:69,
   g. a linker comprising SEQ ID NO:71, and
   h. a scFv comprising a sequence selected from the group consisting of SEQ ID NO:11-28,
wherein the sequence combination comprises one from each of a. through h.

10. The antibody or fragment thereof according to claim 1, wherein said antibody or antigen binding fragment allows administration through a route selected among oral and nasal administration.

11. The antibody or fragment thereof according to claim 1, wherein said antibody or fragment thereof is humanized.

12. The antibody or fragment thereof according to claim 1, wherein said antibody or fragment thereof comprises a constant region with a point mutation selected from the group consisting of K409R, R409K, F405L, L234A, F234A, V234A, L235A, K322A and S228P (EU numbering).

13. The antibody or fragment thereof according to claim 1, wherein said antibody or fragment thereof is a monospecific antibody, a bispecific antibody or a multispecific antibody.

14. A diagnostic kit comprising the antibody or fragment thereof according to claim 1 and instructions for use.

15. The diagnostic kit according to claim 14, wherein said diagnostic kit is for companion diagnostic.

16. The diagnostic kit according to claim 14, wherein said diagnostic kit is for the selection of patients that may benefit from treatment with an antibody of fragment thereof according claim 1.

* * * * *